US012759883B2

(12) United States Patent
Cross et al.

(10) Patent No.: US 12,759,883 B2
(45) **Date of Patent: *Oct. 13, 2026**

(54) ALLOTROPE OF CARBON HAVING INCREASED ELECTRON DELOCALIZATION

(71) Applicant: Structured Nano Carbon LLC, Pensacola, FL (US)

(72) Inventors: Charles Danny Cross, Pensacola, FL (US); Larry Herbert Kirby, Lake Jackson, TX (US); Thomas Frank Bailey, Lake Jackson, TX (US)

(73) Assignee: Structured Nano Carbon LLC, Pensacola, FL (US)

( * ) Notice: Subject to any disclaimer, the term of this patent is extended or adjusted under 35 U.S.C. 154(b) by 11 days.

This patent is subject to a terminal disclaimer.

(21) Appl. No.: 18/644,441

(22) Filed: Apr. 24, 2024

(65) Prior Publication Data

US 2025/0223171 A1 Jul. 10, 2025

Related U.S. Application Data

(63) Continuation of application No. 18/133,223, filed on Apr. 11, 2023, now Pat. No. 12,084,350, which is a
(Continued)

(51) Int. Cl.
*C01B 32/194* (2017.01)
*C01B 32/18* (2017.01)
(Continued)

(52) U.S. Cl.
CPC ............ *C01B 32/194* (2017.08); *C01B 32/18* (2017.08); *A61K 33/44* (2013.01); *B82Y 30/00* (2013.01);
(Continued)

(58) Field of Classification Search
CPC ....... C01B 32/18; C01B 32/20; C01B 32/154; C01B 32/156; C01B 32/162; C01B 32/168; C01B 32/194; B08J 5/005; G01N 21/65
See application file for complete search history.

(56) References Cited

U.S. PATENT DOCUMENTS 6,355,857 B1 3/2002 Wagner
6,669,755 B2 12/2003 Wagner
(Continued)

FOREIGN PATENT DOCUMENTS

WO WO2010059505 A1 5/2010

OTHER PUBLICATIONS

Bogdanov, Kirill, et al. "Annealing-induced structural changes of carbon onions: high-resolution transmission electron microscopy and Raman studies," Carbon, 73 (2014): 78-86.
(Continued)

*Primary Examiner* — Richard M Rump

(57) ABSTRACT

Anti-inflammatory agents, antioxidants, electronic devices, batteries, capacitors, lubricants, coatings and paints, each containing a newly discovered allotrope of carbon having a multilayered nanocarbon array, and which exhibits, among other properties, exceptional stability, electrical conductivity and electromagnetic frequency (emf) attenuation characteristics. Members of this new allotrope include nanocarbon structures possessing vast electron delocalization in multiple directions, unavailable to known fullerene-characterized materials like carbon nano-onions (CNOs), multiwalled carbon nano-tubes (MWNTs), graphene, carbon nano-horns, and carbon nano-ellipsoids. Such stabilizing electron delocalization crosses or proceeds between layers, as well as along layers, in multiple directions within a continuous cyclic structure having an advanced interlayer connectivity
(Continued)

TGA Temperature (Thermodynamic Stability) vs Annealing Temperature ($E_{act}$) ( °C )

Palkar Reference: Nanodiamond and Underwater Arc Discharge

Disclosure: Catenated

| Source Material | Layer Count | Annealing Temp C | TGA C | Allotrope |
|---|---|---|---|---|
| | | | | |
| Nanodiamond | 6-8 | 1650 | 700 | Crossene CNO |
| | | | | |
| | | | | |
| Arc Discharge | 25 (avg) | 1650 | 500 | Fullerene CNO |
| Arc Discharge | 25 (avg) | 2300 | 700 | Crossene CNO |
| | | | | |
| | | | | |
| Catenated | 25 (avg) | 1650 | 500 | Fullerene CNO |
| Catenated | 25 (avg) | 2000 | 700 | Crossene CNO |
| Catenated | 25 (avg) | 2200 | 700 | Crossene CNO |
| Catenated | 25 (avg) | 2600 | 700 | Crossene CNO |
| Catenated | 25 (avg) | 2800 | 700 | Crossene CNO |
| | | | | |

bonding system involving the whole carbon array, apart from incidental defects.

31 Claims, 16 Drawing Sheets

Related U.S. Application Data continuation of application No. 16/921,872, filed on Jul. 6, 2020, now Pat. No. 11,718,530, which is a continuation-in-part of application No. 15/925,650, filed on Mar. 19, 2018, now abandoned.

(60) Provisional application No. 62/490,500, filed on Apr. 26, 2017, provisional application No. 62/473,152, filed on Mar. 17, 2017.

(51) Int. Cl.

| | |
|---|---|
| *A61K 33/44* | (2006.01) |
| *B82Y 30/00* | (2011.01) |
| *B82Y 40/00* | (2011.01) |
| *C08K 3/04* | (2006.01) |
| *C10M 125/02* | (2006.01) |

(52) U.S. Cl.

CPC .......... *B82Y 40/00* (2013.01); *C01B 2204/04* (2013.01); *C01B 2204/22* (2013.01); *C01P 2004/32* (2013.01); *C08K 3/042* (2017.05); *C10M 125/02* (2013.01)

(56) References Cited

U.S. PATENT DOCUMENTS

| | | | |
|---|---|---|---|
| 7,034,197 | B2 | 4/2006 | Wagner |
| 7,814,846 | B2 | 10/2010 | Wagner |
| 7,815,885 | B2 | 10/2010 | Wagner |
| 7,901,653 | B2 | 3/2011 | Wagner |
| 7,922,993 | B2 | 4/2011 | Wagner |
| 8,071,534 | B2 | 12/2011 | Wagner et al. |
| 8,197,787 | B2 | 6/2012 | Wagner |
| 8,263,037 | B2 | 9/2012 | Wagner |
| 8,299,014 | B2 | 10/2012 | Wagner et al. |
| 8,563,501 | B2 | 10/2013 | Wagner et al. |
| 9,133,033 | B2 | 9/2015 | Wagner |
| 9,216,905 | B2 | 12/2015 | Presswood et al. |
| 9,504,998 | B2 | 11/2016 | Koveal, Jr. et al. |
| 9,987,608 | B2 | 6/2018 | Pigos |
| 10,316,375 | B2 | 6/2019 | Presswood et al. |
| 11,359,253 | B2 | 6/2022 | Presswood et al. |
| 11,718,530 | B2 | 8/2023 | Cross et al. |
| 12,084,350 | B2 | 9/2024 | Cross et al. |
| 2006/0008406 | A1 | 1/2006 | Wagner |
| 2008/0226511 | A1 | 9/2008 | Wagner |
| 2009/0065985 | A1 | 3/2009 | Wagner |
| 2017/0081190 | A1 | 3/2017 | Burchfield et al. |
| 2018/0155199 | A1 | 6/2018 | Burchfield et al. |
| 2018/0265359 | A1 | 9/2018 | Cross et al. |
| 2018/0265361 | A1 | 9/2018 | Burchfield |
| 2022/0282345 | A1 | 9/2022 | Presswood et al. |
| 2024/0200158 | A1 | 6/2024 | Bishop et al. |
| 2024/0417262 | A1 | 12/2024 | Bishop et al. |

OTHER PUBLICATIONS

Amini, et al., "Growth of Large-Area Graphene Films from Metal-Carbon Melts," 2010, 1-21.

Formation and Physical Properties of Novel Carbonaceous Nano-Materials, Kobe University Repository: Thesis 2002, DP-1-125.

Palkar, Amit, et al. "Reactivity differences between carbon nano onions (CNOs) prepared by different methods," Chemistry—An Asian Journal 2 (2007): 625-633.

Bogdanov, Kirill, et al. "Annealing-induced structural changes of carbon onions: high-resolution transmission electron rnicroscopy and Raman studies," Carbon, 73 (2014): 78-86.

Shames et al., "Closed pi-Electron Network in Large Polyhedral Multi-Shell Carbon Nanoparticles," 2008, 1-32.

Pujals et al., "XPS of Carbon Nanostructures Obtained by Underwater Arc Discharge of Graphite Electrodes," Nucleus N(0), 64, 2018, 15-18.

Andres et al., "Strong Covalent Bonding Between Two Graphene Layers," 2013, 1-11.

Choucair et al., "The Gram-Scale Synthesis of Carbon Onions," Carbon, 50, 2012, 1109-1115.

Hawelek et al., "Transformation of Nano-Diamonds to Carbon Nano-Onions Studied by X-Ray Diffraction and Molecular Dynamics," Diamond & Related Materials, 20, 2011, 1333-1339.

Jurkiewicz et al., "Structure of Carbon Materials Explored by Local Transmission Electron Microscopy and Global Powder Diffraction Probes," Journal of Carbon Research, 2018, 1-48.

Sabalot-Cuzzubbo et al., "Relating the Shape of a Molecule and its Reactivity—Haddon's Curvature and the Pyramidalization Angle," HAL Archives-Ouvertes, 2020, 1-22.

R. C. Haddon, "Comments on the Relationship of the Pyramidalization Angle at a Conjugated Carbon Atom to the Sigma Bond Angles," J. Phys. Chem. A, 2001, 105. 4164-4165.

Georgakilas et al., "Broad Family of Carbon Nanoallotropes: Classification, Chemistry, and Applications of Fullerenes, Carbon Dots, Nanotubes, Graphene, Nanodiamonds, and Combined Superstructures," Chem. Rev., 115, 2015, 4744-4822.

Baronnet et al., "Onion Morphology and Microstructure of Polyhedral Serpentine," HAL Archives-Ouvertes, 2007, 1-16.

Tomita et al., "Structure and Electrical Properties of Carbon Onions, The Journal of Chemical Physics," 114, 2001, 7477-7482.

Terrones et al., "Curved Nanostructured Materials," New Journal of Physics, 5, 2003, 126.1-126.37.

McDonough et al., "Carbon Onions: Synthesis and Electrochemical Applications," The Electrochemical Society Interface, 2013, 61-66.

Echegoyen et al., "Carbon Nano Onions," Chemistry of Nanocarbons, Ch. 19, 2010, 463-483.

Usol'tseva, N. V., et al. "Rheological characteristics of different carbon nanoparticles in cholesteric mesogen dispersions as lubricant coolant additives." Journal of Friction and Wear 36.5 (2015): 380-385.

Gurevich, V. L. "Stability of microprocessor relay protection and automation systems against intentional destructive electromagnetic impacts. Part 2." EneKTPOTexHiKa i eneKTPOMexaHiKa (2011).

Ignatov, Ignat, and O. V. Mosin. "Carbonaceous Fullerene Containing Mineral Shungite. Research of Influence of Shungite on Mountain Water." Journal of Medicine, Physiology and Biophysics 11 (2015): 22-38.

Mosin, O. V., and Ignat Ignatov. "The structure and composition of natural carbonaceous fullerene containing mineral shungite." International Journal of Advanced Scientific and Technical Research 6.11-12 (2013): 9-21.

Obraztsova, E. D., et al. "Raman identification of onion-like carbon." Carbon 36.5-6 (1998): 821-826.

Clean Tech Brochure, 2006, pp. 1-4.

Clean Tech Brochure—Annotated, 2006, pp. 1-4 (See also Exhibit A (Declaration filed in parent U.S. Appl. No. 16/921,872)).

Document A, pp. 1-23 (Nov. 2016-Oct. 2018 (See also Exhibit B (Declaration filed in parent U.S. Appl. No. 16/921,872)).

Document A, pp. 24-35 (Nov. 2016-Oct. 2018 (See also Exhibit B (Declaration filed in parent U.S. Appl. No. 16/921,872)).

Document A, pp. 36-47 (Nov. 2016-Oct. 2018 (See also Exhibit B (Declaration filed in parent U.S. Appl. No. 16/921,872)).

E. A. Golubev, "Electrophysical Properties and Structural Features of Shungite (Natural Nanostructured Carbon)," Physics of the Solid State, vol. 55, No. 5, 2013, pp. 1078-1086.

E. F. Sheka et al., "Shungite as the Natural Pantry of Nanoscale Reduced Graphene Oxide," International Journal of Smart and Nano Materials, 2014, vol. 5, No. 1, pp. 1-16.

I. Alexandrou et al., "Structure of Carbon Onions and Nanotubes Formed by Arc in Liquids," J. Chem. Phys., vol. 120, No. 2, 2004, pp. 1055-1058.

(56) References Cited

OTHER PUBLICATIONS

N. Sano et al., “Synthesis of Carbon ‘Onions’ in Water,” Nature, vol. 414, 2001, pp. 506-507.
J. Bartelmess et al., “Carbon Nano-Onions (Multi-Layer Fullerenes): Chemistry and Applications,” Beilstein Journal of Nanotechnology, 2014, 5, pp. 1980-1989.
N. Obradovic et al., “Shungite—A Carbon-Mineral Rock Material: Its Sinterability and Possible Applications,” Processing and Applications of Ceramics, 13, [1], 2019, pp. 89-97.
S. V. Krasnovyd et al., “Local Structure and Paramagnetic Properties of the Nanostructured Carbonaceous Material Shungite,” Nanoscale Research Letters, 2015, 10:78, pp. 2-7.
A. Smekens et al., “Characterization of Individual Soot Aggregates from Different Sources Using Image Analysis,” J. Atmos. Chem., 2007, 56, pp. 211-223.
Bu, Ian YY. “Synthesis of graphitic carbon nano-onions for dye sensitized solar cells.” Solar energy 105 (2014): 236-242.
Bartkowski, Michal, and Silvia Giordani. “Supramolecular chemistry of carbon nano-onions.” Nanoscale 12.17 (2020): 9352-9358.
Liu, Yu, Randy L. Vander Wal, and Valery N. Khabashesku. “Functionalization of carbon nano-onions by direct fluorination.” Chemistry of materials 19.4 (2007): 778-786.
Rozhkova, Natalia N. “Role of fullerene-like structures in the reactivity of shungite carbon as used in new materials with advanced properties.” Perspectives of fullerene nanotechnology. Springer, Dordrecht, 2002. 237-251.
J. Bartelmess et al., “Carbon Nano-Onions (Multi-Layer Fullerenes): Chemistry and Applications,” Beilstein Journal of Nanotechnology, 2014, 5, pp. 1990-1998.

*FIG. 1A*

THERMODYNAMIC STABILITY (TGA) COMPARISON
"THERMODYNAMIC STABILITY"

| AVE DEG FULLERENE | AVE DEG CROSSENE | FACTOR % |
|---|---|---|
| 508 | 652.0 | + 28% |
| 100% ACETYLENE BLACK 248 | 652.0 | + 163% |

HIGH THERMAL STABILITY AND PURITY OF CROSSENE MATERIALS AS SHOWN FROM TGA

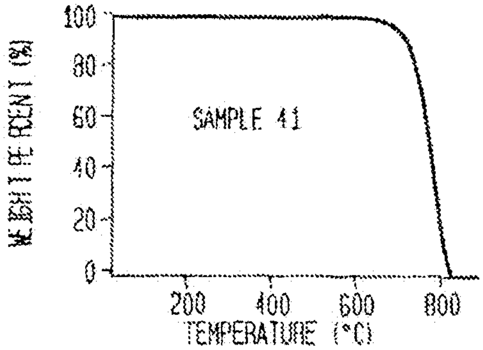

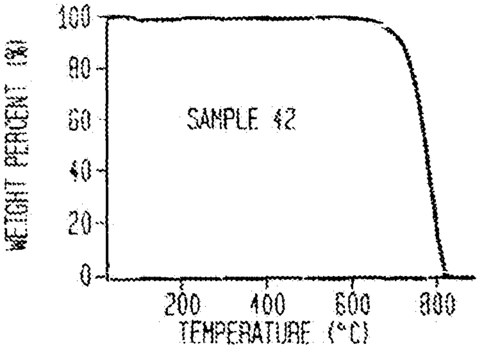

CONDUCTED UNDER THE FOLLOWING CONDITIONS:
BALANCE GAS: NITROGEN 40.0 mL/min; SAMPLE GAS: AIR 60.0 mL/min. RAMP 20.00° C/min TO 900° C

| SAMPLES | RESIDUAL MASS (wt%) | COMBUSTION TEMP. (°C) |
|---|---|---|
| 41 | 0 | 628 |
| 42 | 0.16 | 676 |

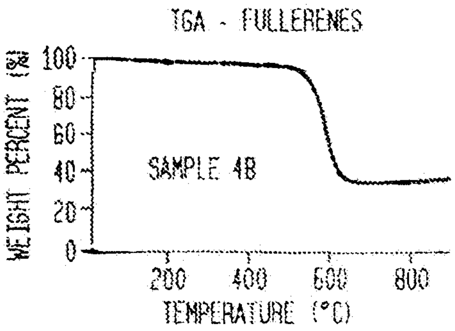

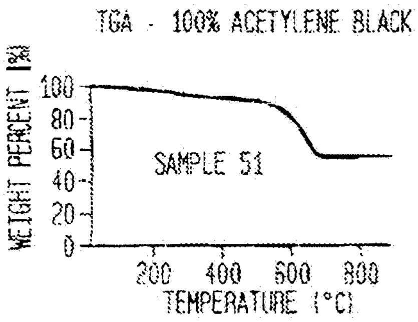

CONDUCTED UNDER THE FOLLOWING CONDITIONS:
BALANCE GAS: NITROGEN 40.0 mL/min; SAMPLE GAS: AIR 60.0 mL/min. RAMP 20.00° C/min TO 900° C

| SAMPLES | RESIDUAL MASS (wt%) | COMBUSTION TEMP. (°C) |
|---|---|---|
| 48 | 38 | 508 |
| 51 | 61 | 248 |

*FIG. 1B*

TGA Temperature (Thermodynamic Stability) vs Annealing Temperature ($E_{act}$) ( °C )

Palkar Reference: Nanodiamond and Underwater Arc Discharge

Disclosure: Catenated

| Source Material | Layer Count | Annealing Temp C | TGA C | Allotrope |
|---|---|---|---|---|
| | | | | |
| Nanodiamond | 6-8 | 1650 | 700 | Crossene CNO |
| | | | | |
| | | | | |
| Arc Discharge | 25 (avg) | 1650 | 500 | Fullerene CNO |
| Arc Discharge | 25 (avg) | 2300 | 700 | Crossene CNO |
| | | | | |
| | | | | |
| Catenated | 25 (avg) | 1650 | 500 | Fullerene CNO |
| Catenated | 25 (avg) | 2000 | 700 | Crossene CNO |
| Catenated | 25 (avg) | 2200 | 700 | Crossene CNO |
| Catenated | 25 (avg) | 2600 | 700 | Crossene CNO |
| Catenated | 25 (avg) | 2800 | 700 | Crossene CNO |
| | | | | |

CROSSENE CARBON NANO STRUCTURE CHARACTERIZATION
"GRAPHETIC PEAK INTENSITY" BY XRD

CROSSENE CARBON NANO STRUCTURE CHARACTERIZATION
"ELECTRICAL CONDUCTIVITY"

| | FULLERENE | CROSSENE | FACTOR % |
|---|---|---|---|
| R≈ | 3,300 | 1.1 | 300,000% |
| P= | 37,451 | 13.9 | 269,432% |

ELECTRICAL CONDUCTIVITY

FULLERENE IN CHAINS - SEM - IMAGE 25000

FULLERENE IN CHAINS - SEM - IMAGE 100,000

FULLERENE IN CHAINS - HRTEM - IMAGE 150,000

FULLERENE IN CHAINS - HRTEM - IMAGE 500,000

CROSSENE IN CHAINS - HRTEM - IMAGE 100,000

CROSSENE IN CHAINS - HRTEM - IMAGE 100,000

CROSSENE IN CHAINS - HRTEM - IMAGE 500,000

CROSSENE IN CHAINS - HRTEM - IMAGE 500,000

*FIG. 6*

SURFACE AREA AND POROSITY FOR CATENATED CARBON NANO-ONIONS (CNOs)

KEY FOR CATENATED CARBON NANO-ONIONS (CNO's)

| Sample | Description | BET Surface Area ($m^2/g$) | Pore Volume ($cm^3/g$) | Pore Size (A) |
|---|---|---|---|---|
| 1 | Fullerene (Unannealed) | 41.58 | 0.1107605 | 105.464 |
| 2 | Crossene (Annealed at 2000 °C) | 47.79 | 0.1795245 | 128.745 |
| 3 | Crossene (Annealed at 2200 °C) | 50.97 | 0.197407 | 135.408 |
| 4 | Crossene (Annealed at 2300 °C) | 24.18 | 0.0889905 | 118.725 |
| 5 | Crossene (Annealed at 2550 °C) | 51.82 | 0.193907 | 121.712 |
| 6 | Crossene (Annealed at 2800 °C) | 44.99 | 0.165785 | 124.048 |

FIG. 7

| Monotropic Carbon Allotrope Rankings | Diamond (nanodiamond) | Graphite | Fullerene CNO | Crossene CNO |
|---|---|---|---|---|
| Thermodynamic Stability | "1" | "2" | "3" | "4" |
| Electron Delocalization | None | "1" | "2" | "3" |
| TGA | | | 500°C | 700°C |
| Source | Graphite Detonation | Natural | Nanodiamond Annealing | Nanodiam/Fuller Annealing |
| Structure | Lattice | Layered | Layered | Layered |
| Geometry | Tetrahedral (sp3) | Planar (sp2) | Concentric (sp2) Spherical | Irregular (sp2) Spheroidal/Ribbon |
| Necessary Annealing Temperature | 1100-1500°C to fCNO/1650-1900°C to cCNO | Laser/Arc Discharge /Plasma to CNOs | 1650°C+ (also Nanodiamond) | N/A |
| Substituents per Carbon Atom | Four | Three | Three | Three |
| C-C Bond Lengths | All Equivalent | All Equivalent | All Equivalent | All Equivalent |
| C-C Bond Angles | All Equivalent | All Equivalent | Equivalent per Layer | Varies with Irregularity |
| Bond Saturation | Full | Singly Unsaturated | Singly Unsaturated | Singly Unsaturated |
| Electron Delocalization | None | "1" | "2" | "3" |
| Degree of Delocalization | None | Finite - Limited by Edges | Infinite | Infinite |
| Nature of Electron Delocalization | None | Both Sides - Independent Layers | Both Sides - Independent Layers | Both Sides - Connected Layers |
| Delocalized Electron Distribution | None | Same on Both Sides | Exterior/Interior Sides Opposite | Varies with Irregularity |
| Electron Count per Side/Carbon Count | None | Odd/Even | Even/Even | Even/Even |

Illustration showing the transformation steps of nanodiamond to hollow onion-like carbon

ALLOTROPE OF CARBON HAVING INCREASED ELECTRON DELOCALIZATION

CROSS-REFERENCE TO RELATED APPLICATIONS

This present application is a continuation of U.S. application Ser. No. 18/133,223, filed Apr. 11, 2023, now U.S. Pat. No. 12,084,350, which is continuation of U.S. application Ser. No. 16/921,872, filed on Jul. 6, 2020, now U.S. Pat. No. 11,718,530, which is a continuation-in-part of U.S. application Ser. No. 15/925,650 filed Mar. 19, 2018, now abandoned, which claims the benefit of U.S. Provisional Application 62/490,500 filed on Apr. 26, 2017, and U.S. Provisional Application 62/473,152 filed on Mar. 17, 2017.

BACKGROUND

Field

Multilayered nanocarbon materials, such as previously known nanocarbon onions (NCOs) or carbon nano-onions (CNOs), onion-like carbons (OLCs), carbon nano-horns, multiwalled carbon nano-ellipsoids and carbon nanotubes (MWNTs) which are known examples of the fullerene allotrope wherein types of graphitic bonding describe the structure of individual layers.

Description of the Related Art

Certain elements of the periodic table of chemistry exhibit allotropy (Encyclopedia Britannica on Internet: https:/the/www.britannica.com/science/allotrope Jul. 20, 1998) whereby pure elements present themselves in different forms as in arrangement of atoms in crystalline solids or in molecular forms that are differentiated on the basis of bearing different numbers and/or alignment and bonding of atoms that are generally manifested by different shapes and/or different physical and chemical properties. Allotropes may be monotropic, whereby one allotropic form is the most stable under all conditions, or they may be enantiotropic, whereby different forms are stable under different conditions and undergo reversible transitions from one to another at characteristic temperatures and pressures.

Elements exhibiting allotropy include carbon, tin, sulfur, phosphorus, and oxygen. Tin and sulfur are enantiotropic whereby tin exists in a gray form, stable below 13.2° C., and a white form, stable at higher temperatures; sulfur forms rhombic crystals, stable below 95.5° C., and monoclinic crystals, stable between 95.5° C. and the melting point (119° C.). Phosphorus and oxygen are monotropic whereby red phosphorus is more stable than white phosphorus, and diatomic oxygen, having the formula 02, is more stable than triatomic oxygen (ozone, 03) under all ordinary conditions.

Before 1985, carbon was characterized as monotropic with graphite demonstrating greater stability over diamond under normal pressure and temperature and with no consideration given to a catch-all disorganized amorphous carbon. Today, the basis of these two allotropic carbons is connected to a difference in crystalline form that is tied to a different type of bonding between the carbons involved in the respective allotropes.

The diamond allotrope (Mark Weller, Tina Overton, Jonathan Rourke, Frazer Armstrong, Shriver & Atkins' *Inorganic Chemistry*, $5^{th}$ Edition, Chapter 14 (2014)) possesses saturation in its bonding nature and exhibits a tetrahedron arrangement of carbon atoms bonded to one another head-to-head or head-on for maximum orbital overlap. Accordingly, a maximum bond-strength is achieved through sigma bonding only. Such strength is attributed to carbon atoms bearing a saturated bonding nature of a theorized three-dimensional hybridization of the one atomic s and three (x, y, and z) atomic p orbitals organized into a tetragonal bonding arrangement of the sp3 hybridized carbons wherein each carbon is perfectly separated at equidistance and equivalent tetrahedral bond angles of 109.47 degrees from every adjacent carbon and without the involvement of loose unaccounted-for electrons.

The graphite allotrope, on the other hand, possesses unsaturation in its bonding nature exhibiting a trigonal bonding arrangement associated with a theorized planar sp2 hybridization for each carbon in the system wherein each of three sp2 orbitals are bonded head-to-head or head-on with maximum orbital overlap and bond strength to one another through sigma bonding in planar fashion with each bond equidistant between respective bonded carbon atoms and oriented at 120 degree angles to one another. Left over from the sp2 hybridized bonding is a p orbital bearing an unpaired loose unaccounted-for electron that aligns with the p-orbitals left over from its adjacent sp2 carbon atom neighbors thereby allowing the maximum of tangential overlap for the otherwise loose electrons from each sp2 carbon thereby producing, through tangential overlap, pi bonds between respective carbon atoms which couple to other conjugated pi bonds to create a planar system of delocalized electrons with limits due only to the edges of the graphitic carbon planar structure or defects therein.

Without an understanding of the potential of conjugated pi bonds, one might expect that four strong sigma bonds would result in higher overall stability to just three strong sigma bonds with only the involvement of a weaker pi bond deriving from the loose electron of the separate p-orbital. In fact, the unconjugated pi bond is prone to reaction to convert the unsaturated sp2 to the saturated sp3 hybridization arrangement whereby all bonds become sigma. The pi bonds, however, have electrons involved with an ability to spread out over a whole system of connected pi bonds if the pi bonds are conjugated with one another. Such spreading out of electrons over a system of conjugated pi bonds creates a system of delocalized electrons that have been proven to yield a more stable overall system particularly in an endless cyclic arrangement. Accordingly, the trivalently bonded graphite allotrope with trigonally sigma bonded carbon atoms all in a plane is more thermodynamically stable than the quadrivalently bonded diamond allotrope with tetragonally sigma bonded carbon atoms.

Such differential bonding of conjugated vs. unconjugated systems is the basis of explaining the otherwise unexpected stability to reactivity of benzene or aromatic materials as compared to isolated pi bonds and is characterized by the term "resonance stabilization" that accrues from a strong degree of electron delocalization arising from a complete loop and correspondingly exhibits electrical current equivalence over the six-membered ring without any interrupting insulation or discontinuity of a saturated sp3 carbon. Such a molecular current resembles macroscopic current in that benzene or aromatic rings exhibit delocalized electron currents demonstrable via nuclear magnetic fields associated with the resonance effects, thus characterized and utilized via the nuclear magnetic resonance (nmr) phenomenon. With the sp2 carbons involved having a planar arrangement, a useful way of viewing benzene is to think of there being a donut-shaped cloud of pi delocalized electrons above and below the planar ring. Accordingly, aromatic systems exhibit substantially different properties as in reactivities being amenable to electrophilic substitution as opposed to the traditionally expected addition of isolated pi bonds.

With these underlying bonding considerations in mind, graphite which consists of multiple layers or sheets of fused benzene rings, one can see a remarkable degree of stabilization likened to "resonance stabilization" of benzene as result of the pi electrons, arising from the p orbitals from the sp2 hybridization of the carbon atoms involved in the structure, being delocalized molecularly over a planar sheet of interconnected and overlapping p-orbitals. Even though stronger molecular bonds between individual carbon atoms arise from the sigma bond due to its greater degree of head-on orbital overlap, the lesser degree of overlap of a tangential, non-head-on arrangement of adjacent p-orbitals results in forming the highly stabilizing pi electron cloud or network of electron delocalization with half the lobes of each p-orbital interacting above the plane of the graphite sheets and the other half below the plane as with the benzene delocalization through a donut cloud above and below its plane. With this in mind, the properties of graphite make sense with graphite being the more thermodynamically stable allotrope over diamond and also having a high degree of electrical conductivity through the corresponding electron delocalization throughout each plane. Additionally, tribological (lubricant) properties differ dramatically between graphite and diamond allotropes in that graphite bears only weak van der Waal forces between its only weakly interacting planes as opposed to actual complete sigma bonding crosslinking through sp3 hybridization of all layers of the diamond structure; therein the lubricity of graphite, perhaps involving intercalated impurities, stands in sharp contrast to the extreme abrasiveness of diamond surfaces.

In 1985 (Kroto H W, Heath J R, O'Brien S C, Curl R F, Smalley R E. C60*: Buckminsterfullerene. Nature.* 1985, 318 (6042): 162-3 doi: 10.1038/318162a0), Smalley, Curl and Kroto discovered buckminsterfullerene or "buckyball," the first example of a nanocarbon allotrope bearing the name fullerene that shows correspondence to graphite because of the presence of electron delocalization capability. Fullerenes of generally larger sizes were subsequently discovered thereby leading to "buckyball" taking on the designation of C60 fullerene because of it bearing sixty carbons. Besides simple spheres possessing different carbon counts, the fullerene allotrope possesses a number of different general carbon structures of varying shapes generally described as bearing graphitic bonding. This fullerene allotrope is presented to include the following materials: nanocarbon onions (NCOs) or carbon nano-onions (CNOs), onion-like carbons (OLCs), carbon nano-horns, carbon nano-ellipsoids and multiwalled carbon nanotubes (MWNTs) as compared to single walled nanotubes (SWNTs) for example, even having graphene being considered by some in its realm due to its nanocarbon size and its graphitic bonding nature.

As noted with graphite and also applicable to the single and multiple layer variations of graphene, electron delocalization is foundational to fullerene properties that is similar to but far from identical to the case of electron delocalization for individual sp2-hybridization in fused benzene ring components like naphthalene or anthracene. It is the curvature of fullerenes of structure that distinguishes fullerenes from planar systems like graphenes and graphite. This curvature dramatically alters the interaction of the p-orbital-like orbitals that might better be characterized as part of a sp2.3 or sp2.4 system or a highly strained sp2 system thereby yielding entirely different and unique properties from graphene or graphite systems of similar trigonally bonded carbons.

Also, unlike planar graphite that possesses the limitation to electron delocalization of edges, spherical fullerene molecules possess no edges, apart from defects in structure, arising from their cyclic structure with uninterrupted continuous delocalization through a kind of graphitic bonding system. Such a continuous cyclic arrangement compares to individual benzene in isolation with a cyclic delocalization above and below the six-membered ring but in a planar structure with equivalent bond lengths between the carbons in the aromatic ring.

With benzene, the electron delocalization is accompanied with an improvement of thermodynamic stabilization as noted according to measurable resonance stabilization with two contributing resonance structures wherein the double and single bonds are interchanged. This thermodynamic stabilization is demonstrated by comparing heats of hydrogenation for benzene versus cyclohexene or cyclohexadienes. The driving force for the existence of fullerenes can likewise be viewed to be attributed to electron delocalization with an even greater resonance stabilization possibility because of the plethora of possible three-dimensional resonance structures (12,500 for C60-fullerene), though somewhat impaired due to the strain of curvature that correspondingly reduces tangential overlap of p-orbitals of adjacent carbon atoms on the convex side of the curved surface due to the p-orbital-like orbitals diverging apart from one another at an angle (Mark Weller, Tina Overton, Jonathan Rourke, Frazer Armstrong, Shriver & Atkins' *Inorganic Chemistry*, $5^{th}$ Edition, Chapter 14 (2014) p, 388) which is compensated by the concave side's high degree of tangential overlap due to p-orbital-like orbitals converging towards one another and the center of the spherical structure. As a result of such strain resulting in the diverging radial orientation of the p-orbital-like orbitals on the exterior surface of the fullerene bearing loose or free electrons, unlike with benzene with orthogonally aligned p-orbitals, the fullerenes are susceptible to addition reactions likened to that for simple isolated (unconjugated) and unstrained olefins with orthogonally aligned p-orbitals for optimal tangential overlap. In contrast to such isolated pi bonds, benzene and other aromatic systems with associated disposable C—H (carbon-to-hydrogen) hydrogens seek to retain their resonance stabilization by disallowing addition reactions that would interrupt stabilizing electron delocalization and instead participate in electrophilic substitutions of one or more of the aromatic ring disposable hydrogens thereby allowing the reestablishment of the resonance stabilized aromatic system and its stabilizing electron delocalization over the six-membered ring.

For these prior fullerene allotropes, simple fullerene-like nanocarbon materials of the multilayer nature as of CNOs or NCOs, OLCs and MWNTs are explained generally to exist as sets of nested fullerene spheres or tubes or graphitic layers with each layer of resonance stabilization bonding being an isolated layer unto itself with only "van der Waal" attraction forces between layers similar to that of graphite or multilayered graphene but with the geometrical constraint of a continuous sphere as opposed to a separating, a sliding or displacing movement of layers of graphite or multilayer graphene. Each fullerene is described as having a similar nature to graphite particularly in that each carbon is bonded through sigma-like bonds to only three other carbons in the allotrope and displays a Raman spectroscopy peak similar to that of graphite or graphene, a strong G ("graphitic") peak. Besides the similarity of respective delocalizations and fullerene and graphite or graphene attributes arising from trigonally substituted carbons with a free p-orbital or p-orbital-like orbital orthogonal to the other three sigma bonds, high resolution transmission electron micrographs (HRTEM) reveal layer separations of 0.34 nm for each. For the onion fullerene structures, publications generally report the number of layers varying between 5 and 30 depending on the method of synthesis.

SUMMARY

A new allotrope of multilayered nanocarbon materials is herein introduced with an advanced bonding system of superior electron delocalization. Hitherto in the literature, the fullerene allotrope has been understood to encompass generally all trigonally bonded carbon systems of a curved nature and some would lump the nanocarbon graphene carbon materials into the fullerene category as well. Of particular focus of this invention is nanocarbon onions (NCOs) or carbon nano-onions (CNOs) or onion-like carbons (OLCs) wherein the systems possess a preponderance of generally complete continuous or cyclic layers without edges though some carbon nanotubes or graphenes with a high degree of multiple layers might harbor interest in regards to their possible relationship to this new allotrope, particularly if their edges could convert to a continuous cyclic system. The cavalier characterization of most all nanocarbons as being part of the fullerene family along with limitations of synthetic procedures of marginal yield and consistency in terms of numbers of layers and purity coupled to imprecise consideration of the bonding involved to be like that of graphite or graphene has been a severe stumbling block in the progression of the development of the nanocarbon technology since its inception in 1985 by Smally, Curl and Kroto with the discovery of the first fullerene molecule affectionately known as the Buckyball.

The new allotrope is formed through exposure of carbonaceous material, especially of multilayered nanocarbon materials particularly of the fullerene family and especially of spherical morphology, under carefully controlled residence times and temperature and pressure and atmospheric profiles compatible with what would generally be considered by others to be extreme conditions that should be avoided. Optimally the carbonaceous material is that of multilayered nanocarbon materials, particularly of the spherical fullerene family and especially of relatively low surface area produced at extreme conditions with high reproducibility and purity, without need for post-treatment with chemicals. Valued properties of the new allotrope are expected to improve dramatically with CNOs of greater number of layers. Due to the extreme conditions, the carbonaceous material undergoes a controlled disassembly and subsequent reassembly and rearrangement to a dramatically different bonding system of a far more thermodynamically stable allotrope. Spherical-like or spheroidal members, in contrast to tubular or planar analogs, possess a molecular formula of Cx where x ranges typically from about ten thousand to half a million and to two million to twenty million or more for more complex Cx structures resulting from catenation, for example, and a thousand times those numbers at the limits of the accepted nanocarbon range just below 100 nm in size.

Members of this new allotrope comprise multilayered nanocarbons that exhibit a dramatic difference in properties from members of the fullerene allotrope. Such properties, in part, are revealed in the realm of electrical conductivity, electromagnetic frequency (emf) attenuation, and thermal and oxidative stability.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 1A presents a Thermogravimetric Analysis comparison of a crossene allotrope sample to a fullerene allotrope sample.

FIG. 1B presents a Thermogravimetric Analysis listing some nano-onions annealed at varying temperatures.

FIG. 6 presents surface and porosity data for catenated carbon nano-onions.

FIG. 7 presents a comparison of all four carbon allotropes.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 2:
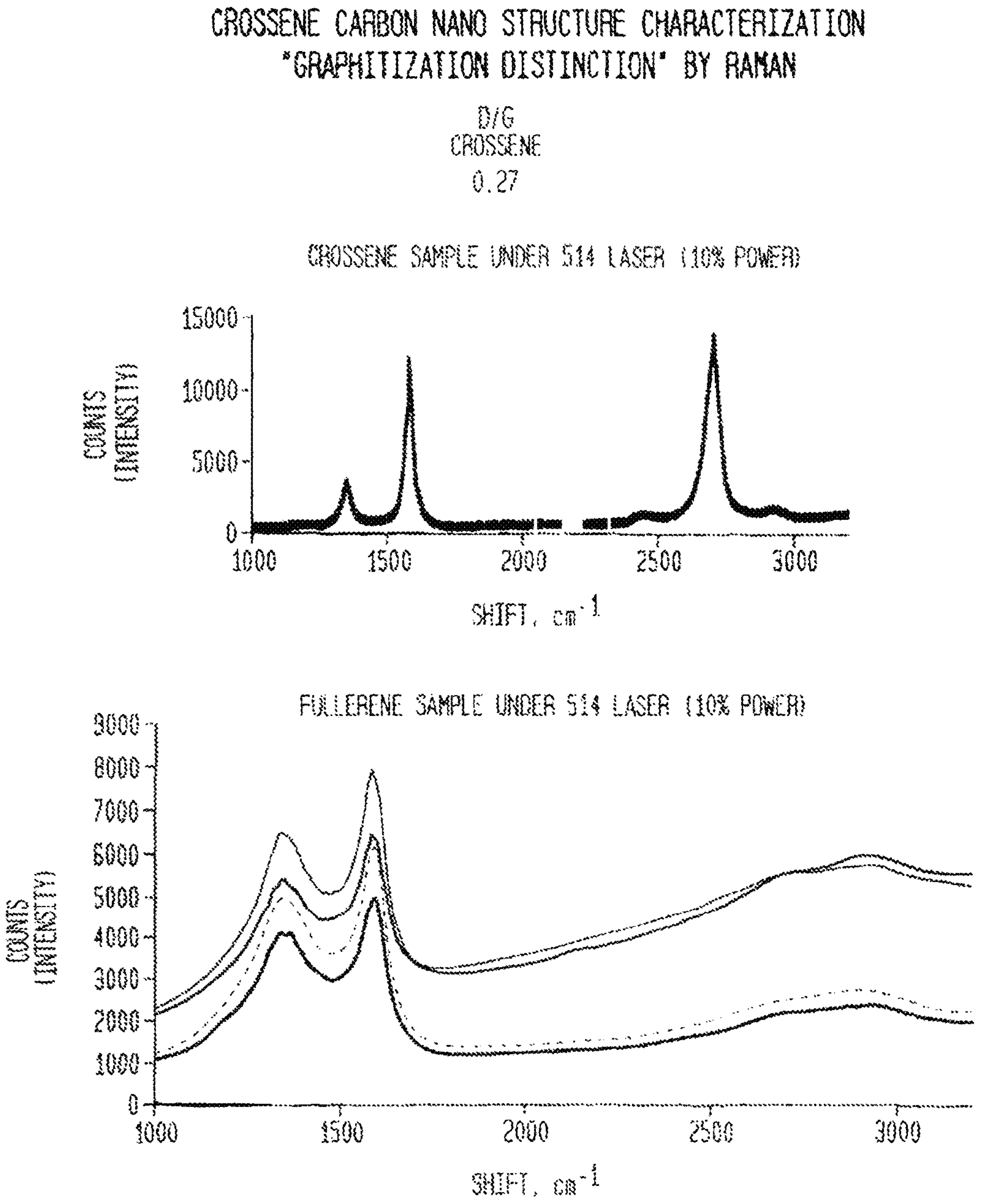
FIG. 2 presents Raman Spectra comparing crossene allotrope samples to fullerene allotrope sample.

A new allotrope of multilayered nanocarbon materials is herein introduced with an advanced bonding system of superior electron delocalization. Hitherto in the literature, the fullerene allotrope has been understood to encompass generally all trigonally bonded carbon systems of a curved nature and some would lump the planar nanocarbon graphene carbon materials into the fullerene category as well. Of particular focus of this disclosure is nanocarbon onions (NCOs) or carbon nano-onions (CNOs) or onion-like carbons (OLCs) wherein the systems possess a preponderance of generally complete continuous or cyclic layers without edges though some carbon nanotubes or graphenes with a high degree of multiple layers might harbor interest in regards to their possible relationship to this new allotrope, particularly if their edges could convert to a continuous cyclic system. The imprecise characterization of most all nanocarbons as being part of the fullerene family along with limitations of synthetic procedures of marginal yield and consistency in terms of numbers of layers and purity coupled to an unsophisticated consideration of the bonding involved to be like that of graphite or graphene has been a severe stumbling block in the progression of the development of the nanocarbon technology since its inception in 1985 by Smally, Curl and Kroto with the discovery of the first fullerene molecule routinely referred to as the C60 fullerene or Buckyball.

The new allotrope is formed through exposure of carbonaceous material, especially of multilayered nanocarbon materials particularly of the fullerene family, under carefully controlled residence times and temperature and pressure and atmospheric profiles compatible with what would be considered extreme conditions, generally above 2000° C. and optimally at 2600° C. to 2800° C. and above in annealing gases not necessarily restricted to inert gases like argon or nitrogen alone but optimally including small amounts of reactive gases as from the halogen family like chlorine. Such extreme conditions are required to convert the completed spherical layering with a central CG0 fullerene core or nucleus of the CNO fullerene to the new allotrope that no longer has a core but rather a hole or void generally between 3 and 9 nm depending on the degree of layering and therein generates stretches of planar carbon between points of curvature. Optimally the carbonaceous material precursor to the newly recognized allotrope is that of multilayered nanocarbon materials, particularly of the spherical fullerene family especially of relatively low surface area produced with low polydispersity in size and layering, high consistency, high reproducibility and high purity, without need for post-treatment with chemicals. Valued properties of the new allotrope are expected to improve dramatically with precursor CNOs of greater number of layers.

Due to the extreme conditions, the carbonaceous material undergoes a controlled disassembly and subsequent reassembly and rearrangement to a dramatically different bonding system of a far more thermodynamically stable allotrope. Spherical-like members, as opposed to incompletely continuous tubular or planar analogs bearing edges, possess a molecular formula of Cx where x ranges typically from about ten thousand to half a million and to two million to twenty million or more for more complex structures resulting from catenation for example.

Members of this new allotrope comprise multilayered nanocarbons that exhibit a dramatic difference in properties from members of the fullerene allotrope. Such properties, in part, are revealed in the realm of electrical conductivity, electromagnetic frequency (emf) reception/attenuation/transformation, and thermal and oxidative stability.

A whole new bonding structure, unaccommodatable by the simple fullerene concept of concentric layers of graphitic structures, connects one layer of this new allotrope to another in multilayered nanocarbon systems analogous to onions (CNOs or OLCs) or cylinders or tubes (MWNTs) but in a completely new arrangement in the array of carbons associated with the nanocarbon material. Multilayered or nested fullerene allotropic materials possess individual covalently connected molecular concentric layers or shells that have the possible prospects of rotating individually independent of one another upon overcoming the anticipated generalized attractive forces between the layers or shells generally interpreted loosely as van der Waal forces as with graphite that has a layer separation also of 0.34 nm. With nested fullerenes, however, there is also the added limitation to free rotation in a curved system due to a special interiorly oriented attraction or pull likened unto gravity or magnetism to the center of the first layer or the C60 core or nucleus. This special interaction between layers derives from the exterior low electron density of a lower layer or shell to the interior high electron density of the subsequent concentric layer or shell. Consequently, more extreme conditions are required for the conversion of fullerene CNOs with greater degrees of layering. There is simply a greater need for energy in exploding the fullerene system with layering all the way to the C60 core or nucleus into a crossene system bearing long multilayered stretches of general planarity and a hole or void three to nine times that of the volume of the 1 nm C60 fullerene core due to the ever greater thermodynamic stability with increases in layering.

Unlike the nested fullerene system, the new allotrope possesses a fixed arrangement or orientation of the inner shells with the outer shells held in place by the continuous multilayered system through points of curvature serving as a kind of window frame for holding the long stretches of planar areas in place in their optimal electron delocalization orientation between layers. The window frame is not in a generalized planar two-dimensional form customarily but routinely involves a ribbon-like structure that protrudes or worms into a three dimensional kind of ball array of multilayered trigonally bonded carbons. Accordingly, the new allotrope is one complete molecule without any movement or sliding between the layers or shells with respect to one another that is customarily facilely available with multilayered systems such as graphite.

Electron delocalization proceeds then in one perspective not only along individual layers or surfaces alone particularly in the long stretches of multilayered planarity as with aromatic-like systems like graphite but also through the points of curvature through the interiorly directed or focused fullerene-like electron delocalization. The other perspective for electron delocalization is not just along the layers or surfaces but throughout the whole single molecule of the new allotrope volumetrically or three-dimensionally across layers as well. This new allotrope therefore is separate from fullerenes through a continuity of bonding and electron delocalization extending beyond the dimension of just individual layers or surfaces within fullerenes to a new, three-dimensional crosslinking bonding network or array that supersedes the less inter-engaged fullerene layer system. This new understanding in allotrope bonding systems carries over to systems that are doped such as with silicon, boron, nitrogen, oxygen, sulfur and phosphorous introduced in any number of ways including carbon fragments, units or moieties involving heteroatoms.

This new allotrope is given the new name of "crossene" denoting its dramatic difference from a fullerene that takes into account the crossing of electron delocalization between layers as well as along layers. The crossene name also appears appropriate because it is a kind of cross between graphenic layers in the long stretches of plains of graphitic material that are held in place by fullerene-like points of curvature serving as a kind of window frame for planar panes of graphitic material. The orientation of the graphenic material in the long stretches of graphitic planes is expected to be held rigidly in place in a "AAA . . . " stacking arrangement for the optimal overlap of six-membered rings for achieving a kind of charge-transfer complex orientation that allows of the hopping of electrons between layers leading to the remarkable electron delocalization seen in crossenes responsible for achieving exceptional thermodynamic stability. Such unique volumetric delocalization thereby distinguishes crossenes from the far lower degree of electron delocalization of fullerenes and thereby accounts for exceptional degree of electron conductivity or emf attenuation for crossenes versus the corresponding multilayered fullerene allotrope.

This dramatic difference between the two allotropes is confirmed by a dramatically differently appearing Raman spectroscopy analysis where the GG or G' peak dominates for the crossene allotrope while it is hardly noticeable with the fullerene allotrope. The crossene allotrope is also differentiated from the fullerene allotrope because of its exceptional thermodynamic stability exhibited in TGA (thermogravimetric analysis) versus that of the fullerene allotrope. In effect, the crossene allotrope is a special kind of multilayered graphene without edges forced into a stacking orientation that accentuates and multiplies electron conductivity and emf attenuation properties along with thermodynamic stability without toxicological concerns of the customary edges found in graphite and carbon nanotubes (CNTs) for example.

The C60 fullerene is prominent in intergalactic space and has been so for eons and was only recognized in 1985 by Smalley, Curl and Kroto. Only after their discovery of fullerenes, for which they were awarded the Nobel Prize, has the international nearly trillion dollar race been underway for further discovery, synthesis procedure development leading to eventual industrial production, modification techniques and application targets.

Fullerenes have unknowingly been pursued since the days of Peter the Great of Russia who had recognized the healthful attributes of shungite, a mineral discovered near the city of Shunga' near St. Petersburg. This mineral site continues to serve as a spa of sorts since the days of Peter the Great. Also, especially since the 1985 discovery of C60 fullerene (Buckyball), the mineral of a mixture of many components is mined for export especially after it was revealed that it possessed fullerene components that recently were shown through C60 fullerene to have potential health benefits through initially designed toxicity testing in France on mice.

Since the discovery of fullerenes and subsequently carbon nano-onions (CNOs) or nanocarbon onions (NCOs) or onion-like carbons (OLCs), there was no recognition made of this new crossene allotrope. This lapse persisted despite the discovery of the formation of so-called polyhedron nanocarbon material that was treated largely as a morphological curiosity with occasionally some recognition of some improvement of properties almost exclusively by spectroscopic examination as through Raman spectroscopy involving generally materials of relatively low layer number and low purity where both can conceal the true exceptional nature of the polyhedron curiosity where layering three times in number provides recognition far more dramatically which provides the basis of this patent declaring the new allotrope of crossene.

With almost 50 reported different synthetic routes to carbon nano-onions (CNOs), all of which involved uncontrolled reactions thus providing different carbon nano-onion material with each preparation in terms of the degree of layering, defects, catenation, polydispersity and side-reaction components, CNOs have received hardly any attention next to carbon nanotubes (CNTs) and graphene. Accordingly this new allotrope of carbon has been overlooked. With recent access to an abundance of CNOs of high consistency in layer count and minimum of defects in high purity and of low polydispersity with essentially no side-reaction products, research into CNOs has proceeded well of late with now the announcement of a highly valuable new allotrope of crossene that is the most thermodynamically stable of the carbon allotropes next to fullerene and then graphite and graphene and finally diamond.

The reality of the differences between fullerenes and crossenes is demonstrated in the data provided in the Figures and related description. Accordingly properties and potential applications of this new allotrope exhibit a dramatic difference from fullerene allotropic materials due to a new bonding system resulting in differentiation in electron delocalization. This new kind of electron delocalization manifests itself in differently appearing Raman spectra of intensified G peaks and substantial GG or G' peaks in great contrast to Raman spectra for simple fullerenes. In alignment with the given name for this new allotrope, one can consider the cross-over of pi-electron-like bonding between layers as a kind of cross-linking strengthening of the system that is borne out by its increase in thermogravimetric stability data. The crossene allotrope provides molecules of far greater thermodynamic stability than those of the fullerene allotrope family.

Discovery of the so-called "buckyball" or C60 fullerene molecule was facilitated due to its volatility upon intensive heating originally of a graphite anode wherein it was released under vacuum into a mass spectrometric vacuum chamber for analysis to display the telltale registered molecular weight of 720 a.m.u. The C60 fullerene subsequently was isolable and purifiable, particularly through High Pressure Liquid Chromatography (HPLC) due to its exhibited solubility as well.

The formation of crossenes has had no such advantages, being neither volatile nor soluble in the traditional sense. Only by way of a new synthetic procedure for generating selectively certain nanocarbon materials of exceptionally high multilayered nature, conversion, yield, consistency and purity could the new carbon allotrope's existence be discerned and thus recognized and reported finally as discovered. The foundation of this discovery is presented below based particularly upon the following characterization observables: thermodynamic stability, BET surface area, Raman spectroscopy, X-Ray diffraction evaluation, electrical conductivity, electromagnetic frequency (emf) attenuation, and scanning and transmission electron micrographs.

I. Crossene Characterization

A. Thermodynamic Stability

FIG. 1A presents a comparison of thermogravimetric analytical (TGA) data for a crossene allotrope versus a fullerene allotrope in the upper portion of the figure and the lower portion respectively.

First and most dramatically the difference in thermodynamic stability of crossenes is plainly seen from its degree of combustion or oxidation resistance to an oxygen bearing gas at temperatures up to even 800° C. (See the upper portion of FIG. 1), well beyond the range of other graphitic structures like graphite or fullerenes whose resistance is rarely observed to proceed beyond 500° C. (See the lower portion of FIG. 1). The significantly enhanced thermodynamic stability would be expected to correlate to the level of electron delocalization of a crossene in comparison to a fullerene. The crossene's delocalization is not restricted to the individual nested fullerene layers of a multilayered nanocarbon system but involves the whole three dimensional system of the crossene molecule.

B. BET Surface Analysis

Surface areas for crossene samples according to Brunauer-Emmett-Teller (BET) methods have routinely registered below 100 square meters per gram and more generally between 30 and 50 square meters per gram.

C. Raman Spectroscopy

Raman spectroscopy has long been applied to fullerenes for distinguishing the degree of what is termed graphitization or electron delocalization between samples. Comparing the two sets of spectra performed on different spots of a crossene sample and a fullerene sample in FIG. 2, one sees a stark contrast between the Raman spectra of the crossene allotrope in the upper portion of the figure versus the fullerene allotrope of the lower portion of the figure, especially in the sharpness of the G ("graphitic") signal and in the observation of a very strong and sharp GG signal that is hardly detectable at all in the midst of the signal noise with the fullerene allotrope. Such distinctions agree with at least an order and most likely several orders of magnitude difference in electron delocalization for crossenes versus fullerenes [See Section E on the conductivity/resistivity measurements]. Using a Raman Renishaw Spectrometer employing a 514 nm laser at 10% power, a modest D peak occurs at roughly 1350 $cm^{-1}$ whereas the strong major G and GG peaks occur at 1575-1600 $cm^{-1}$ and 2695-2700 $cm^{-1}$ respectively.

D. X-Ray Diffraction

Figure 3:
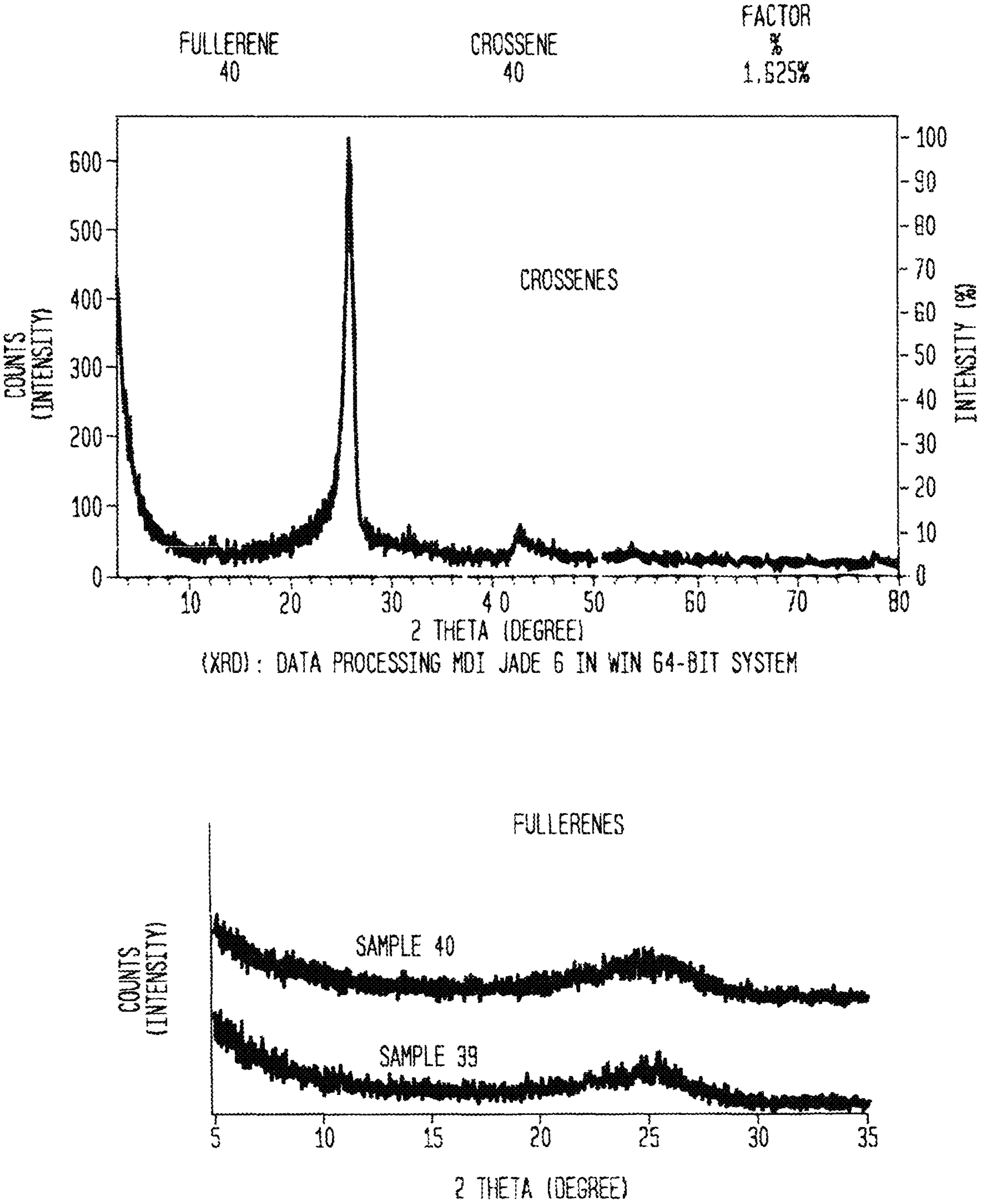
FIG. 3 presents an X-Ray Diffraction Pattern comparison of a crossene allotrope sample to a fullerene allotrope sample.

FIG. 3 corroborates the accentuated difference in the degree of delocalization demonstrated by way of Raman Spectroscopy in comparing a crossene allotrope in the upper portion of FIG. 3 to a fullerene allotrope in the lower portion of FIG. 3. See "*Dependence of graphitic order of carbon nanostructures on AC and DC arc discharge methods and Ni content in thin electrode*" C. R. JANG*, Gr. RUXANDA, M. STANCU, V. VOICU, D. CIUPARU** *Petroleum—Gas University of Ploieşti, Bd. Bucureşti* 39, 100680, Ploieşti, Romania, *OPTOELECTRONICS AND ADVANCED MATERIALS—RAPID COMMUNICATIONS* Vol. 6, No. 1-2, January-February 2012, p. 62-67 [file:///C:/Users/owner/Downloads/14Jang.pdf].

E. Electrical Conductivity

The degree of electron conductivity in the respective allotropes correlates to the degree of electron delocalization. When the whole system of delocalized electrons is a single molecule or three-dimensional or volumetric array of carbons as in crossenes, delocalization as reflected in thermodynamic and electrical conductivity is immensely superior to delocalization restricted to surface-only electron delocalization for the individual fullerene shells in multilayered nested fullerenes as with CNOs, OLCs or MWCTs. The dramatic difference in electrical conductivity and thermal stability is then readily understood between crossene and fullerene systems.

Figure 4:
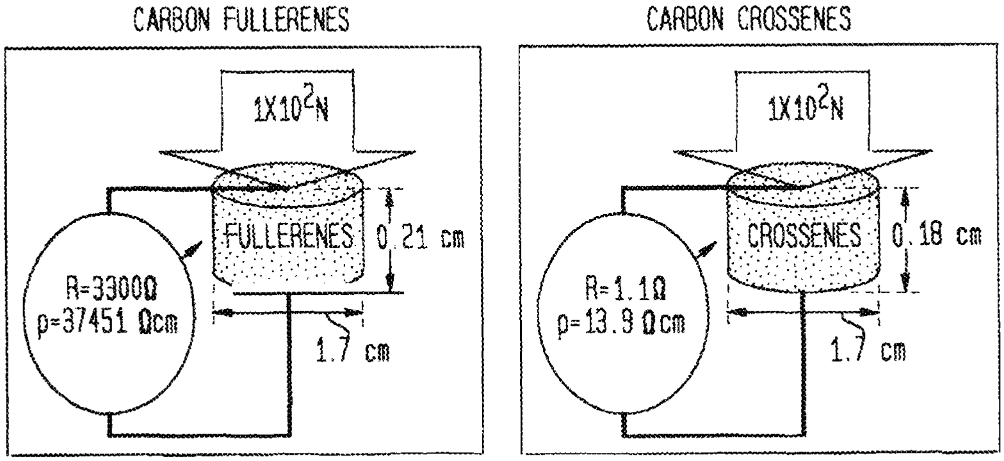
FIG. 4 presents electrical resistance data comparing a crossene allotrope to a fullerene allotrope.

Just as the extent of electron delocalization determines the thermodynamic stability of the crossene allotrope over the fullerene allotrope (as well the stark contrast in the Raman spectra of the crossene allotrope over the fullerene allotrope), the unique electron delocalization of crossenes over fullerenes translates into an enhanced degree of electron conductivity capability of the crossene allotrope over the fullerene allotrope. FIG. 4 presents corresponding resistivity data of a crossene allotrope sample versus that of a fullerene allotrope sample. The calculated resistivity determined that the fullerene allotrope is much less conductive than the crossene allotrope by several orders of magnitude. The electrical resistivity test was conducted by compressing the Carbon powders into a pellet by a specially designed mold (cylinder with 2 pistons) set up with a constant compressing pressure. The resistance R of the Carbon Fullerene pellets was measured by a multimeter at room temperature with air humidity of 25%. The resistivity p was calculated based on the dimensions (diameter and height) of the cylindrical samples and the measured resistance using the Ohm's law. The calculated resistivity revealed that the Carbon Fullerene sample is much less conductive than the Carbon Crossenes.

F. Electromagnetic Frequency Attenuation

Another facet relating to electron delocalization is an extraordinary electromagnetic frequency (emf) attenuation effect. Such effect is observed for the fullerene allotrope especially of a multilayered or multiwalled nature such as the fullerene allotrope shown at different magnifications in FIGS. 5C and 5D. The effect is dramatically accentuated for the crossene allotrope by simple comparison of the fullerene allotrope of FIGS. 5C and SD versus the crossene allotrope of FIGS. 5E and 5G in a household microwave oven. Both allotropes exhibit a metallic like sparking with the emission of light of a whole range of electromagnetic radiation appearing as a bright light along with thermal stimulation of the surrounding environment in just seconds as in the plate upon which the sample is placed upon exposure. Crossene samples, however, show a sharp contrast to that of fullerene samples in being blindingly bright white as compared generally to a subdued orangish light of fullerene samples. Correspondingly, the plate on which the sample is situated is heated up far more aggressively for crossene samples as opposed to fullerene samples where exposure of less than a second for a crossene sample far outmatches the thermal effect of the same exposure to a fullerene sample for over ten seconds.

G Scanning and Transmission Electron Micrographs

Figure 5A:
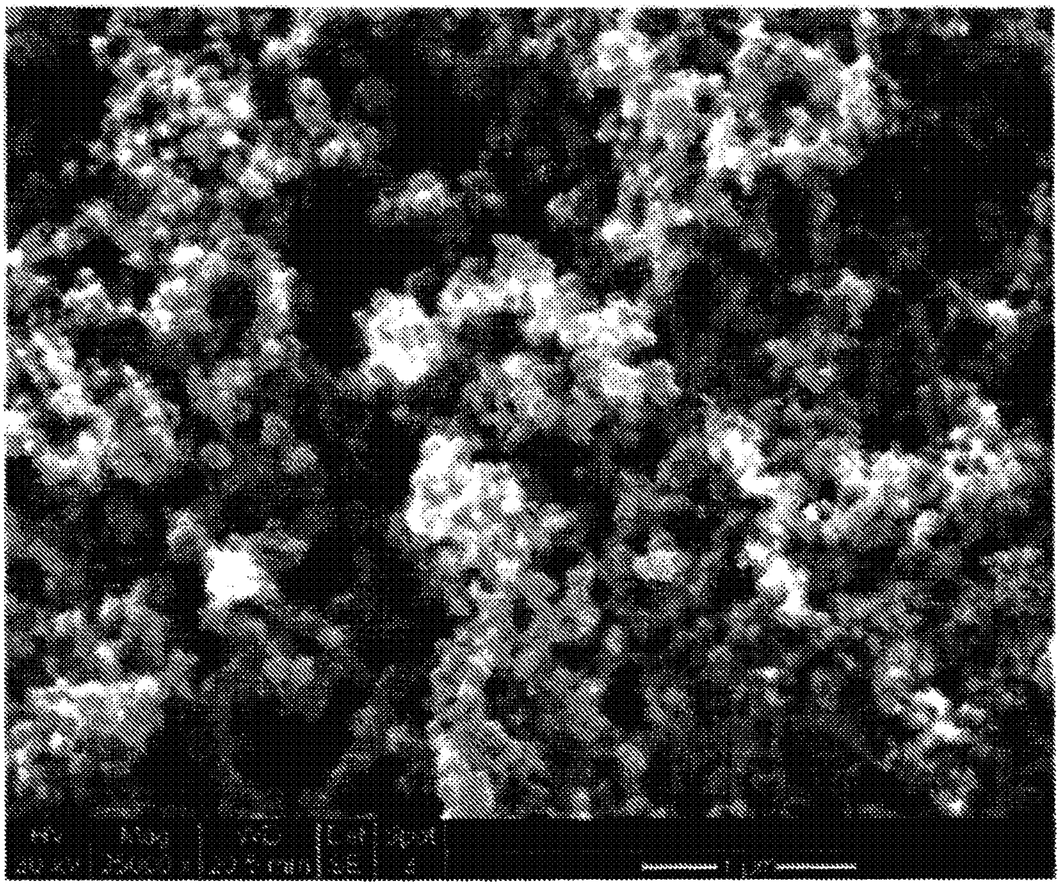
FIG. 5A presents scanning electron micrograph (SEM) observations of a fullerene structure modified by catenation at 2500×.
Figure 5B:
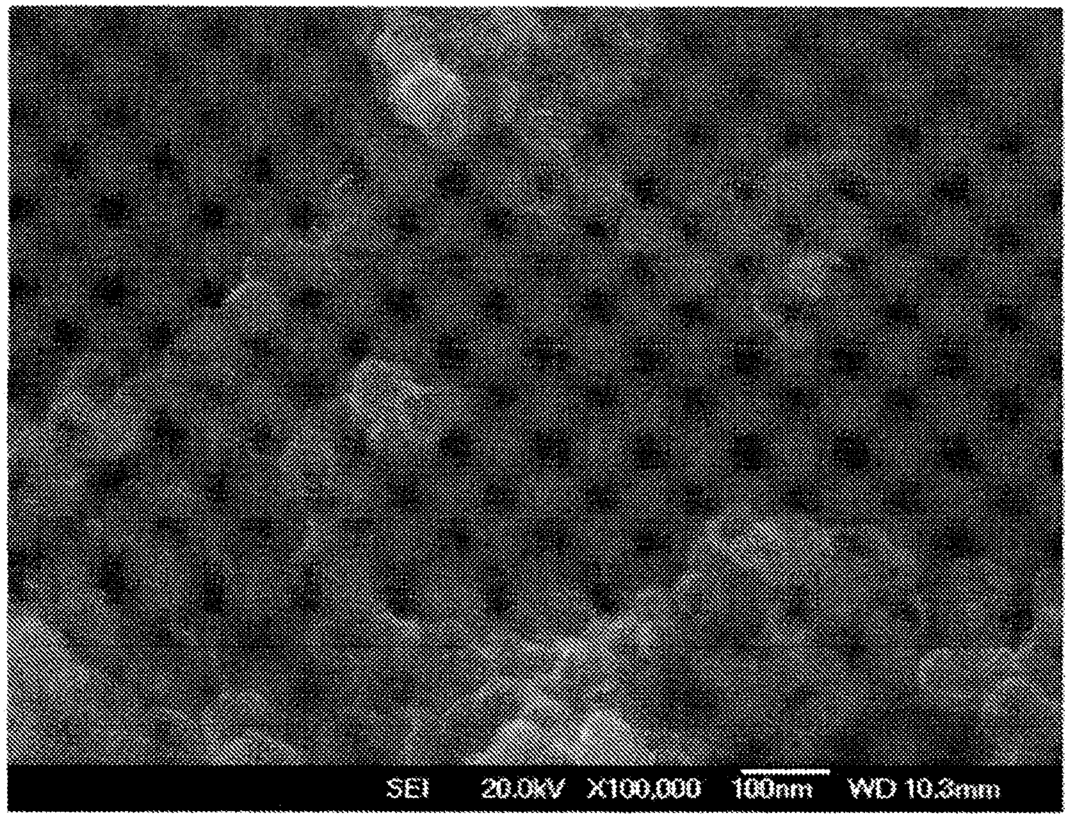
FIG. 5B presents scanning electron micrograph (SEM) observations of a fullerene structure modified by catenation at 100,000×.
Figure 5C:
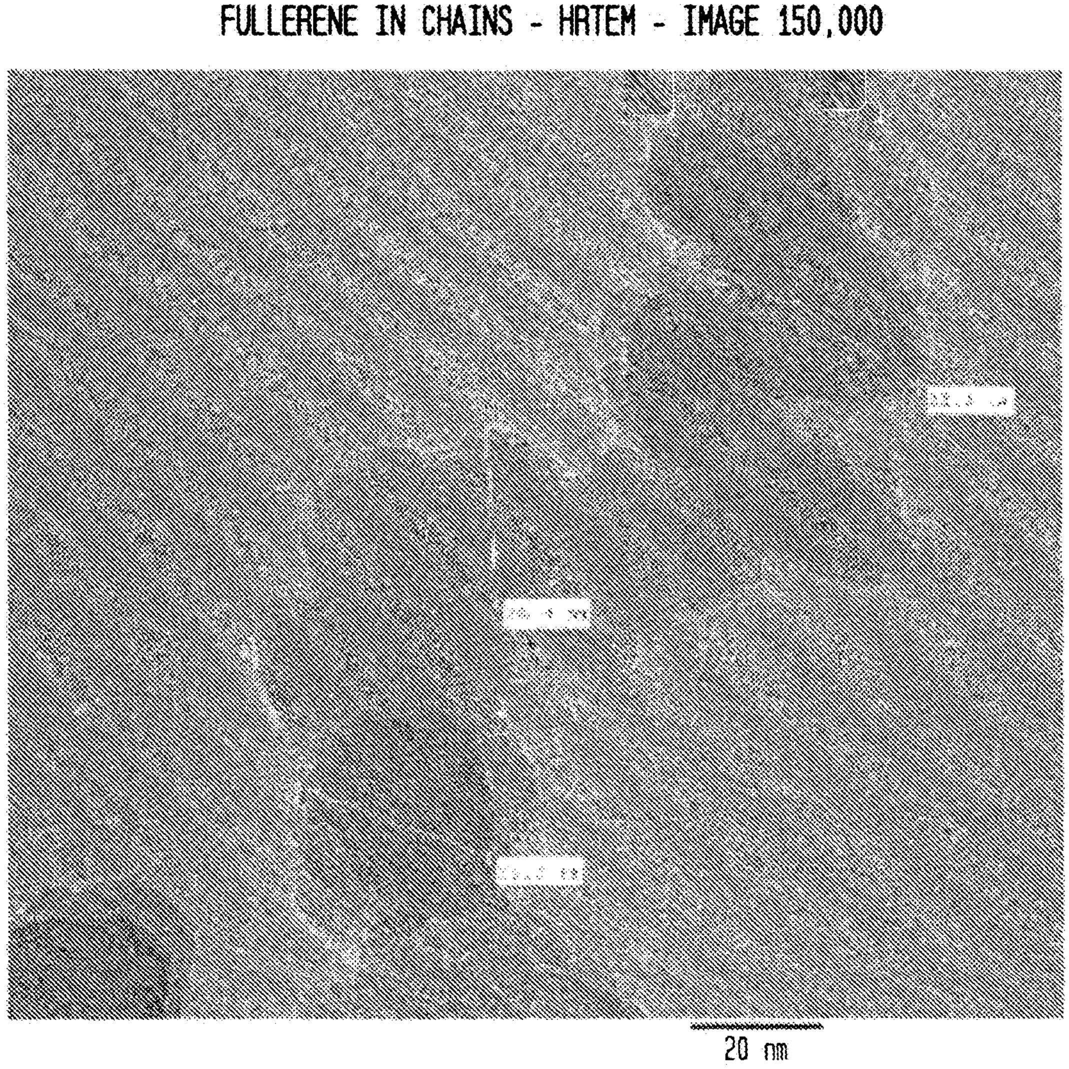
FIG. 5C presents high resolution transmission electron micrograph (HRTEM) observations of a fullerene structure modified by catenation at 150,000×.
Figure 5D:
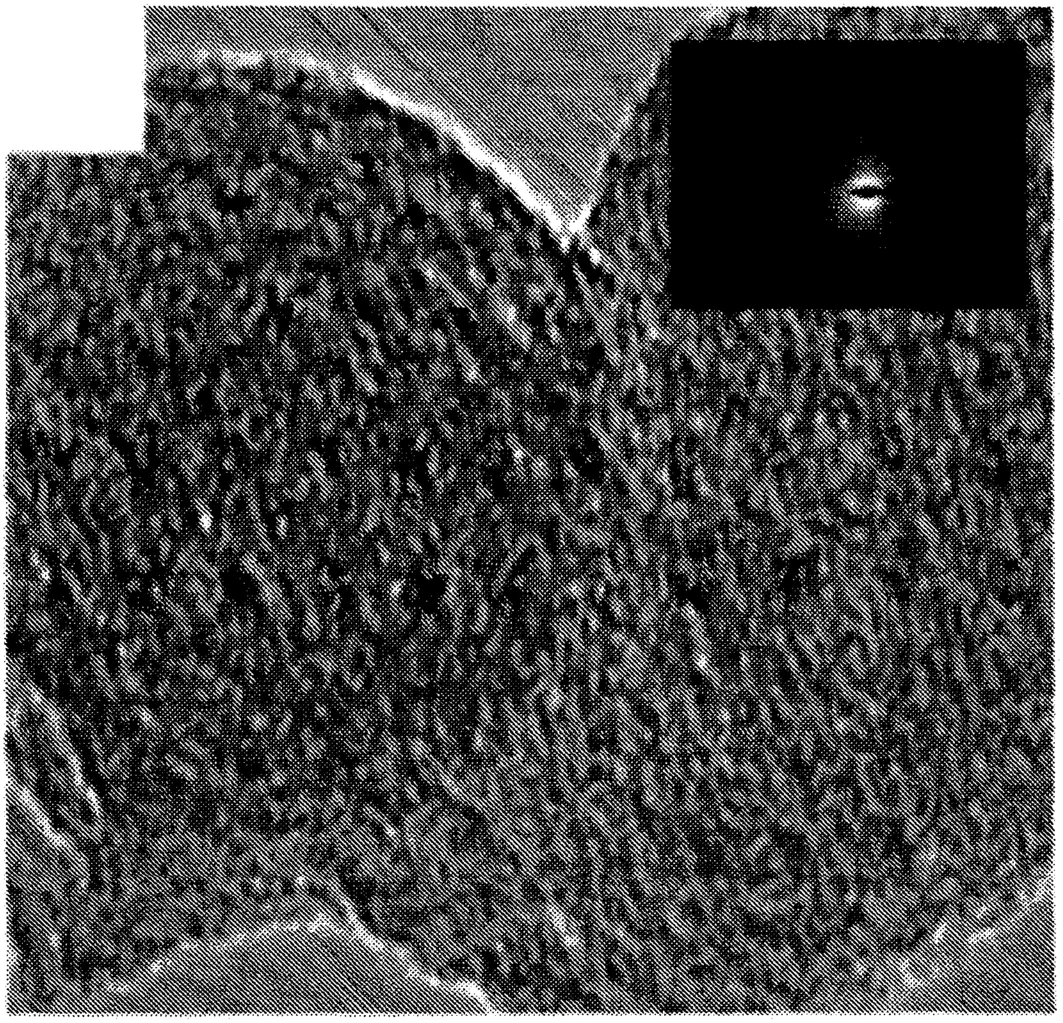
FIG. 5D presents high resolution transmission electron micrograph (HRTEM) observations of a fullerene structure modified by catenation at 500,000×.
Figure 5E:
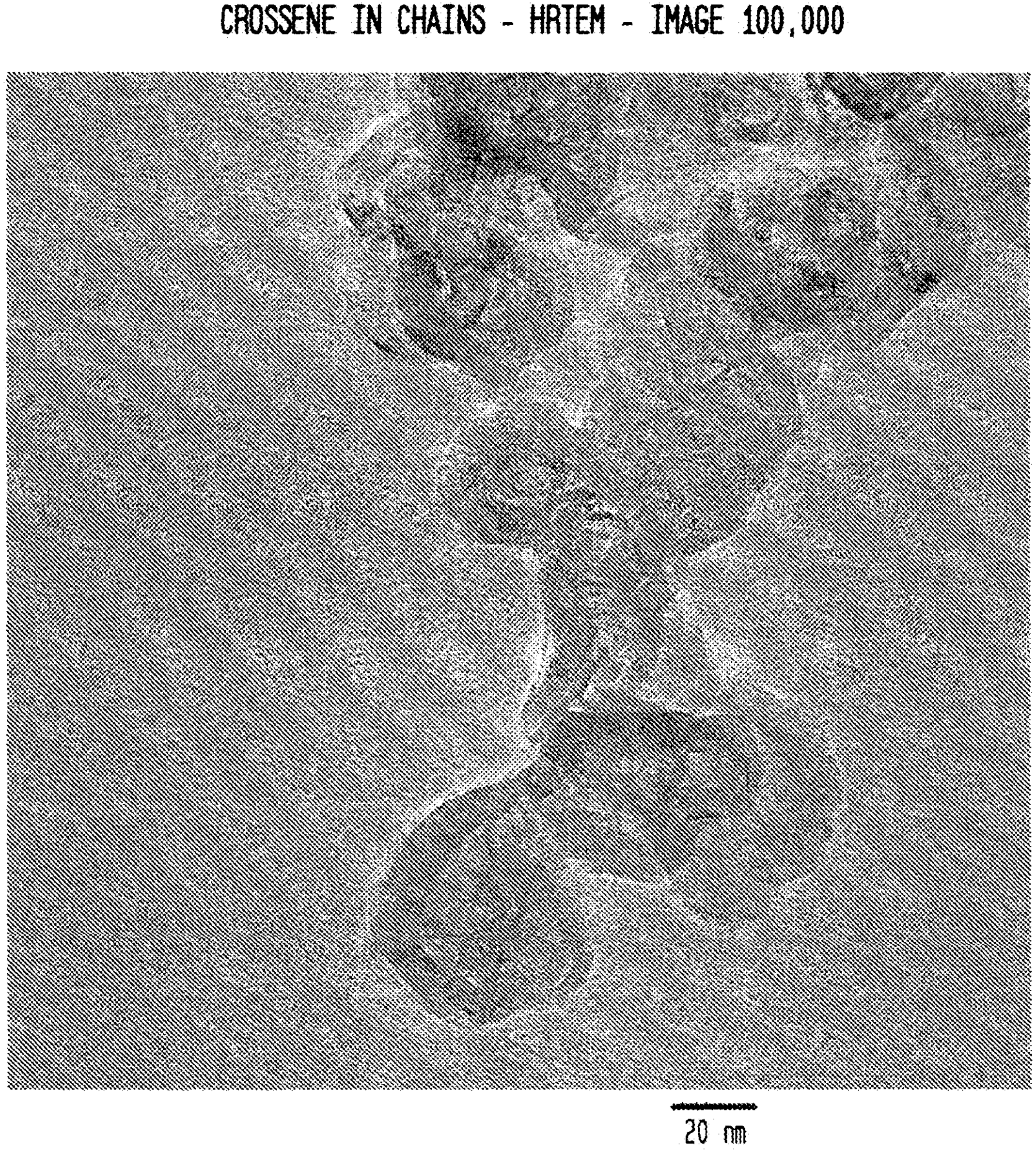
FIG. 5E presents high resolution transmission electron micrograph (HRTEM) observations of a crossene structure modified by catenation at 100,000×.
Figure 5F:
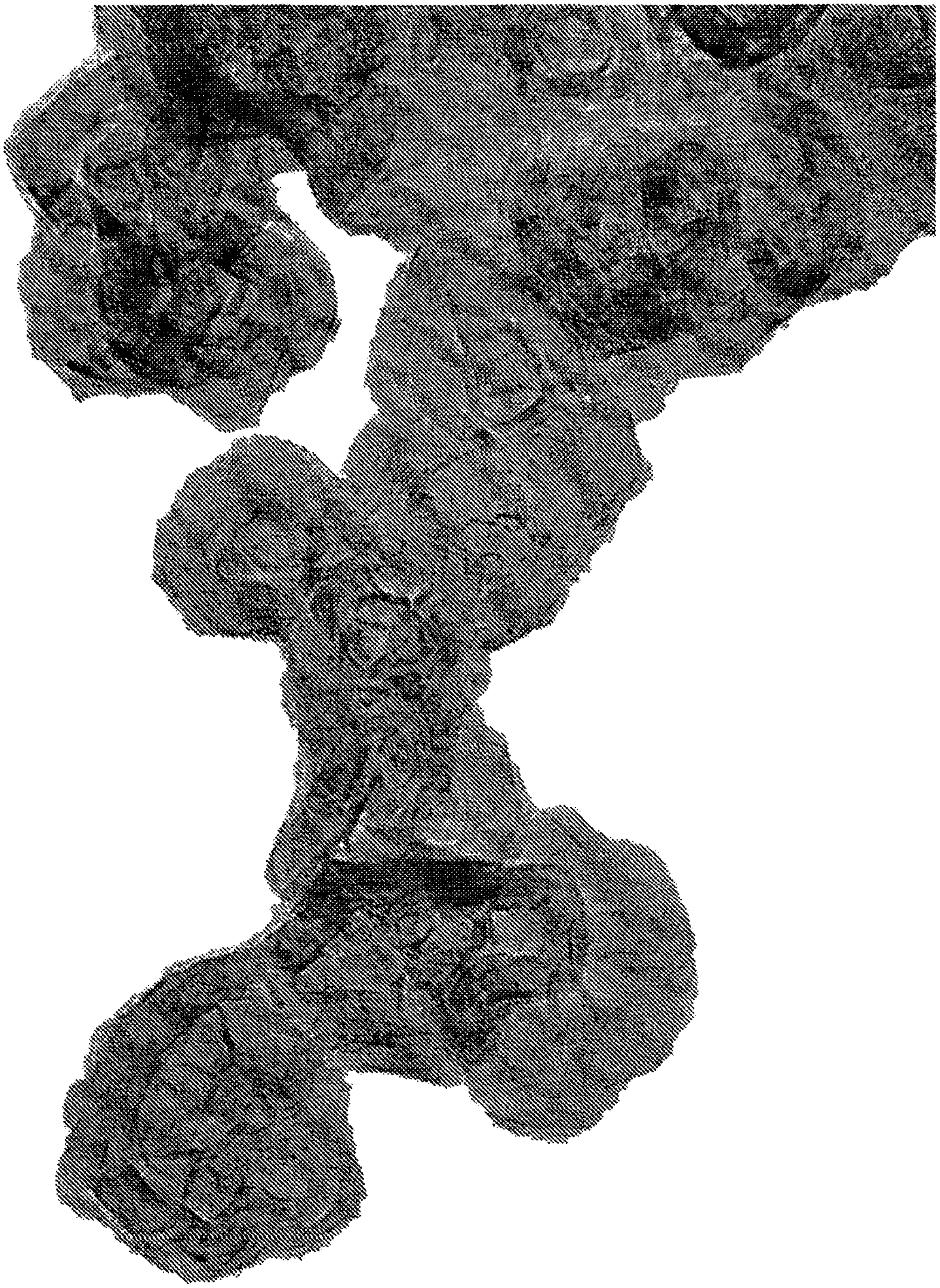
FIG. 5F presents high resolution transmission electron micrograph of the crossene structure of FIG. 5E with a contrasting background.
Figure 5G:
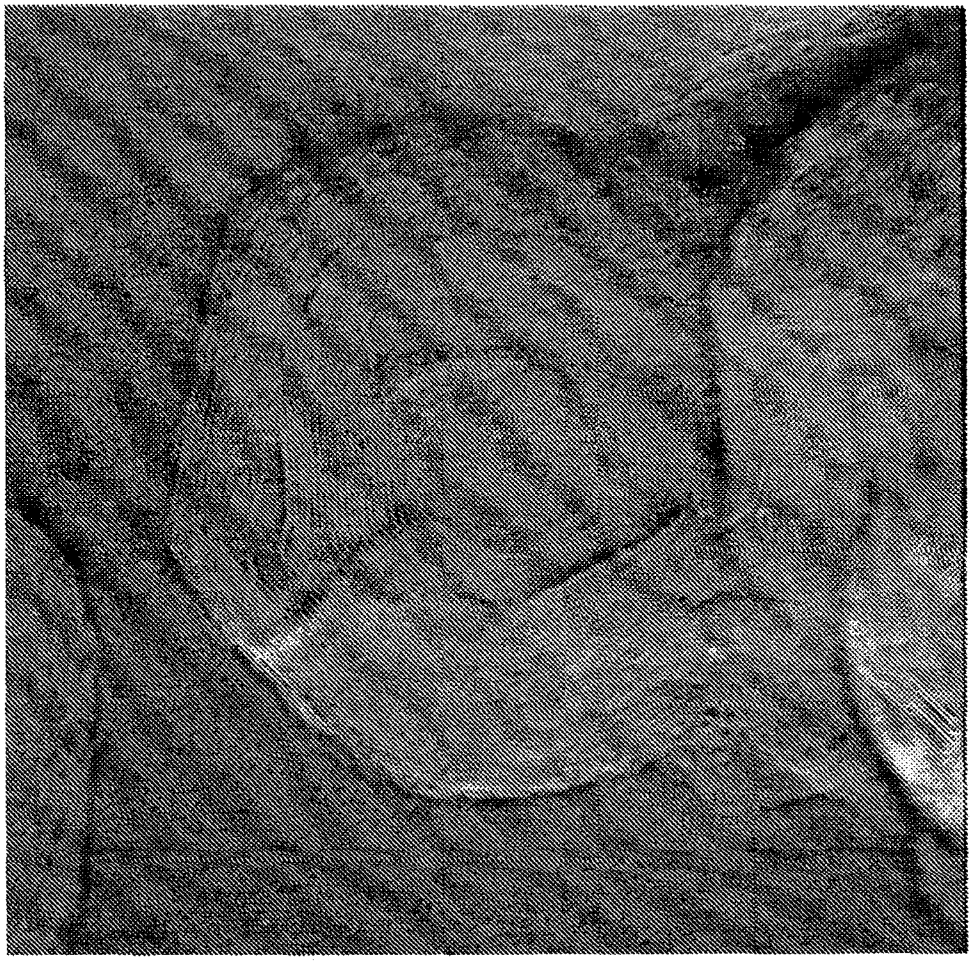
FIG. 5G presents high resolution transmission electron micrograph (HRTEM) observations of a crossene structure modified by catenation at 500,000×.
Figure 5H:
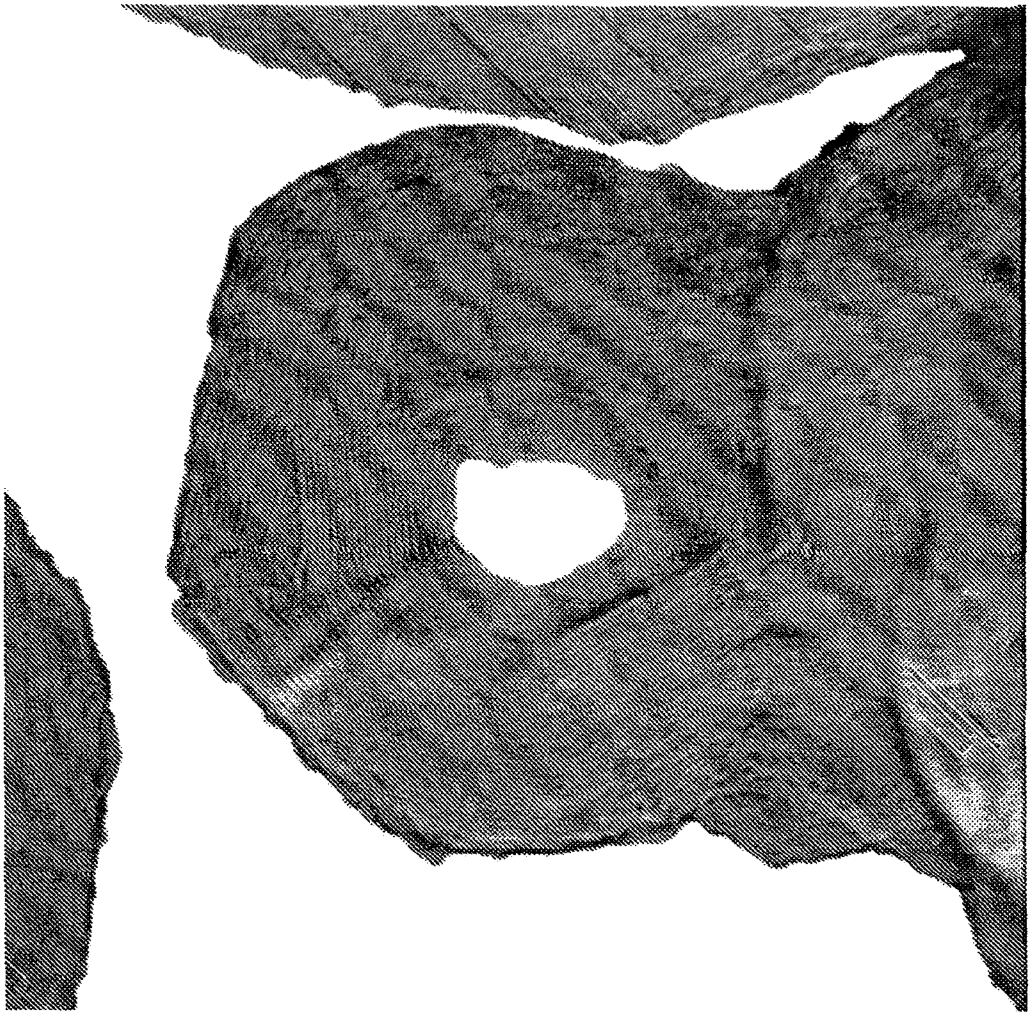
FIG. 5H presents high resolution transmission electron micrograph of the crossene structure of FIG. 5G with a contrasting background.

Micrograph comparisons are provided between samples of crossene and CNO fullerene of similar nature with both having a catenated structure. FIGS. 5A and 5B present fullerene SEM images at 25,000 and 100,000 magnification respectively. FIGS. 5C and 5D present fullerene HRTEM images at 150,000 and 500,000 magnification respectively. FIGS. 5E-5F and 5G-5H present crossene HRTEM images at 100,000 and 500,000 respectively. The catenated structure is apparent in the images of lower magnification while the high magnification images of FIG. 5D and FIG. 5G-5H reveal the drastic difference between the concentrically three-dimensional spherical CNO fullerene and the ribbon-like crossene with planar stretches surrounding a hole or void of varying dimensions and shapes and sizes where the layers are clearly visible and countable apart from overlapping crossene units in the catenated chain. With the high resolution images of fullerenes and crossenes, voids or holes of disparate sizes and shapes provides a dramatic differentiation between the fullerene allotrope and the crossene allotrope. The FIGS. 5E and 5G are the original micrographs for which FIGS. 5F and 5H are adjusted for improved contrast removing background material with a white background.

It is the requirement of extreme conditions that allows the conversion of a fullerene precursor with presumably a C60 core or nucleus to disassemble from its exceptionally thermodynamically stable status far greater than that of a C60 fullerene alone to reassemble to a yet dramatically more thermodynamically stable crossene with a far greater degree of delocalization not only associated with a particular layer but additionally across layers held in place through the continuous cyclic nature of the nano structure as a kind of window frame for optimizing electron delocalization across layers. The two distinct allotropes have up to now been lumped together mistakenly as different types of fullerene carbon nano-onions (CNOs). See Tomita, S.; Sakurai, T.; Ohta, H.; Fujii, M.; Hayashi, S. *J. Chem. Phys.* 2001, 114, 7477-7482. doi: 1.0.1063/1.13601.97.

II. Potential Crossene Surface Modifications

Known and presented in a recent review article (Bartelmess J, Giordani S. *Carbon nano-onions (multi-layer fullerenes): Chemistry and applications. Beilstein J. Nanotechnol.* 2014; 5:1980-8; doi: 10.3762/bjnano.5.207) is that C60 fullerene and fullerene onions have a reactive outer surface amenable to all manner of modification or, in nanocarbon-specific verbiage, of decoration that translates into all manner of means of functionalizing the surface for particular purposes and applications. Incidentally, as with the foregoing footnote, in the 2014 year of this review publication, what is now known as the crossene allotrope was identified as a fullerene "polyhedron onion."

Though the exterior surface reactivity would be expected to be dramatically reduced from that of fullerenes, functionalization is expected to be achieved to some extent, especially at the points of curvature of the confining "window frame." Additionally, functionalization may be first established in a fullerene CNO that may persist to some extent for certain functional groups following the conversion under extreme conditions to the crossene. Functionalization may be generated in a wide variety of known techniques including, but not limited to, 1,3 dipolar additions and other cycloadditions including carbene reactions, radical additions, halogenations, sulfonations, amidations, alkylations, and redox procedures.

Chemical modification may be applied to the outer surface to create a variety of different organic chemical functional groups to modify properties for rendering said carbon nanostructures amenable to various applications benefitting from the incorporation of organic functional groups for objectives in, but not limited to, adjusting solubilities in a variety of different solvents and compatibilities in polymerizations and solubilizations thereof in different media or in attachments of specialized agents useful, but not limited, to biological and medical applications, and also in enhancing prominent properties as in composite strengthening, electrical conductivity/storage, emf attenuation/reception, emf thermal stimulation, radiation curing enhancement, thermal insulation, biotechnology, biomedicine, preventive medicine, tribology, hydrophobicity, magnetism applications among others in regard to particular properties required for varied and diverse applications.

Functionalization may proceed of the outer surface for example through potassium hydroxide or oxidation treatments as in treatment involving nitric acid, through addition or cycloaddition reactions, through simple fluoride or halogen addition reactions, through free radical addition reactions for preparing the nanoparticles for further functionalization as in sulfonation, and other means. See Bhinge S D. *Carbon nano-onions—An overview. J Pharm Chem Chem Sci.* 2017; 1 (1): 1-2. *J Pharm Chem Chem Sci* 2017 Volume 1 Issue 1 [Editorial], Accepted on Oct. 13, 2017 http://www.alliedacademies.org/journal-pharmaceutical-chemistry-chemical-science/.

III. Potential Crossene Applications

As can be readily seen from the Characterization and Modification sections, crossenes offer a wide range of applications regarding, but not limited to material science, metallurgical modifications as with alloy improvements with replacement of traditional carbon components and also covetics, aerospace, solar energy, 3D printing, polymers and plastics, polymer or plastic or inorganic composites or matrices, emf thermoset plastic curing, paints and coatings, oxidation/combustion resistance application, glass treatments, thermal insulation, electronics, electrical transmission, batteries or capacitors, emf attenuation/reception, catalysis, tribology, optical limiting, water resistance, cancer and dermatological treatments, preventive medicine, biological ablation therapy, emf-therapy, radiation protection, radiological contrasting agents including other bioimaging technologies, drug or gene agent delivery, toxin and heavy metal removal, and other biotechnology innovations.

Applications regarding material science, include, for example, engagement with polymer, plastic and/or inorganic composites or matrices and also thermoset formulations thereof as applied to, but not limited to the aerospace, 3D printing, electronics, construction/rehabilitation industries.

Applications regarding thermal insulation properties include, for example, refrigeration, clothing, housing, vehicles, shipping, aerospace, transportation, communication, industrial processes, electronics, paints and coatings, glass treatments, beverage and food service through the appropriate blending of the nanoparticles into the materials of interest directly or into the associated materials that render the thermal insulation properties.

Applications regarding electrical conductivity/storage properties include, for example, electrical conductivity/storage properties applied, but not limited, to electrical transmission, wiring, electronics, electrically motorized or hybrid vehicles, electrical motors, aerospace, mass transport, batteries and capacitors through incorporation of the nanoparticles into the appropriate carrier materials.

Applications regarding emf attenuation/reception properties include, for example, Faraday cage protection of people and electronics as in plastics, coatings, paints, clothing, electronic device sheaths regarding wifi and smart meter protective devices in homes and vehicles and electronics from electromagnetic pulses in regards to cell phones, computers, automobile computers wherein the nanoparticles are blended into the materials of interest directly or into the associated materials that render the electromagnetic attenuation protection.

Applications regarding emf attenuation/reception properties include, for example, microwave oven use as in susceptor pads as in replacement of metal foil alternatives and to radiation-induced warming capability in clothing and/or equipment where especially high solar radiation is available in the midst of frigid temperatures.

Applications regarding emf attenuation/reception properties include, for example, enhancement of electromagnetic transmission reception equipment or techniques.

Applications regarding electromagnetic radiation attenuation/reception properties include, for example, thermal stimulation in a multitude of ways particularly for use in polymers, plastics, paints, coatings and adhesives or solders for curing purposes by blending the nanoparticles into the materials of interest directly or into the associated materials that render the thermal stimulation properties.

Applications regarding tribological and/or thermal insulation properties include, for example, motor oils, lubes, cookware, associated coatings by blending the nanoparticles into the materials of interest directly or into the associated materials that render the tribological properties.

Applications regarding hydrophobicity properties include, for example, water resistance applications as in window and windshield fog elimination, weather-resistant material and clothing, biotechnological and biomedical pursuits, biomaterial encapsulation by blending the nanoparticles into the materials of interest directly or into the associated materials that render water-resistant properties.

Applications regarding biotechnological and/or biomedical and/or preventive medicine utilization properties include, for example, selective tumor ablation due to radiation attenuation/thermal stimulation properties upon local administration of the nanoparticles followed by the application of highly directed microwave probes, antioxidant or photonic modulation effects for maintenance of living organism damage control effects by oral or injection nanoparticle procedures including use in acupuncture and related therapeutic regimens and also application topically especially for dermatological disorders including, but not limited to, moles and wounds.

Applications regarding biotechnological and/or biomedical utilization applied, but not limited, to bone scaffolding properties include, for example, 3D printing technology, x-ray or MRI contrasting agents, drug or gene delivery, and heavy metal removal.

Applications include, for example, material science, metallurgical modifications as with alloy improvements through replacement of traditional carbon components.

Applications include covetic alloy products produced in numerous manners generally during the production of nanocarbon materials.

Applications include use of crossene thermal stability properties for allowing these materials' utilization under high temperature conditions.

Applications include use of crossene thermal stability properties in biological studies where unconverted nanomaterial would survive combustion removal of biological matter for the purposes of tracking delivery of nanocarbon materials in biological systems.

Applications include use of any magnetic properties in biological systems as in specifically targeted therapy and bioimagery and other magnetism important applications.

Applications include use of crossene electromagnetic attenuation properties in regards to energy production especially in regards to solar energy issues.

The present invention includes item 1) a carbon allotrope bearing a multilayered three-dimensional nanocarbon array, wherein stabilizing electron delocalization crosses between layers in an advanced interlayer connectivity bonding system involving the whole carbon array; item 2) a carbon allotrope bearing a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon allotrope; and item 3) a carbon allotrope bearing a multilayered three-dimensional nanocarbon array, wherein stabilizing electron delocalization crosses between layers in an advanced interlayer connectivity bonding system involving the whole carbon array, wherein the carbon allotrope has exceptional properties in the realm.

The present invention further includes item 4) a carbon material, comprising a multilayered three-dimensional nanocarbon array, wherein stabilizing electron delocalization crosses between layers in an advanced interlayer connectivity bonding system involving the whole carbon array; item 5) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array; item 6) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array, wherein the nanocarbon material has exceptional properties in the realm; item 7) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array, wherein the nanocarbon material has exceptional properties in the realm, wherein the nanocarbon material is derived from a carbon material produced from a process that has insignificant amounts of adverse side reaction contaminants otherwise requiring chemicals for purification; item 8) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array, wherein the nanocarbon material has exceptional properties in the realm, wherein the carbon material from which the nanomaterial of item 6) is derived has a multilayered generally spherical or quasi-spherical form; item 9) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array, wherein the nanocarbon material has exceptional properties in the realm, wherein the carbon material from which the nanomaterial of item 6) is derived and has a surface area below 100 square meters per gram as established by Brunauer-Emmett-Teller (BET) methods; and item 10) a carbon material, comprising a multilayered three-dimensional nanocarbon array, wherein stabilizing electron delocalization crosses between layers in an advanced interlayer connectivity bonding system involving the whole carbon array, wherein the electron delocalization proceeds between layers or surfaces and throughout the whole network of carbons in multiple directions in the carbon array, wherein the nanocarbon material has exceptional properties in the realm, and wherein the carbon material from which the nanomaterial of item 9) is derived and has a surface area between 30 and 50 square meters per gram as established by Brunauer-Emmett-Teller (BET) methods.

The present invention further includes item 11) the carbon allotrope or the carbon material of items 1)-10) bearing a multilayered three-dimensional nanocarbon array, wherein the material displays a minor peak near 1350 $cm^{-1}$ using a Raman Renishaw Spectrometer employing a 514 nm laser at 10% power; item 12) the carbon allotrope or the carbon material of items 1)-10) bearing a multilayered three-dimensional nanocarbon array, wherein the material displays a minor peak near 1350 $cm^{-1}$ using a Raman Renishaw Spectrometer employing a 514 nm laser at 10% power, wherein major peaks appear in the range of 1575 to 1600 $cm^{-1}$ and of 2695 to 2700 $cm^{-1}$ using a Raman Renishaw Spectrometer employing a 514 nm laser at 10% power; and item 13) the carbon allotrope or the carbon material of items 1)-10) bearing a multilayered three-dimensional nanocarbon array, wherein the material displays a minor peak near 1350 $cm^{-1}$ using a Raman Renishaw Spectrometer employing a 514 nm laser at 10% power, wherein major peaks appear in the range of 1575 to 1600 cm−1 and of 2695 to 2700 $cm^{-1}$ using a Raman Renishaw Spectrometer employing a 514 nm laser at 10% power, wherein stabilizing electron delocalization crosses between layers in an advanced interlayer connectivity bonding system involving the nanocarbon array.

The present invention further includes item 14) the carbon allotrope or the carbon material of items 1)-10), wherein the carbon material has a degree of combustion or oxidation resistance to an oxygen-bearing carbon allotrope or the gas at temperatures from 600 to 800 degrees Celsius; and item 15) the carbon allotrope or the carbon material of item 14), wherein stabilizing electron delocalization crosses between layers in an advanced interlayer connectivity bonding system involving the nanocarbon array.

The present invention further includes item 16) the carbon allotrope or the carbon material of items 1)-10) having a combustion temperature in air greater than 600 degrees Celsius; and item 17) the carbon allotrope or the carbon material of item 16), wherein stabilizing electron delocalization crosses between layers in an advanced interlayer connectivity bonding system involving the nanocarbon array.

The present invention further includes item 18) the carbon allotrope or the carbon material of items 1)-17), wherein individual crossene units are produced in oligomerized or polymerized states with properties thereby enhanced as in applications in composites and electrical conductivity for example.

The present invention further includes item 19) the carbon allotrope or the carbon material of items 1)-18), wherein heteroatoms or ensembles of heteroatoms like nitrogen, silicon, boron, phosphorous, sulfur and oxygen may be incorporated into the framework with minimal disruption of the electron delocalization but with the opportunity of inculcating the nanocarbon material with additional properties related to the nature of the heteroatom(s) incorporated; item 20) the carbon allotrope or the carbon material of items 1)-18), wherein nitrogen may be incorporated into the framework with minimal disruption of the electron delocalization but with the inculcation of additional properties specific to the nature of the incorporated nitrogen atom or ensembles of heteroatoms thereof; item 21) the carbon allotrope or the carbon material of items 1)-18), wherein silicon may be incorporated into the framework with minimal disruption of the electron delocalization but with the inculcation of additional properties specific to the nature of the incorporated silicon atom or ensembles of heteroatoms thereof; item 22) the carbon allotrope or the carbon material of items 1)-18), wherein boron may be incorporated into the framework with minimal disruption of the electron delocalization but with the inculcation of additional properties specific to the nature of the incorporated boron atom or ensembles of heteroatoms thereof; item 23) the carbon allotrope or the carbon material of items 1)-18), wherein phosphorous may be incorporated into the framework with minimal disruption of the electron delocalization but with the inculcation of additional properties specific to the nature of the incorporated phosphorous atom or ensembles of heteroatoms thereof; item 24) the carbon allotrope or the carbon material of items 1)-18), wherein sulfur may be incorporated into the framework with minimal disruption of the electron delocalization but with the inculcation of additional properties specific to the nature of the incorporated sulfur atom or ensembles of heteroatoms thereof; and item 25) the carbon allotrope or the carbon material of items 1)-18), wherein oxygen may be incorporated into the framework with minimal disruption of the electron delocalization but with the inculcation of additional properties specific to the nature of the incorporated oxygen atom or ensembles of heteroatoms thereof.

The present invention further includes item 26) the carbon allotrope or the carbon material of items 1)-18) and the modified material of items 19)-25), wherein functionalization is applied in a wide variety of known techniques including, but not limited to, 1,3 dipolar additions and other cycloadditions including carbene reactions, radical additions, fluorinations, alkylations, and redox procedures; item 27) the carbon allotrope or the carbon material of items 1)-18) and the modified material of items 19)-25), wherein chemical modification is applied to the outer surface to create a variety of different organic chemical functional groups to modify properties for rendering said carbon nanostructures amenable to various applications benefitting from the incorporation of organic functional groups for objectives in, but not limited to, adjusting solubilities in a variety of different solvents and compatibilities in polymerizations and solubilizations thereof in different media or in attachments of specialized agents useful, but not limited, to biological and medical applications, and also in enhancing prominent properties as in composite strengthening, electrical conductivity/storage, emf attenuation/reception, thermal insulation, radiation curing enhancement, biotechnology, biomedicine, preventive medicine, tribology, hydrophobicity, magnetism applications among others in regard to particular properties required for varied and diverse applications; item 28) the carbon allotrope or the carbon material of items 1)-18) and the modified material of items 19)-25), wherein functionalization through oxidation treatments of the outer surface as in treatment involving nitric acid for example prepares the nanoparticles for further functionalization particularly for the adjusting of properties of the nano particle(s) as in improving solubility capabilities in different solvents or in polymerization capabilities and otherwise for enhancing prominent properties as in composite strengthening, electrical conductivity/storage, emf attenuation/reception, thermal insulation, radiation curing enhancement, biotechnology, biomedicine, preventive medicine, tribology, hydrophobicity, magnetism applications among others in regard to particular property needs required for varied and diverse applications; item 29) the carbon allotrope or the carbon material of items 1)-18) and the modified material of items 19)-25), wherein functionalization through addition or cycloaddition reactions of the outer surface for example prepares the nanoparticles for further functionalization particularly for the adjusting of properties of the nanoparticle(s) as in improving solubility capabilities in different solvents or in polymerization capabilities and otherwise for enhancing prominent properties as in composite strengthening, electrical conductivity/storage, emf attenuation/reception, radiation curing enhancement, thermal insulation, biotechnology, biomedicine, preventive medicine, tribology, hydrophobicity, magnetism applications among others in regard to particular property needs required for varied and diverse applications; item 30) the carbon allotrope or the carbon material of items 1)-18) and the modified material of items 19)-25), wherein functionalization through simple halogen addition reactions of the outer surface for preparing the nanoparticles for further functionalization particularly for the adjusting of properties of the nano particle(s) as in improving solubility capabilities in different solvents or in polymerization capabilities and otherwise for enhancing prominent properties as in composite strengthening, electrical conductivity/storage, emf attenuation/reception, radiation curing enhancement, thermal insulation, biotechnology, biomedicine, preventive medicine, tribology, hydrophobicity, magnetism applications among others in regard to particular property needs required for varied and diverse applications; and item 31) the carbon allotrope or the carbon material of items 1)-18) and the modified material of items 19)-25), wherein functionalization through free radical addition reactions of the outer surface for preparing the nanoparticles for further functionalization as in sulfonation particularly for the adjusting of properties of the nano particle(s) as in improving solubility capabilities in different solvents or in polymerization capabilities and otherwise for enhancing properties as in composite strengthening, electrical conductivity/storage, emf attenuation/reception, radiation curing enhancement, thermal insulation, biotechnology, biomedicine, preventive medicine, tribology, hydrophobicity, magnetism applications among others in regard to particular property needs required for varied and diverse applications.

The present invention further provides item 32) applications of the carbon allotropes or the carbon materials of items 1)-18) and the modified material of items 19)-31) regarding, but not limited to material science, aerospace, 3D printing, polymers and plastics, emf thermoset plastic curing, thermal insulation, electronics, electrical transmission, emf attenuation/reception, catalysis, tribology, optical limiting, water resistance, cancer, preventive medicine, biological ablation therapy, emf-therapy, magnetic imagery, and other biotechnology innovations; item 33) applications of the carbon allotropes or the carbon materials of items 1)-18) and the modified material of items 19)-31) regarding material science applied, but not limited, to engagement with polymer, plastic and/or inorganic composites or matrices and also thermoset formulations thereof as applied to, but not limited to the aerospace, 3D printing, electronics, construction/rehabilitation industries; item 34) applications of the carbon allotropes or the carbon materials of items 1)-18) and the modified material of items 19)-31) regarding thermal insulation properties applied, but not limited, to refrigeration, clothing, housing, vehicles, shipping, aerospace, transportation, communication, industrial processes, electronics, paints and coatings, glass treatments, beverage and food service through the appropriate blending of the nanoparticles into the materials of interest directly or into the associated materials that render the thermal insulation properties; item 35) applications of the carbon allotropes or the carbon materials of items 1)-18) and the modified material of items 19)-31) regarding electrical conductivity/storage properties applied, but not limited, to electrical transmission, wiring, electronics, electrically motorized or hybrid vehicles, electrical motors, aerospace, mass transport, batteries and capacitors through incorporation of the nanoparticles into the appropriate carrier materials; item 36) applications of the carbon allotropes or the carbon materials of items 1)-18) and the modified material of items 19)-31) regarding emf attenuation/reception applied, but not limited, to Faraday cage protection of people as with plastics, coating, paints, clothing, electronic device sheaths, Wi-Fi and smart meter protective devices in homes and vehicles and electronics from electromagnetic pulses in regards to cell phones, computers, automobile computers wherein the nanoparticles are blended into the materials of interest directly or into the associated materials that render the electromagnetic attenuation protection; item 37) applications of the carbon allotropes or the carbon materials of items 1)-18) and the modified material of items 19)-31) regarding, but not limited to electromagnetic radiation attenuation properties applied, but not limited, to avoidance of electromagnetic radiation echo detection technology as with radar; item 38) applications of the carbon allotropes or the carbon materials of items 1)-18) and the modified material of items 19)-31) regarding emf attenuation/reception applied, but not limited, to microwave oven use as in susceptor pads as in replacement of metal foil alternatives and to radiation-induced warming capability in clothing and/or equipment where especially high solar radiation is available in the midst of frigid temperatures; item 39) applications of the carbon allotropes or the carbon materials of items 1)-18) and the modified material of items 19)-31) regarding emf attenuation/reception applied, but not limited, to enhancement of electromagnetic transmission reception equipment or techniques; item 40) applications of the carbon allotropes or the carbon materials of items 1)-18) and the modified material of items 19)-31) regarding, but not limited, to electromagnetic radiation attenuation/reception properties applied, but not limited, to thermal stimulation in a multitude of ways particularly for use in polymers, plastics, paints, coatings and adhesives or solders for curing purposes by blending the nanoparticles into the materials of interest directly or into the associated materials that render the thermal stimulation properties; item 41) applications of the carbon allotropes or the carbon materials of items 1)-18) and the modified material of items 19)-31) regarding tribology and/or thermal insulation properties applied, but not limited, to motor oils, lubes, cookware, associated coatings by blending the nanoparticles into the materials of interest directly or into the associated materials that render the tribology properties; item 42) applications of the carbon allotropes or the carbon materials of items 1)-18) and the modified material of items 19)-31) regarding hydrophobicity properties applied, but not limited, to water resistance applications as in window and windshield fog elimination, weather-resistant material and clothing, biotechnological and biomedical pursuits, biomaterial encapsulation by blending the nanoparticles into the materials of interest directly or into the associated materials that render water resistant properties; item 43) applications of the carbon allotropes or the carbon materials of items 1)-18) and the modified material of items 19)-31) regarding biotechnological and/or biomedical and/or preventive medicine utilization applied, but not limited, to selective tumor ablation due to radiation attenuation/thermal stimulation properties upon local administration of the nanoparticles followed by the application of highly directed microwave probes, antioxidant or photonic modulation effects for maintenance of living organism damage control effects by oral or injection nanoparticle procedures including use in acupuncture and related therapeutic regimens and also application topically especially on skin disorders including, but not limited to, moles and wounds; item 44) applications of the carbon allotropes or the carbon materials of items 1)-18) and the modified material of items 19)-31) regarding biotechnological and/or biomedical utilization applied, but not limited, to bone scaffolding especially regarding, but not limited, to 3D printing technology, x-ray or MRI contrasting agents, drug or gene delivery, and heavy metal removal; item 45) applications of the carbon allotropes or the carbon materials of items 1)-18) and the modified material of items 19)-31) regarding covetic alloy products produced in numerous manners including during the production of nanocarbon materials; item 46) applications of the carbon allotropes or the carbon materials of items 1)-18) and the modified material of items 19)-31) regarding thermal stability properties for allowing these materials' utilization under high temperature conditions; item 47) applications of the carbon allotropes or the carbon materials of items 1)-18) and the modified material of items 19)-31) regarding thermal stability properties in biological studies where unconverted nanomaterial would survive combustion removal of biological matter for the purposes of tracking delivery of nanocarbon materials in biological systems; item 48) applications of the carbon allotropes or the carbon materials of items 1)-18) and the modified material of items 19)-31) regarding magnetic properties in biological systems as in specifically targeted therapy and bioimagery and other magnetism important applications; and item 49) applications of the carbon allotropes or the carbon materials of items 1)-18) and the modified material of items 19)-31) regarding electromagnetic attenuation properties in regards to energy production especially in regards to solar energy issues.

While the foregoing is directed to embodiments of the present disclosure, other and further embodiments may be devised without departing from the basic scope thereof.

IV. Crossene Concept

A. Allotrope Confusion

Before the Rice University September 1985 discovery of the previously unimaginable new fullerene allotrope of carbon by Smalley, Curl and Kroto with Heath, O'Brien and Liu, only two pure natural allotropes were familiar: diamond and graphite. They were clearly known as distinct allotropes because of their reasonable abundance and their distinctively different natures in appearance and properties observable to the naked eye, requiring no sophisticated instrumentation. So what was the basis of difference between those first two millennially known allotropes of dramatically different natures and properties? The developing field of chemistry provided answers in establishing reliably predictive and useful bonding concepts with respect to a manageable list of atoms in a vast multitude of various molecules and materials.

The development of the Periodic Table by Mendeleev revealed the carbon element to occupy the fourth group of the second period, a unique position whereby it bore four valence electrons thus having four options for bonding between the carbon atoms of the respective allotropes. So, what is the difference in bonding between the individual carbon atoms in the two different allotropes?

As theory developed, the nature of the atom was determined to bear a very small tight positively charged nucleus surrounded by very distant orbitals of negatively charged electrons thereby achieving a charge balance either as a pure or complex element or a charged component in a salt. Based upon self-consistent reasoned logic, an understanding developed for explaining the natures and properties of different organic molecules as in alkanes, alkenes and alkynes. It became clear that bond angles for alkanes having four substituents and thus saturated in its bonding were generally equivalent as in methane (CH4) structured in a tetrahedron fashion with a 109.47 degree angle between each of the substituents where no inequivalent steric hindrance or substituent electronegativity effects are encountered.

The basic theory that was developing for atoms particularly in the second period is that there were four atomic electron orbitals consisting of one spherical s-orbital and three dumbbell-shaped p-orbitals perfectly angled from one another at 90 degrees and thus bearing the designations of the px, py and pz orbitals. To explain the tetrahedron orientation of alkane carbons, a hybridization scheme was devised for the one s-orbital and three p-orbitals of the second period elements wherein one portion of an s-orbital was blended with the three portions of the p-orbitals (px, py and pz). This type of hybridization was given the label $sp^3$ wherein a carbon is fully saturated bearing four substituents with a tetrahedron geometry about each carbon atom through bonding involving head-on sigma bonding.

Opposed to saturated alkanes, alkenes are unsaturated and planar in nature with each carbon being $sp^2$ hybridized with one order of unsaturation. The planarity of $sp^2$ hybridization derives from its three substituents lying in a plane with a leftover p-orbital standing perpendicular or orthogonal to that plane. For saturated alkanes, each of the four valence electrons of the carbons involved is occupied completely in head-on sigma bonds involving four different substituents (CH4). Unsaturated alkenes, on the other hand, bear what is called a double bond and two exclusively head-on single bonds as in ethylene (H2C═CH2). Thus, ethylene possesses two strictly head-on single bonds with the hydrogen atom substituents and additionally a double bond connecting the two carbon atoms.

The single bonds are viewed as involving head-on sigma bonding between the carbon and hydrogen atoms as is also the case with carbon atoms as in ethane (H3C—CH3). With single bonded alkanes, there is free rotation about the sigma bond apart from any steric hindrance due to bulky substituents replacing the hydrogen atom substituents of ethane. Double bonds are generally viewed as possessing both one head-on sigma bond between the two carbon atoms of ethylene and one pi bond arising from tangential overlap of the dumbbell lobes of the leftover p-orbitals. Thus, alkenes are planar with the uniting of the two leftover electrons from the two adjacent leftover p-orbitals combining to form a pi bond bearing the two loose electrons with the upper half of the pi bond involving the tangential overlap of one portion of the dumbbell lobes on the upper side of the planar molecule coalescing together like those on the underside. This tangential coalescence of the separate lobes of the loose dumbbell-shaped p-orbital on the upper and lower side of the plane provides a significant barrier to rotation of the respective substituents at each end of the double bond.

So, ethylene (H2C═CH2) with $sp^2$ hybridization bearing a double bond between individual carbon atoms involves only three substituents per each carbon atom, two singly bonded hydrogen atoms and one doubly bonded carbon within a plane bearing equivalent angles of separation of roughly 120 degrees, depending on the bulkiness to the potentially sterically hindering substituents. The leftover p-orbitals remain as unhybridized dumbbell orbitals perpendicular to the plane of the alkene. The two p-orbitals on each carbon smear together tangentially to form a pi bond bearing the two loose electrons coming from each p-orbital of the two carbon atoms involved with head-on sigma bonds connecting the carbons to their substituents in the plane.

Alkynes exhibit yet another geometry proclivity of linearity bearing a triple bond between each of the two carbon atoms involved possessing $sp^1$ hybridization linearity with substituents 180 degrees apart from one another through a sigma bond arrangement as in acetylene (C2H2). The two p-orbitals leftover in sp1 hybridization form a pi electron cloud from the respective carbon atoms involving two loose p-orbitals perpendicular or 90 degrees apart from one another with a total of four electrons smeared together into a kind of a pi bond cloud cylinder of four loose electrons.

With this instruction on fundamental bonding options, the bonding nature in the diamond allotrope is seen involving carbon atoms of purely saturated $sp^3$ hybridization bonded together with a tetrahedron geometry with four other carbons through four separate tethers. A rigid lattice structure then accrues all of sigma bonded carbons that is inflexible in nature with a manifestation of the observed extreme hardness noted of diamonds.

The bonding nature in graphite is seen as purely unsaturated hybridized sheets of $sp^2$ carbons like greased flexible chicken wire that easily slide across one another thereby explaining the allotropes softness and lubricative nature. Additionally with graphite, the leftover dumbbell-shaped p-orbitals with one lobe above the plane and one lobe below allows for a free flowing passageway or circuitry for the loose electrons provided, one from each dumbbell-shaped p-orbital with each p-orbital bearing a lobe above and a lobe below each sheet in a collection of sheets of loose electrons above and below the sheets.

This gains additional significance in understanding of the nature of the sheets of graphite particularly when the sheets of graphite are considered not merely composed of simple $sp^2$ double bonds but rather $sp^2$ aromatic bonding. Aromaticity represents a separate bonding concept having an enhanced thermodynamic stability due to resonance stabilization energy discussed earlier in the instant disclosure wherein bond lengths are identical for all carbon-to-carbon bonds as opposed to alternating single and double bonds of simple conjugated multi-unsaturated alkenes. The resulting free circulation of electrons in aromatic systems like graphite explains the observed electrical conductivity of graphite. The diamond allotrope being completely saturated without any freely circulating electrons exhibits electrical insulation properties.

The point of this rehash of the fundamentals of bonding is to point out that different carbon allotropes necessarily require different molecular bonding systems as now pointed out for distinguishing diamonds from graphite. Such is necessary as diamond is a monotropic allotrope with a thermodynamic stability inferior to graphite. It is their difference in bonding nature that differentiates them regarding thermodynamic stability.

With the present view of fullerenes bearing all sp2 carbon atoms, the geodesic dome bonding model proposed in the first ten days of its discovery has persisted for 35 years. The geodesic dome model is presented as involving aromatic bonding of planar benzene six-membered rings pasted upon the surface of a sphere. Thus, the newly discovered fullerene allotrope was being represented with the same aromatic bonding nature as that which defines the graphite allotrope. Such would violate the concept of allotropes having different levels of thermodynamic stability requiring different modes of bonding. For 35 years, chemists have misunderstood this concept and thus have been stuck with a false and relatively useless aromatic graphite bonding concept for the new fullerene allotrope.

As that characterization of fullerenes does not venture beyond the separate graphite allotrope bonding model, there cannot be a separate level of thermodynamic stability between the two since they both are viewed as having the same bonding model. The flaw in this ten-day formulation of the geodesic dome bonding model is clearly seen in regards to the thermodynamically untenable extreme strain existing in the $sp^2$-based planar benzene rings forced into highly strained curvature depicted in a geodesic dome model. The extraordinary thermodynamic stability of the discovered C60 fullerene or buckyball, particularly with it bearing the tightest of curvature of fullerenes, accordingly stands in sharp contrast to the geodesic dome-proposed bonding model. Only through an alternative bonding model to the first proposed geodesic dome model can this allotropic bonding definition logic challenge be resolved.

1. Fullerene Bonding

From the above discussion, it is clear that the concept of an allotrope being differentiated from another allotrope was overlooked in that different allotropes require different bonding models. Saturated bonding is the basis of the definition of diamonds and unsaturated aromatic bonding defines graphite. Their respective properties then are clearly reasoned to coincide with their respectively dramatically different bonding systems. Missed in those first ten days of the surprise discovery of the new allotrope of fullerenes was the incongruency of planarity-defined aromatic rings being pasted upon a sphere thereby inducing untenable bond and ring strain out of the required planarity of aromatic rings. Missed also in those first ten days was an understanding of the concept of allotropes requiring unique bonding and structure models for alternative allotropes. The fact that each allotrope exhibits its own distinctive level of thermodynamic stability proves that different bonding natures exist between the respective allotropes.

So, a new allotrope requiring a new concept in bonding was completely overlooked in that first ten days of the surprise discovery of the new fullerene allotrope. For the last three and a half decades, the bonding model of fullerenes has stood misconstrued of a geodesic dome geometry and accordingly has significantly stalled the development of the technology. Instead of a rugged spheroidal surface of the proposed truncated icosahedron of the buckyball, a perfectly smooth rounded surface of carbons with all equivalent angles and bond angles, as with the benzene rings of graphite, is a far better model of bonding for explaining the nature and properties of the new allotrope. Distinction between the two, geodesic dome versus perfect sphere, however, presents a challenge even today that hitherto has not definitively been resolved with sophisticated instrumentation and quantum mechanical calculations.

It was already known that graphite is more thermodynamically stable than diamond. Why? Diamond has no loose electrons like graphite. Chemists determined that graphite possessed free-roaming migratory loose electrons associated with their planar $sp^2$ hybridized carbon constituents bearing each a loose p-orbital, such electrons labeled customarily as "delocalized electrons." These free-to-roam delocalized electrons are capable of circulating or migrating as part of a circuitry within a cluster of pi-like cloud of electrons above and below a planar hexagonal ring system. The graphite sheets of free-roaming delocalized electrons arise from a series of double bonds in a completely unsaturated system linked together through a conjugated bond system that shifts into a highly thermodynamically stable aromatic species bearing identical carbon-carbon bond angles and bond lengths. Incidentally, similar identical bond angles and bond lengths are now seen as essential as opposed to a geodesic dome model in defining fullerenes as part of a highly preferred geometry required of a perfectly rounded and smooth sphere essential for defining a unique bonding system for fullerenes as differentiated from the alternative allotrope unique bonding systems of diamond and graphite.

Evidence of superior thermodynamic stability for the equivalent carbon atoms of aromatics (and now also the equivalent carbon atoms of fullerenes) has appropriately already been established as detailed earlier in the instant disclosure due to delocalization of electrons freely able to migrate and circulate within the confines of the pi-like cloud smear of overlapping lobes of the p-orbitals on each side of the plane of a molecule of benzene. The increase in thermodynamic energy is labeled resonance stabilization energy. Similarly, a kind of resonance stabilization energy would be expected for fullerenes bearing equivalent carbon atoms.

The puzzle in understanding the difference between two of carbon's allotropes of diamond and graphite is clear. Accordingly, one might have expected that diamonds with enough energy provided in an inert environment of an annealing oven would overcome the energy of activation to convert to the more thermodynamically stable graphite allotrope. But, no, the graphite allotrope is bypassed altogether in the annealing of nanodiamonds that instead proceed past the graphite allotrope directly to the more thermodynamically stable fullerene allotrope and even to the ultimate in thermodynamic stability of the carbon allotrope introduced in this instant disclosure of crossenes as noted below regarding the Palkar article.

All three allotropes of graphite, fullerenes and crossenes possess carbon atoms possessing one order of unsaturation with thus only three bonding connections per carbon atom in each allotrope. The key to understanding the two newly identified carbon allotropes of a nanocarbon nature, fullerenes (1985) and crossenes (2019), is their respectively different natures of curvature and thus bonding systems.

As opposed to the aromatic portrayal of fullerenes where "graphitic bonding" is routinely invoked in describing bonding optimization for CNOs as characterized according to Raman spectroscopy, "graphitic bonding" is actually impossible for curved systems as with fullerenes and crossenes, where p-orbitals align with either the nucleus of a sphere or the axis of a cylinder. "Graphitic bonding" obviously defines graphite where the leftover p-orbitals of the sp2 carbons all align with one another orthogonal to the plane of the graphite or graphene layers. Such alignment is impossible in curved systems like fullerenes and crossenes. Indeed, for fullerenes, the leftover p-orbitals are aligned with the nuclear core of spherical systems like CNOs and with the axis of cylindrical or tubular systems like CNTs of SWNTs or MWNTs.

Such a difference in p-orbital alignment is the defining difference between graphite or graphene and fullerenes of single or multilayered concentric shells. The electronic bonding model for fullerenes induces the observed curvature and correspondingly an altogether different electronic character for the respective sides of a particular layer of fullerenes versus the uniform electronic character regardless of side of the plane for the graphite allotrope. For the fullerene allotrope, the underside concentrates electron density into an electron rich interior surface and the outer side thereby experiences a paucity of electron density into an electron deficient exterior surface. Nevertheless a pi-like cloud of electrons is expected due to the network of carbons each bearing a lone p-orbital providing exactly only one electron for electron delocalization per carbon atom.

So where electron delocalization for graphite proceeds along a planar surface with the limitation of edges, electron delocalization for fullerenes proceeds endlessly in a closed shell system. Cylindrical fullerene members exhibit inferior electron delocalization to that of spherical members due to the existence of edges at the ends of the cylinders or tubes. It is the degree of electron delocalization that distinguishes allotropes according to different degrees of thermodynamic stability.

Existing art, on the contrary, argues that it is the reduction of dangling bonds (highly unstable unpaired electrons as of free radicals) as of the edges of graphite or ends of CNTs that that accounts for the formation of fullerenes with a marked improvement in thermodynamic stability accordingly through the curved continuous shells or layers in fullerenes. Existing art also invokes a geometrical consideration for fullerenes requiring the involvement of five-membered (pentagon) rings (twelve for all spherical systems regardless of size according to Euler's theorem). The chemical understanding of the prior art therefore consists of patchwork remedies for explaining the nature of the new fullerene allotrope as opposed to a general bonding concept requiring a perfectly rounded sphere of equivalent carbon-carbon bond angles and bond lengths. The confusion in the understanding of the nature of allotropes requiring completely different bonding models then is quite pronounced before this instant disclosure.

With the understanding of the difference in p-orbital orientation in generating opposing electronic character of the respective surfaces of fullerenes, a clear distinction in bonding between graphite and fullerenes is established. This difference in viewing graphite versus fullerenes then reveals the difference in bonding systems between the two.

Graphite has an aromatic bonding system well-established in the organic chemistry world through August Kekule 150 years ago when the aromatic concept of benzene was first realized in that respective 1,3,5-cyclohexatriene and 2,4,6-cyclohexatriene isomer proposals could not be differentiated in the laboratory. Thus two proposed separate isomers arising from disubstitution in the 1,2 or ortho positions could not be isolated separately. Accordingly, it was established that benzene is not composed of alternating single and double bonds but of bonds of equivalent lengths and angles with equivalent pi-like clouds above the planar system and below it. In the case of benzene by itself, it is generally represented with a donut-shaped pi-like cloud of three electrons hovering over the upper side of the six-membered unsaturated sp2-carbon-bearing ring with an equivalent donut-shaped cloud hovering over the underside.

Fullerene, on the other hand being three-dimensional in nature, has its own fullerenic bonding system of pi-like clouds of delocalized electrons. So with C60 fullerene bearing a total of 60 carbons in the system with correspondingly 60 electrons from each leftover p-orbital of its trigonally substituted carbons, 30 electrons occupy the exterior pi-like orbital with the remaining 30 electrons occupying the interior pi-like orbital. That is a distinct difference in the respective graphite and fullerene bonding systems in that the respective pi-like clouds of delocalized electrons for the two are odd in number for aromatic bonding systems but even for fullerenic bonding systems. Also different between the two allotropes is that the respective pi-like clouds of delocalized electrons on the different sides of the layers of the respective allotropic systems are identical for aromatic allotropic systems but very significantly different for curved fullerenic allotropic systems. So, there is a differentiation of electron density on the two sides of the fullerene system due to the p-orbital alignment with the nucleus for CNOs and with the axis for CNTs with ellipsoids aligning with both an axis and a nuclear core on the ends.

So, fullerenes differentiated according to interior versus exterior surfaces of the curved allotrope. Instead of the planar electron delocalization thermodynamic stabilization of graphite or graphene equivalent on both sides of the plane, fullerenes possess a volumetric pi-like cloud of delocalized electrons of nonequivalence for the two sides of each layer of the curved network shells of the allotrope, the interior surface being electron rich and the exterior surface being electron sparse. Accordingly, an attractive force exists between layers of a kind of electrostatic nature as the underside electron rich surface of one layer is attracted to the exterior electron-deficient surface of the underlying layer. Such explains the formation of onions during production as carbon fragments are laid down on top of an electron deficient reactive fullerenic surface that then transform to a fullerenic structure concentrically in establishing the most thermodynamically stable form possible dependent upon the availability of carbon fragments.

Again, aromatics as with benzene and higher ones like naphthalene and phenanthrene bear an odd number of electrons on each side including graphite and graphene systems. On the contrary, spherical fullerene systems of a single layer or multilayers bear an even number of electrons on each side for any and all layers of the CNOs. Such provides an additional distinction between the allotropes of graphite or graphene and fullerenes. Another difference in aromatic bonding systems of simple aromatic molecules like benzene is that fullerenic systems have a continuity of closed shells available for continuous or infinite electron delocalization whereas aromatics are limited to two dimensions only and that with edges for the graphite allotrope and thus far less thermodynamically stable than fullerenes. Additionally, with simple benzene systems with substituents retain their aromatic bonding system through their characteristic electrophilic substitution capability. For fullerenes, however, substituted molecules as with benzene cannot exist without total destruction of the fullerenic bonding system and thus an equivalent to electrophilic substitution is impossible as they have no potential leaving group as is the case for benzene molecules.

2. Crossene Bonding

So, clearly graphite or graphene and fullerenes bear dramatically different bonding systems that relate to dramatically different structures and properties and represent clearly different carbon allotropes with dramatically different degrees of thermodynamic stability. Just as a significant energy of activation barrier exists separating nanodiamonds and fullerenes, a high energy of activation barrier exists in separating fullerenes from crossenes. Just as the diamond lattice saturated bonding structure must be broken in the transformation of nanodiamonds to fullerene CNOs, the C60 fullerene core of concentric shelled fullerene CNOs must be broken in the transformation of fullerene CNOs to crossene CNOs. Such transformations require a significant amount of energy of activation to move from one allotrope one level of thermodynamic stability to another of superior thermodynamic stability. The fullerene to crossene transformation not only requires sufficient energy of activation for breaking the C60 fullerene core of the concentric shell system but also for breaking apart the multi-shelled system of electrostatically engaged layers associated with attraction between the layers due to the differential in electron density between an electron rich interior surface of one layer engaging an underlying layer of an electron deficient exterior surface. The resulting crossene structure has no C60 core but rather a hole or void of roughly 3-7 nm of a unique ragged diameter.

So in moving through the monotropic carbon allotropes of increasing thermodynamic stability, one proceeds from a saturated diamond sp3 tetragonal carbon lattice structure to a trigonal carbon concentric spherical shelled fullerene structure with a C60 fullerene core to a trigonal carbon irregular spheroidal structure bearing a unique irregular hole or void. What is the reason for the differences in thermodynamic stability for the three different allotropes, diamond to fullerene to crossene? What do their varying structures signify in reference to their respective thermodynamic stabilities? As was determined with benzene exhibiting a unique thermodynamic stability characterized as resonance stabilization energy associated with the free migration availability of electrons between Kekule's two proposed resonance hybrid structures, we see that the same electron delocalization phenomenon observed with benzene exhibiting exceptional thermodynamic stability applies to the different allotropes of carbon.

There is no possibility of electron delocalization for the fully saturated diamond in its rigid lattice structure and therefore it is the least thermodynamically stable of the carbon allotropes. Graphite is unsaturated and of an aromatic bonding nature and structure and thus is more thermodynamically stable than diamond due to its having a strong 2D planar electron delocalization capability. Fullerenes are also unsaturated having a strong 3D spherical electron delocalization capability accentuated further by the interplay of fullerene shells of electron rich interior surfaces with electron deficient exterior surfaces; thus, as the electron delocalization in fullerenes are endlessly unlimited as in infinite for each fullerene shell, 3D fullerenes are more thermodynamically stable than 2D graphite.

Crossenes are the most thermodynamically stable allotrope in that when the C60 fullerene core of its precursor 3D concentric shelled fullerene was broken, the ensemble of carbon atoms took on a new morphology of unique irregular multilayered and multilayered ribbon-like structures where a crossover of electron delocalization between layers is optimized to the point that the electrons of the whole crossene molecule are fully delocalized. The resulting crossene spheroidal system accordingly exists in long multilayered plateaus and multilayered ribbon-like structures whereby electron delocalization is achievable through a hypothesized alignment of graphitic like structures in those plateaus and ribbons in AA, AAA, AAAA stackings for establishing a kind of charge-transfer complex kind of connection for allowing the passage of electrons between layers. The unique irregularity of each spheroidal and void structure accrues on a kinetic basis during the transformation from one particular fullerene CNO to one particular crossene CNO for maximizing electron delocalization and thus thermodynamic stability in a concerted fashion similar to the laying down of millions of dominoes for achieving a specific objective. The name crossene was correspondingly applied to the new allotrope to highlight this crossover phenomenon that marks a distinct difference in bonding nature between crossenes and fullerenes that corresponding ties to an exceptionally enhanced electron delocalization capacity for crossenes versus fullerenes and thus its superior thermodynamic stability.

Just as there are defining studies regarding the difference in thermodynamic stability for the conversion of nanodiamonds to fullerene CNOs in multiple publications outlined in the Bartelmess and Giordani 2014 review as in the Tomita publication (S. Tomita, A. Burian, J. C. Dore, D. LeBolloch, M. Fujii, S. Hayashi, *Carbon* 2002, 40, 1469-1474), a most illuminating defining study is presented in the following publication (*Reactivity Differences between Carbon Nano Onions* (*CNOs*) *Prepared by Different Methods* Amit Palkar, [a] Frederic Melin, [a] Claudia M. Cardona, [a] Bevan Elliott, [a] Amit K. Naskar, [b] Danny D. Edie, [b] Amar Kumbhar, [c] and Luis Echegoyen*[a] *Chem. Asian J.* 2007, 2, 625-633 DOI: 10.1002/asia.200600426) comparing CNOs of a small number of layers (6-8 layers) produced from nanodiamonds to those of 20-30 layers generated through a underwater discharge action between two graphite electrodes.

The Palkar article reveals a thermodynamic stability factor tied to the Palkar article-unrecognized electron delocalization and thermodynamic stability related to the layer count for fullerene CNOs. A second thermodynamic stability factor becomes clear in the article using the new fullerenic electron delocalization and structure elucidation of the instant disclosure that was likewise unrecognized in the Palkar article. The second thermodynamic stability factor is associated with the interplay of layers in the fullerene multilayered CNO systems related to the layer attractions of electron-sparse exterior surfaces with electron-rich interior surfaces.

In the Palkar article brought to the attention of the inventors of the instant disclosure by the assigned Examiner, two differently produced CNOs were studied where their respective thermodynamic stabilities were evaluated according to a thermogravimetric analysis (TGA) with corroborating TEM, XRD, NMR, Raman, and EPR data. TGA measures the stability of a material in its resistance to combustion. One of the two CNOs of the Palkar study bore 6 to 8 layers prepared from an annealing process of nanodiamonds (nd) with the other CNO bearing 20-30 layers (15-25 nm in diameter with an average of 20 nm or roughly 25 layers) prepared according to an underwater arc discharge process (uwad). The nd-based process employed annealing temperatures of 1650° C. to generate from a nanodiamond precursor a CNO bearing TGA measurement stability of 700° C. For the uwad-produced CNO, the same 1650° C. annealing treatment led to a TGA stability of only 500° C. Upon increasing the annealing temperature to 2300° C., the uwad CNO's TGA also matched the 700° C. stability of the nd CNO annealed only at 1650° C. The TGA of the instant disclosure involving catenated chains of fullerene NCOs in a kind of envelope or cocoon of fused onions afforded similar exceptional thermodynamic stabilities and above following annealing of temperatures between 2200° C. and 2800° C.

The authors of the Palkar study could not interpret the results because they were restricted to the prevailing aromatic geodesic dome bonding model that had no firm understanding of carbon allotropes in general as discussed above. They missed seeing the possibility of the existence of a carbon allotrope beyond fullerene, that which we name crossene in the instant disclosure. Until this instant disclosure, there have been no reports found invoking a whole new carbon allotrope and accordingly no recognition of an electron delocalization bonding theory that correlates to the defining nature of carbon monotropic allotropes of their relative thermodynamic stability.

The additional annealing temperature required for the ad-produced CNO over the nd-produced CNO reflects the second factor in thermodynamic stability consideration for CNOs of the interplay of layers in the CNO with the alternating attractive forces between the electron rich interior surface of a particular layer with the electron deficient exterior surface of the underlying adjacent layer with an attractive field thereby set up over the whole set of nested concentric shells for the fullerene CNOs. A cascading interaction of a series of electrostatic attraction forces creates exceptionally strong binding of the layers together. The greater the number of layers involved, the stronger is the field or forces that are generated in proportion to the energy of activation barrier for conversion to the next carbon allotrope of a higher thermodynamic stability that is called the crossene allotrope in the instant disclosure.

The crossene allotrope has a superior thermodynamic stability to the other carbon allotropes because it has the greatest degree of electron delocalization capacity due to not just the individual layers of the CNO being involved but the whole molecule or system including the individual layers due to crossover electron delocalization between layers thus explaining the naming of crossene. So, thermodynamic stability is thus established for the respective carbon allotropes in the following sequence: diamond<graphite<fullerene<crossene. See FIG. 7 for a table comparing the different allotropes as discussed above regarding primarily to CNOs of the nanodiamond basis versus the catenated structures of the instant disclosure.

B. Carbon Nano-Onion Confusion

1. Review Articles

Until the instant disclosure, well-established authorities led primarily by Luis Echegoyen have grappled with the understanding and definition of carbon nano-onions (CNOs) of a characteristic curved morphology. Their numerous reports cast all CNOs into the presently recognized broad family of fullerene carbon allotropes as noted in the 2014 review article title by Bartelmess and Giordani: "*Carbon nano-onions* (*multi-layer fullerenes*): chemistry and applications:" Beilstein J. Nanotechnol. 2014, 5, 1980-1998. doi: 10.3762/bjnano.5.207 Received 13 May 2014, Accepted 10 Oct. 2014, Published 4 Nov. 2014, https://V-I\Nw.beilstein-journals.org/binano/articles/5/207. Such a general categorization of CNOs fell into place naturally with the evolving family of carbon allotropes of curved morphology and varying dimensions regarding overall radius for sphere, ellipsoid and cylinder alike: simple single-walled spheres or ellipsoids like C60 and C70 fullerenes and open-ended cylinders like carbon nanotubes (CNTs) including also their respective multi-walled, multilayered or multi-shelled versions that likewise applies similarly to complex carbon nanohorns (CNHs).

In the 2014 review, the following is stated: "Multi-shell fullerenes, known as carbon nano-onions (CNOs) and discovered by Ugarte in 1992 [8], are structured by concentric shells of carbon atoms." Also stated concerning the 1992 CNO discovery is the following: "In a report from 1995, Daniel Ugarte refers to CNOs as onion-like graphitic particles, which display a wide range of structures, explicitly including polyhedral to nearly spherical morphologies in his definition of CNOs [19]." An additional quote from the 2014 review runs as follows: "The diameter of the CNO nanomaterial depends on the synthetic protocol, but nevertheless, CNOs exhibit in general a high surface area to volume ratio."

Likewise, in an allotrope-focused 2015 review by Georgakilas, Perman, Tucek and Zboril, CNOs are restricted as well to the fullerene allotrope category: "Broad Family of Carbon Nanoallotropes: Classification, Chemistry, and Applications of Fullerenes, Carbon Dots, Nanotubes, Graphene, Nanodiamonds, and Combined Superstructures." [Chem. Rev. 2015, 115, 11, 4744-4822, Publication Date: May 27, 2015, https://doi.mg/10.102'1/cr500304f.htt2s://12ubs.acs.or9./doi/10.102i/cr500304f] Therein one finds the following quote: "Several research papers have discussed a fullerene-type graphitic nanoallotrope—a multishell spherical carbon nanostructure that is often called onion-like carbon. OLC structures consist of concentric graphenic shells such as giant fullerenes that enclose a series of progressively smaller fullerenes (see Figure). (14-18) They were first identified by Ugarte (19) in a mixture of carbon nanotubes after strong electron beam irradiation."

These two reviews illustrate the general state of confusion regarding CNOs (also OLCs or NCOs). Just as it is particularly nowadays regarding politically charged issues, the Scientific Method requires that the science is never fully settled and so it is also true regarding CNOs and the science behind fullerenes and crossenes in general. Indeed, no one can conclude the hypothesis is settled science regarding the hurriedly formulated geodesic dome model following the accidental discovery of fullerenes by three very surprised and unprepared spectroscopists and their hands-on student assistants Heath, O'Brien and Liu during the first ten days of September 1985, thirty-five years ago. In like manner, the science for multilayered systems of CNOs discovered twenty-eight years ago is unsettled. The foundations of both fullerene and CNO technologies have correspondingly languished unchanged until the instant disclosure.

The CNO technology has been calcified for decades in its formative stages of development. Attempts forward have been stifled without the rudder of sound theoretical understanding of fullerenes and also firm definitions of respective monotropic allotropes. The curved morphology of the highly stable fullerene allotrope requires a type of bonding undefined until the instant disclosure, one that accommodates its three-dimensional nature unconfused with graphitic bonding of the two-dimensional graphite allotrope. As for firm allotrope definitions as noted in the introduction of the instant disclosure, pure carbon compositions present themselves in different monotropic allotrope forms defined by "arrangement of atoms or molecular forms that are differentiated on the basis of bearing different numbers and/or alignment and bonding of atoms that are generally manifested by different shapes and/or different physical and chemical properties." For monotropic allotropes, transition temperatures from the lower allotrope to the next relate to the respective thermodynamic stabilities of the two allotropes with transitions, conversions or transformations proceeding between them in only one direction irreversibly.

With the two review articles in mind, terms of "graphitic particles," "graphitic nanoallotrope" and "graphenic shells" are incompatible with "multi-shelled fullerenes" and "giant fullerenes that enclose a series of progressively smaller fullerenes." Such mixing of allotrope terms for a specific material applies only to mixtures of the separate allotropes that don't represent then a pure allotrope. Such mixing of terms would register for the mechanical mixing of graphite and fullerenes for example. For systems of readily convertible materials like nanodiamonds to fullerenes NCOs and to crossene NCOs, mixtures exist only by mixing different monotropic allotrope materials at preconversion temperatures or when a material is cooled before complete conversion.

"Polyhedral" is a term selected in the literature in an effort to describe a curiosity discovered by accident for CNOs observed following annealing procedures that fits an alternative 3D geometry from that of regular concentric shells to that of irregular layers incorporating per onion system a void or hole with a mixture of curved and planar stretches. At the time of CNO discovery and up to the instant disclosure, both regular and irregular morphologies were viewed simply as CNOs without any explanation provided for their difference. The irregular geometry remains still very much in the curiosity stage of consideration with only a rudimentary understanding of carbon allotropes with respect to their respective degrees of thermodynamic stability clarified now by the instant disclosure.

Without even the buckyball rigorously and appropriately defined (mistakenly described with geodesic dome terminology) as well as confusion and imprecision regarding the concepts and natures of different allotropes of carbon, CNO technology and that of nanocarbons in general have been left in limbo with confusing and imprecise descriptions, definitions and correlations without which achievement of understanding necessary for advancement has been rendered most challenging. To further confuse the development, CNOs exhibit widely different properties with respect to CNO diameter or number of onion layers dependent upon synthetic protocol where CNOs can exist as a stand-alone structure or as a string of fused CNO structures encapsulated in chains or bunches in a cocoon or envelop as a result of catenation generated during certain synthetic protocols. Accordingly, Raman and TGA evaluations vary largely based on the involvement of different allotropes.

High surface area determinations were considered in the 2015 review to reflect CNO properties in general; on the contrary they reflect differences in properties associated with different synthetic protocols, especially regarding most stand-alone versus catenated CNO systems. From FIG. 6 in the instant updated disclosure, surface area measurements for the catenated CNO structures are dramatically lower along the lines of the naphthalene combustion-produced CNOs. The gram-scale synthesis of carbon onions; Mohammad Choucair a,*, John Arron Stride a, b a School of Chemistry, University of New South Wales, Sydney, N S W 2052, Australia b Bragg Institute, Australian Nuclear Science and Technology Organisation, PMB 1, Menai, NSW 2234, Australia CAR8ON 50 (2012) 1109-1115.

From the above considerations, the confusion in the world of curved carbon nanocarbons is abundantly clear in mixing allotrope concepts and in lacking a recognition of the key pivotal role of electron delocalization in sorting out the respective thermodynamic stabilities of the various carbon allotropes now specifically defined in the instant disclosure regarding fullerenes versus crossenes. The challenge all ties back to a misstep in the first ten days of the new fullerene allotrope discovery regarding the bonding and structure characterization of the so-called buckyball or C60 fullerene where a geodesic dome model was proposed for characterizing a sixty carbon glob.

With the state of the art in carbon bonding understanding at the time of the discovery of the new fullerene allotrope of carbon, each triply substituted carbon atom of the allotrope had to be inescapably singly unsaturated with the only option available for characterization of the respective carbon atoms being a planar sp2 hybrid status for explaining the connected nature of the sixty carbons. To account for the inescapable singly unsaturated carbons in the glob, each carbon had to fit all other singly unsaturated carbon atoms regarding the hybridization being planar sp2 carbon atoms in the structure and bonding nature with a lone p-orbital leftover orthogonal to the plane of the sp2 structure though such a planar structure would have to be highly strained out of planarity as in an inverted umbrella of fullerene structures.

2. Ugarte and Kroto 1992 CNO Introduction Publications

Besides the obvious confusion in the 2014 and 2015 review articles regarding a fundamental understanding of carbon allotropes and also of carbon nano-onions in general and especially regarding the now clearly obvious two distinct allotropic options of fullerene versus crossene CNOs, a 1992 publication was set forth in tandem with the original publication by Ugarte introducing CNOs for the first time. That tandem publication presented an exceptional perspective of Ugarte's publication from one of the original discoverers of the buckyball, Harry Kroto of Suffix University, before his winning the Nobel Prize in Chemistry in 1996 for said discovery along with his colleagues Richard Smalley and Robert Curl of Rice University. Carbon onions introduce new flavour to fullerene studies; H. W. Kroto NATURE VOL 359·22 Oct. 1992 pp 671-672.

Much understanding is now found with the instant disclosure for the questions posed by Kroto:

"The notion that graphite, composed of flat sheets of carbon hexagons, is the most stable form of carbon is called into question on page 707 of this issue1. D. Ugarte has found that soot, when annealed by intense electron irradiation, naturally transforms itself into giant nested shells of carbon, possibly the onion-like relatives of fullerene."

Such remarks reveal the efforts of one of the discoverers of the new fullerene allotrope of carbon to sort out the relationship between it and the graphite allotrope of carbon where he knows that in both cases trigonally bonded carbon atoms are involved. He does recognize that thermal treatment does provide a pathway between allotropes. His remarks touch upon the concept of the two different allotropes exhibiting two different levels of thermodynamic stability though not expressly written as such. It also emphasizes the flat nature of graphite that he knows is in sharp contrast to the fullerene allotrope of particularly high curvature of his discovered C60 fullerene also known as the buckyball.

"Our proposal, in 1985, that the stable C60 cluster detected during laser ablation of graphite has this form was initially greeted, by some, with natural skepticism."

As with the instant disclosure, new ideas bump into long held paradigms with sometimes exasperating resistance.

"After all, carbon, it was generally held, invariably forms flat sheets of atoms in hexagonal arrays, stacked as graphite-deemed the most stable form of the element."

This is still a generally accepted perspective that continues to stand even today 35 years later in a world not yet familiar or even aware of the advances in nanocarbon chemistry that Kroto and colleagues initiated in 1985.

"If, however, the C60 species, which had been created spontaneously in the chaos of a hot carbon plasma, was in fact a closed spheroidal cage, then the whole concept of the intrinsic flatness of graphite might need some reevaluation."

Here again, one of the top researchers in the field of the fullerene allotrope contemplates its relationship to graphite questioning even the flat nature of graphite. Although he is questioning the nature of allotropes without truly understanding an allotrope's relationship to thermodynamic stability and a unique bonding nature associated with a unique corresponding electron delocalization capacity.

He is on the right track, however, realizing that a significant thermal event as in a hot carbon plasma is necessary for generating sufficient atomic excitement as in utter chaos spontaneously created for converting one allotrope to another. This agrees with what the instant disclosure teaches regarding varying heights of energy of activation barriers for CNOs of different numbers of layers as in the Palkar article discussed above.

Kroto's thoughts correspond to the concepts discussed in the instant disclosure regarding the discovery of the new crossene allotrope of a substantially greater degree of thermodynamic stability than other unsaturated allotropes of carbon of graphite/graphene hexagon chicken wire and fullerenes that he had himself with his colleague Nobel Prize winners misconstrued as of a geodesic dome structure.

"It soon became apparent that on the scale of a few tens to a few hundreds of carbon atoms, graphite-like sheets of hexagonally arrayed carbon atoms would be unstable because of dangling bonds at the edges: this instability could be relieved by closure into a spheroidal network. Perhaps in bulk these edge instabilities would be insignificant, but on a small scale the need to satisfy the dangling bonds is probably decisive and leads to energy-driven closure."

The focus on allotrope stability is on minimization of unpaired electrons at the edges as of graphite or graphene sheets without consideration of diamonds that likewise has edges, though perhaps insignificant with respect to the bulk material as noted by Kroto, although any such free radical "dangling bond" in either graphite or graphene or also CNTs are most probably passivated by extraneous components in the environment as in moisture, oxygen or organic materials.

Unconsidered by Kroto is the concept of a new kind of 30 electron delocalization beyond the 20 understanding of benzene and aromatic ring systems so fundamental to the understanding of graphite and graphene. But if one of the fathers of the buckyball who undoubtedly in the intervening seven years since the buckyball discovery has directed his full attention on the subject and passed judgement on CNOs the day of their first publication, who would dare put himself at risk of ruthless peer pressure that might cost him grants by defying the established halls of science?

"Although it was originally thought possible to produce a set of perfectly closed onion-like shells, it also seemed likely that this would occur rather infrequently. The results of Smalley and colleagues8, however, indicate otherwise, and closure might be more the rule than the exception—at least during gas-phase nucleation."

Now starts the whole issue of onions being defective and characterized as OLC vs purely closed shells that then brings forth explanations of high surface areas considered until low surface area measurements were recorded for the catenated fused onion systems or molecules of the instant disclosure and recently the naphthalene combustion-based CNOs produced by Choucair.

"By high-temperature processing of small carbon particles, Ugarte has produced kernels which exhibit a remarkable degree of spheroidal structure."

Kernels correlate to the observed concentric shell structure of fullerene CNOs and would fit the model proposed in the instant disclosure with C60 fullerene or buckyball being the nuclear core for fullerene CNOs that leads to layout of subsequent layering with respect to interior vs exterior sides being of different electron density for the respective concentric spherical shells as they form thereby setting up a whole new thermodynamic stability issue that was clearly confirmed by the Palkar article without such recognition by the Palkar group.

"He finds that under the microscope's electron beam, small fragments of material produced in a fullerene generator can self-assemble or rearrange themselves into concentric spheroidal graphitic shells very similar to the structures observed by Iijima5. But Iijima believes his particles were produced in a different way, perhaps by nucleation in the gas phase (personal communication)."

This discoverer of the fullerene allotrope here demonstrates an awareness of the nature of the formation fullerenes including fullerene CNOs.

"The C60 buckminsterfullerene and other results indicate that 60-600-atom aggregates of carbon atoms must be more stable as a closed spheroidal cage than as a flat sheet. Now, Ugarte's results show that carbon atom aggregates of $10^6$-$10^7$ atoms appear to be more stable as onion-like structures than as flat sheets. (One can count the atoms because, assuming the object is perfect, the central shell has 60 atoms, the next 240, the next 540 and so on; FIG. 2 of Ugarte's article reveals 60 or more shells.)"

So, Kroto & Ugarte are proposing carbon counts into the millions per onion! That agrees with the numbers expected for the catenated CNOs structures of the instant disclosure.

"Ugarte's results are also interesting for the light they cast on the mechanism by which carbon atoms can rearrange themselves. More careful study is required to understand whether a nucleus is involved, but there is evidently an ordering process in which successive outer shells assemble around inner ones. Ugarte's very large structures are more spherical than Iijima's polyhedral particles, perhaps because they are not perfectly closed shells. The carbon nanotubes made last year by Iijima9 can be considered as elongated analogues of these spheroidal structures. But it is interesting that Ugarte's study indicates that elongated (amorphous?) structures appear to evolve or anneal into spheroidal ones."

Kroto realizes something interesting is lurking there with successive laydown of shells nucleated by the foregoing shell(s) that we now have explained via our electrostatic/electron delocalization model. Kroto was helplessly lost in his crippling work vaunting his geodesic dome model theory. The term polyhedral started here.]

"Ugarte's experiments may also take us back to the original motivation behind the carbon-cluster experiments that revealed fullerene—the question of what form carbon takes in interstellar space. The results add further evidence to conjectures, based on Iijima's original results, that some carbon particles in space might consist of concentric-shell graphite structures, perhaps surrounded by amorphous outside layers. Nevertheless, the most interesting question is whether, 500 years after Columbus reached the West Indies, flat carbon has gone the way of the flat Earth."

Kroto's publication was written in tandem with Ugarte's publication that introduces CNOs for the first time with many misconceptions now debunked in the instant disclosure: Ugarte, D. *Curling and closure of graphitic networks under electron-beam irradiation, Nature,* 359, 707-709 (1992), https://doi.org/10.1038/359707a0).

Abstract

The discovery[1] of buckminsterfullerene (C6o) and its production in macroscopic quantities[2] has stimulated a great deal of research. More recently, attention has turned towards other curved graphitic networks, such as the giant fullerenes (Cn, n>100)[3-4] and carbon nanotubes[5-8]. A general mechanism has been proposed[9] in which the graphitic sheets bend in an attempt to eliminate the highly energetic dangling bonds present at the edge of the growing structure. Here, I report the response of carbon soot particles and tubular graphitic structures to intense electron-beam irradiation in a high-resolution electron microscope; such conditions resemble a high-temperature regime, permitting a degree of structural fluidity. With increased irradiation, there is a gradual reorganization of the initial material into quasi-spherical particles composed of concentric graphitic shells. This lends weight to the nucleation scheme proposed[9] for fullerenes, and moreover, suggests that planar graphite may not be the most stable allotrope of carbon in systems of limited size.

A subsequent publication by Ugarte seeks to put the puzzle of fullerene CNOs together but with no chance of success utilizing the geodesic dome model versus the electron delocalization model introduced in the instant disclosure: D. Ugarte, Onion-like Graphitic Particles, Carbon, Volume 33, Issue 7, 1995, pages 989-99, https://doi.org/10.1016/0008-6223 (95) 00027—bget rights and content.

Abstract

"Nanometric graphitic structures (fullerenes, nanotubes, bucky-onions, etc.) form in different harsh environments (electric arc, electron irradiation, plasma torch). In particular, the onion-like graphitic particles may display a wide range of structures, going from polyhedral to nearly spherical. High-resolution electron microscopy is the primary tool for studying these systems. On the basis of HREM observations, we discuss the energetics and possible formation mechanism of these multi-shell fullerenes. The better understanding of the underlying processes would allow the development of an efficient production method."

3. Echegoyen 2001 Review

Luis Echegoyen is the premier researcher with several of his students following suit in a number of different research institutions. The paragraph below illustrates particulars of the instant disclosure including the requirement of a significant energy of activation between each carbon allotrope. Not considered in the review was recognition of the integral role electron delocalization plays and an appreciation of the foundational factors in establishing a new allotrope. See Chapter 19 Carbon Nano Onions; Luis Echegoyena, Angy Ortiza, Manuel N. Chaura and Amit J. Palkarb; aDepartment of Chemistry, Clemson University, Clemson, SC USA; bConocoPhillips Company, Ponca City, Oklahoma USA. Chemistry of Nanocarbons Edited by Takeshi Akasaka, Fred Wudl and Shigeru Nagase© 2010 John Wiley & Sons, Ltd. ISBN: 978-0-470-72195-7.

Upon heating to higher temperatures, a transformation of the diamond phase to a graphitic phase begins. See S. Tomita, T. Sakurai, H. Ohta, M. Fujii and S. Hayashi, *Structure and electronic properties of carbon onions. J. Chem. Phys.,* 114, 7477-7482 (2001).

Initially, above 900° C. the outer surface of the nanodiamond undergoes graphitization (FIG. 19.2b). However, a small amount of nanodiamond crystals remains at the core of the particle. Upon further annealing at 1100° C. the diamond cores from the smaller particles completely disappear to form graphitic shells while the larger particles still have some residual core (FIG. 19.2c). Further heating of nanodiamonds at 1500° C. transforms the nanodiamonds completely into graphitic structures (FIG. 19.2d). The major product is carbon nano onions having six to seven shells (FIG. 19.2e). At temperatures of 1500-1800° C. the existence of the separate onions becomes energetically less favorable than the formation of joint graphitic layers of neighboring onions. This results in the appearance of extended multi-shell graphitic cages with hollow centers as well as graphite-like ribbons with parallel graphitic planes (FIG. 19.2f). At the highest annealing temperatures (2100° C.) nanodiamonds transform into a faceted multi-shelled structure.

Accordingly, the new crossene carbon allotrope of the instant disclosure has slipped by unnoticed and unrecognized almost three decades even in the most discerning eyes of the vanguard practitioners of the art. So now, a revolutionary breakthrough is at hand in advancing the technology especially in differentiating one kind of CNO of regular spherical concentric shells of the fullerene allotrope from the alternative kind with layers or shells of irregular curvature and planarity only now recognized of the crossene allotrope.

C. Crossene Introduction

Introducing this new crossene allotrope of carbon is not for the faint of heart in the present age of media-induced doubt and indoctrination where thought, inquiry and speculation increasingly encounter a unified passionate inflexible wall of resistance. Who would dare to have the effrontery to question the enthroned establishment? Don't they know that "the science is settled?" Free thinking is a threat and deplored by those with special interests. Accordingly, the wheels of progress and ensuing benefits are stilled and even derailed.

Such was the challenge for Copernicus and Gallileo and also Tesla. Even the pre-1985 fullerene overtures suggesting a C60 molecule met resistance and skepticism: https://en.wikipedia.org/wiki/Fullerene [20200601] "Predictions and limited observations."

The icosahedral C6oH6o cage was mentioned in 1965 as a possible topological structure. Eiji Osawa currently of Tovohashi University of Technology predicted the existence of C60 in 1970. He noticed that the structure of a corannulene molecule was a subset of the shape of a soccer ball, and hypothesized that a full ball shape could also exist. Japanese scientific journals reported his idea, but neither it nor any translations of it reached Europe or the Americas.

Also in 1970, R. W. Henson (then of the UK Atomic Energy Research Establishment) proposed the C60 structure and made a model of it. Unfortunately, the evidence for that new form of carbon was very weak at the time, so the proposal was met with skepticism, and was never published. It was acknowledged only in 1999.

In 1973, independently from Henson, a group of scientists from the USSR made a quantum-chemical analysis of the stability of C60 and calculated its electronic structure. The paper was published in 1973, but the scientific community did not give much importance to this theoretical prediction.

Around 1980, Sumio Iijima identified the molecule of C60 from an electron microscope image of carbon black, where it formed the core of a particle with the structure of a "bucky onion". See https://en.wikipedia.org/wiki/Fullerene [20200601] "Predictions and limited observations.

Figure 8:
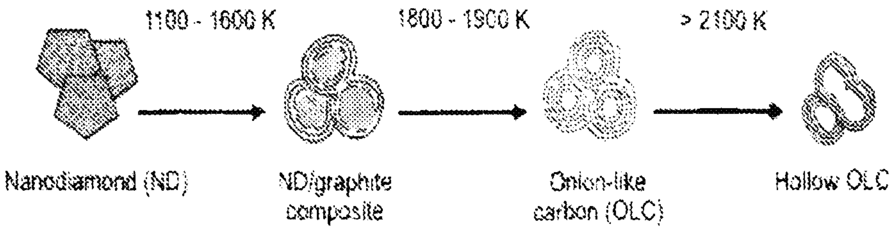
FIG. 8 illustrates the transformation steps of a nanodiamond to a hollow onion-like carbon.

Numerous reports particularly focused on nanodiamond-based systems likewise precede the instant disclosure, yet the invention of solving and explaining the puzzle of a two-allotrope CNO cascade was never understood nor delineated despite revealing diagrams like FIG. 8 from Newcastle University: https://research.ncl.ac.ukinanoscale/research/olc.html.

In this context, crossenes are introduced in the instant disclosure as a previously unexpected and unrecognized allotrope of carbon. Its introduction runs against the frenetic scientific pursuits of carbon nanotechnology that have yielded many valuable breakthroughs though encumbered with a highly flawed basis of discussion, the geodesic dome model of Buckminster Fuller.

Discovery of crossenes was unanticipated and long overlooked primarily due to the fundamental misunderstanding of the nature of allotropes and fullerenes. This misunderstanding has now persisted for over three and a half decades since it was first discovered! Without the new understandings delivered with the instant disclosure below, particularly with reference to the key property of electron delocalization capacity, any real progress into the world of nanocarbon technology would remain helplessly stymied.

The three-dimensional multilayered arrays of singly unsaturated interacting conjugated carbon atoms of an endless spheroidal continuity constitute crossenes as well as the recently discovered fullerenes with both being of the carbon nano-onion (CNO) category. Such arrays present a sharp contrast to the graphite allotrope of singly unsaturated interacting conjugated carbon atoms constituting a two-dimensional array without endless continuity of a spherical system due to the limitation of edges of the 2D sheet. Crossenes and fullerenes also stand in sharp contrast as they were unknown and unrecognized less than four decades ago whereas their much older sibling carbon allotropes of graphite and diamond have served society for millennia. Their discovery in sophistication is comparable in importance to society as in the development of cars following the discovery of the wheel and the development of computers following the discovery of the electron.

Unlike unsaturated arrays of unending continuity of crossenes and fullerenes, graphite comes clumped together in stacks of 20 sheets weakly interacting with one another through weak van der Waals forces of attraction thereby imparting exceptional lubricating or tribological properties. Fullerenes and crossenes, on the other hand, possess varying degrees of strengths and natures of van der Waals forces. They exhibit accordingly dramatically different effects and properties that result from their respective dramatically differently organized 30 arrays. The 30 arrays open up highly opportunistic powerful interactive forces in providing exceptional thermodynamic stability effects associated with hitherto unrecognized allotrope-specific properties that are all-defining, particularly in the recognition of crossenes as a new allotrope.

As with crossenes, fullerenes had also been overlooked as a new allotrope of carbon until three spectroscopy scientists with students got together at Rice University starting the first day of September 1985. After just ten days of intense experimental study involving a fledgling laser technology for defoliating a graphite target under vacuum, they unexpectedly stumbled upon a glob of sixty carbons using a mass spectrometer for detecting any graphite defoliants. It was an utter surprise met with great consternation as they were looking for proposed structures of linearity believed to exist in the cosmos. Encountering a volatile molecule bearing only carbon atoms, they wound up proposing a spherical shape to account for the necessary bonding of carbon with four valence electrons. All their efforts to describe this spherical shape finally settled upon their proposal of a truncated icosahedron with 20 hexagon and 12 pentagon ring structures pasted onto a sphere. After consulting with Rice's department of mathematics where they learned their description matched that of a soccer ball, their 60 carbon glob took on the name, buckyball.

Now, for 35 years, the world has been saddled with the unproductive confusion of that ten-day hurriedly and erroneously construed concept of fullerenes, particularly of the spherical category of geodesic dome proposed description primarily for the following three reasons:

1. Buckyball was an especially attractive name due to the correspondence to the soccer ball that symbolizes the most popular sport in the world, particularly useful for winning research grants.
2. Fullerenes were equally attractive being assigned its allotrope designation as a memorial to Sir Richard Buckminster Fuller who passed away two years earlier and who was the popular flamboyant architectural icon and MENSA president of the day famous for promoting geodesic domes as nature's most stable architectural structure.

3. The fullerene allotrope was discovered accidentally and unexpectedly and hastily announced to the world by spectroscopy-focused scientists rather than well-schooled active organic chemists with basic familiarity with aromatic molecules thereby allowing an infatuation for a highly enticing geometrical shape of a high degree of curvature to obscure reason: hexagon aromatic rings like benzene can exist with exceptional stability of resonance stabilization only with every carbon therein possessing $sp^2$ hybridization of rigorous planarity thereby disallowing conformity with a spherical surface of a truncated icosahedron with concomitant untenable loss of the thermodynamic stability, the very crowning property of the buckyball so vaulted at discovery.

Such considerations harken back the old issue of whether we live on a flat or spherical planet. Well understood already was the flat world of graphite and later graphene as a chicken-wire-appearing plane or sheet of fused benzene ring structures. The new allotropes of fullerene wound up couched in the well-studied flat world of benzene and graphite since there were no heroic Christopher Columbus molecular explorers to step forth bravely and chart a new course into the most intriguing true realities of a three-dimensional world. So, caught up in the fever, chemists of all stripes jumped helter-skelter on board the wrong ship. They convinced themselves that they saw untenably flat unsaturated aromatic molecular structures on the fullerene spherical surface to the point that they wound up invoking flat world chemistry in a 3D world. Thus, without wincing, they treated certain observed surface reactivity as cycloaddition reactions like that of Diels-Alder Reactions regarding the suggestion of cyclopentadiene entities interspersed with benzene rings on the surface. They did take into account some strain on a benzene ring on the surface for explaining certain addition reactions typical of olefins. There was no need to consider typical electrophilic substitution reactions regarding aromatic systems in that the benzene rings pasted on the surface bore no hydrogen atoms in pure carbon allotrope available for substitution.

All of these issues, however, pale in comparison to the overriding issue that the different carbon allotropes have dramatically different degrees of underlying thermodynamic stability: (1.) diamond, (2.) graphite (graphene), (3.) fullerene (single layer<multilayer; tubular<spherical), (4.) crossene. And, no, the extraordinary thermodynamic stability of fullerenes cannot be attributed to the macroscale architectural marvel of a proposed geodesic dome structure extrapolated down to the nanocarbon scale!

Since the discovery of fullerenes and now crossenes, it is becoming increasingly clear that a far more advanced concept is required over a mere architectural shape. After all, how does one account for real molecules with molecular properties like a definite vapor pressure and solubility as with C60 fullerene, the buckyball? Typical organic compounds with vapor pressures and solubility possess a high degree of thermodynamic stability or they would not exist. The mistakenly proposed geodesic dome model for fullerenes would make their existence untenable regarding thermodynamic stability considerations due to the impossibility of intolerably bent benzene rings on a spherical surface. The geodesic dome model is therefore pure fantasy when compared to typical run-of-the-mill chemical compounds in the field of organic chemistry.

Up to this point in time, every consideration regarding nanocarbon chemistry has been intensely fixated on this geodesic dome architectural model as there was such a rush to explore this new discovery of the fullerene allotrope after a long familiarity with the millennia-long known diamond and graphite allotropes of carbon. The bucky ball and the soccer ball geodesic dome proposed structures were simply too beguiling to consider any other structures and bonding models beyond those of flat world chemists.

D. Electron Delocalization

1. Aromaticity, Fullerenicity and Crossenicity

So confusion regarding the newly discovered allotrope of carbon called a fullerene has consequently plagued the development of the new technology and that of other nanocarbons. Accordingly, the confusion prevented the anticipation or recognition of the new crossene allotrope introduced through the instant disclosure. The confusion even penetrates the fullerene allotrope category itself where CNTs that come with discontinuous open edges at the ends of each cylinder are lumped together with spherical or ellipsoidal systems of continuous connectivity. The confusion relates primarily to the concept of electron delocalization. There is, however, another major interactive force also involving the network array of carbon atoms that bridges all curved allotrope systems involving multiple layers, whether cylinder or spherical; this most important van der Waal attraction consideration between multilayered systems is addressed in later sections.

A similar conundrum of misunderstanding was confronted a century and a half ago regarding the new molecular concept of aromaticity first proposed by August Kekule: On Kekule's insight-Archive ouverte HAL https://haLarchives-ouvertesJr/hal-01584824/document, and later refined by Linus Pauling. The Nature of the Chemical Bond. V. The Quantum-Mechanical Calculation of the Resonance Energy of Benzene and Naphthalene and the Hydrocarbon Free Radicals; J. Chem. Phys. 1, 362 (1933); https://doi.org/10.1063/1.1749304 Linus Pauling and G. W. Wheland.

The Nature of the Chemical Bond. Application of Results Obtained from the Quantum Mechanics and from a Theory of Paramagnetic Susceptibility to the Structure of Molecules, Linus Pauling, J. Am. Chem. Soc. 1931, 53, 4, 1367-1400 https://doi.org/10.1021/ja01355a027.

Before the days of instrumentation, the early German chemistry masters of refined laboratory skills as in crystallization and melting point and boiling point determinations discovered that there was only one isomer that could be isolated for a 1,2- or ortho-disubstituted benzene molecule. Up to that point, saturated and unsaturated organic molecules were known along with isolated and conjugated systems of alternating double and single bonds. The highly skilled German chemists deduced upon the wet-lab determinations of empirical formula for benzene of CH and the molecular formula of C6H6 that a ring structure with alternating double and single bonds or conjugated was required for describing benzene.

Limited to alternating single and double bonds in bonding concepts, there would be expected two different molecules or isomers for an ortho-disubstituted benzene, one with a double bond between the two benzene ring substituents and the other with a single bond between them. In the specific example of phthalic acid (ortho-dicarboxy benzene), the two isomers would be expected based upon existing bonding theory: 1,2-dicarboxy 1,3,5 cyclohexatriene with a carbon-carbon double bond between the two substituted carbons versus 1,2-dicarboxy 2,4,6 cyclohexatriene with a carbon-carbon single bond between the two carboxylate group-substituted carbon atoms. Back then carbon-carbon bonding and chemical structure interpretation was limited in conceptualization to only single, double or triple bonds as in alkanes, alkenes and alkynes.

The incongruency of bonding theory and chemical reality had reached an impasse! No one willing to bridge the gap and take a stand for a new bonding concept except for August Kekule who subsequently had to endure much criticism and resistance of the established chemical world as he had the audacity to buck the established theory of alternating single and double bonds. His new bonding model concept was a most disruptive to the chemical thinking of the day. He introduced and hung on tight to a new concept of bonding involving a mix or blend of partial single and partial double bonds between carbon atoms of exactly identical and equivalent natures for a fully unsaturated and also fully unsubstituted six-membered ring. Such became the basis of the concept of aromaticity and aromatic bonds and bonding concepts and a whole new category of organic molecules known as aromatic compounds. Such aromatic molecules allowed for the development of the concept of the free excursion capability of free-to-roam electrons over a network of multivalent atoms like carbon in benzene.

Such a new theoretical understanding opened up the concept of electron delocalization so vitally important in understanding the 3D world of fullerenes and crossenes of an altogether different 3D bonding nature in contrast to flat world 2D aromatic systems. Accordingly, the original bonding concept consisting of only single, double and triple bonds had to be adjusted to accommodate 2D planar equivalent aromatic bonds that subsequently had to be adjusted to accommodate 3D curved equivalent fullerenic bonds to be described below. Finally, now, crossenic bonding involving both curved and planar sections of the molecule intrudes upon the staid and generally inflexible chemical establishment over which much consternation and resistance is assured as with the introduction of aromaticity.

Such theoretical development details are necessarily presented here for the purpose of establishing the hard-won foundational nature of such discovery processes that is the basis of the instant disclosure. In subsequent sections of the instant disclosure, a similar new and disruptive theory is presented not only for the newly discovered crossene allotrope but also for the thirty-five year known fullerene allotrope based upon Kekule's first recognition of electron delocalization accruing from the concept of partial single and partial double bonds between carbon atoms in a flat or planar 2D world as with benzene. Such turmoil in theoretical development regarding aromaticity depicts well the new understanding of fullerenes and crossenes of the instant disclosure.

For many decades now, first year textbooks in organic chemistry have taught the Kekule fundamental concept that arose nearly a century and a half ago when Friedrich August Kekule explained why only one isotope of a 1,2-disubstituted benzene molecule could be isolated instead of the expected two if the benzene ring consisted only of alternating single and double bonds of a conjugated carbon-carbon double bond system. Now, textbooks and chemistry teachers will have to break away from their old notes and deeply entrenched understandings and embrace and teach new concepts as was the case with aromatic systems in order for organic chemistry to continue to advance according to the Scientific Method where science is rarely settled for those of inquiring minds.

The confusion regarding aromatic systems was finally resolved with the proposal by August Kekule of a new bonding and structural concept transcending the existing limited conceptualization of only single, double and triple bonds and structures thereof. The same confusion resolution accrues with the instant disclosure. The 30 world of the newly discovered crossene carbon allotrope of the instant disclosure bears correspondence in confusion to the flat world's conundrum regarding the bonding and structure of benzene.

With this disclosure, the critical importance of this electron migratory or circulatory phenomenon, also known as electron delocalization, is highlighted for explaining relative properties of each of the carbon allotropes bearing singly unsaturated carbon atoms: graphite/graphenes, fullerenes and crossenes. The greater the capacity is for electron migration or circuitry within the bonding structure of the respective allotropes, the greater is the respective thermodynamic stabilities along with their potential for electrical conductivity and also emf attenuation among a treasure chest of other properties presented herein.

2. Electron Delocalization Capacity and Thermodynamic Stability

All that was known a century and a half ago was just simple alternating saturated and unsaturated or conjugated carbon bonding systems. Then in a moment in time as if struck by a magic wand, the Kekule breakthrough changed the world of chemistry. New theories in bonding and structural understanding transformed the world of chemistry with the introduction of the concepts of aromaticity and aromatic molecules that continue today to require further development in existing understanding.

A comfort zone has long been established with that new understanding of benzene proposed by Kekule now looked upon as settled foundational science resistant towards being stretched or transformed. Accordingly, new nanocarbon allotropes have suffered in meaningful development as the flat 2D world of aromatics has infected the 3D world of fullerenes and crossenes through an insistence of a false geodesic dome model. Still there is a key feature of aromaticity that is foundational to understanding unsaturated carbon allotropes: graphite (graphenes), fullerenes and crossenes. It is the understanding that an array of unsaturated atoms of carbon atoms (occasionally also involving certain heteroatoms like nitrogen) provides a pathway for an electron migratory or circulatory phenomenon. The phenomenon is clearly observable for aromatic systems in chemical shift effects regarding nuclear magnetic resonance spectroscopy. Such electron migratory or circulatory capacity profoundly impacts the observed chemistries and thermodynamic stabilities of carbon allotropic systems or arrays. Circuitry of this nature compares to free-flowing electricity common to certain metals like copper, aluminum and silver but with the constraints of the physical limitations of carbon-based materials or molecules.

With this disclosure, the critical importance of this electron migratory or circulatory phenomenon, also known as electron delocalization, is highlighted for explaining relative properties of each of the unsaturated carbon allotropes. It turns out that the greater the capacity is for electron migration, circuitry or delocalization within the bonding structure of the respective allotropes, the greater is the respective thermodynamic stabilities along with their potential for electrical conductivity and also emf attenuation among a treasure chest of other properties.

Crossenes make up the ultimate allotrope of carbon in regards to thermodynamic stability that derives from its unprecedented capacity for electron delocalization. It is the final entry or caboose in a train of the most commonly known carbon allotropes in regards to relative thermodynamic stability: (1.) diamond, (2.) graphite (graphene), (3.) fullerene (single layer<multilayer; tubular<spherical), (4.) crossene. Recently, the possibility of crossene systems involving stacks of twisted graphene units may have surfaced that may predict the possibility of crossene systems for other multilayered systems as of carbon nanotubes (CNTs) regarding MWNTs vs SWNTs (multi-walled nanotubes vs single-walled nanotubes). Tunable correlated states and spin-polarized phases in twisted bilayer-bilayer graphene Nature May 6, 2020 Online https://doi.org/10.1038/s41586-020-2260-6 Nature|www.nature.com. Yuan Cao1, Daniel Rodan-Legrain1, Oriol Rubies-Bigorda1, Jeong Min Park1, Kenji Watanabe2, Takashi Taniguchi2 & Pablo Jarillo-Herrero2.

Due to their required multilayered nature, crossenes come in the form of a massive unsaturated molecule bearing potentially multiple millions of carbon atoms depending on whether catenation of the multilayered systems is involved. They are commonly characterized as carbon nano-onions (CNOs) due to their multilayered structure for the category of generally spherical or spheroidal structures. Through an annealing process discussed below in detail regarding carefully controlled temperatures, pressures and prevailing atmospheres, an initial fullerene-based CNO system serves as the CNO precursor for conversion to the far more electronically dynamic or electron-delocalized crossene-based CNO system.

The crossene and fullerene allotropes specific to this instant disclosure both come in the form of catenated chains and/or branched chains, as in a kind of cocoon or envelop, with the fullerene CNOs bearing fused concentric shelled onions and the non-concentric layered crossene CNOs bearing more diffuse often ribbon-like multilayered structures. Though potentially of lengths greater than 100 nm, diameters of such chains generally fall well under 100 nm and thus all catenated systems generally fall into the category of nanocarbons.

The consideration of the concept of electron delocalization in regards to thermodynamic stability was fundamental to the discovery of this new crossene allotrope. Most of those caught up in the frantically paced high-tech efforts in the technological development of the new Nanocarbon Age that began with the discovery of the geodesic dome-modeled buckyball in 1985 appear to have passed over lightly the great theoretical breakthrough works in organic chemistry provided by August Kekule 150 years ago.

General organic chemistry textbooks today tackle the long-held challenge of defining aromatic materials, systems involving most commonly six-membered 20 planar unsaturated carbon rings. The observation that the simplest example of aromatic compounds, the benzene molecule ($C_6H_6$), is flat with all bond lengths and bond angles identical was quite a curiosity and challenge for explanation that continues somewhat even to this day (see below regarding HMO theory). So has it been the case also today regarding three-dimensional fullerenes and now regarding the new allotrope crossene.

For many decades now, first-year textbooks in organic chemistry have taught the fundamental understanding of the relationship between thermodynamic stability and electron delocalization regarding benzene with closed loop avenues of electron delocalization or circuitry that define aromaticity. Unsaturated systems with road blocks associated with various levels of hydrogenation don't fill the bill. This subject was previously discussed in the originally submitted instant disclosure regarding the nature of aromaticity. Electron delocalization of a complete uninterrupted conductive unit was discovered to be related to thermodynamic stability. Confirmation was found via calorimetric hydrogenation reaction studies. An exactly measurable thermodynamic stabilization due to electron delocalization was consequently determined for benzene versus cyclohexene and called resonance stabilization energy.

The thermodynamic stability of the two-dimensional unsaturated planar systems as with the benzene molecule incorporating a closed electron circuitry was found to be roughly 35% superior to the broken circuitry of nonplanar cyclohexene or cyclohexadienes. The calorimetrically determined difference between 1,4-cyclohexadiene (unconjugated) and benzene provided another route for establishing the identical resonance stabilization energy of benzene as well. Conjugated 1,3-cyclohexadiene exhibited slightly better thermodynamic stability over cyclohexene or 1,4-cyclohexadiene as it possesses a certain degree of electron delocalization over four contiguous unsaturated conjugated carbon atoms. From these calorimetric evaluations of the hydrogenation process, it is clear that a full cyclic electron delocalization provides for exceptional thermodynamic stability in benzene measurable as resonance stabilization energy.

These observations are of fundamental importance for the discovery of the new three-dimensional allotrope of crossene in regards to its superior thermodynamic stability to three-dimensional allotropes of fullerene and for fullerene exhibiting superior thermodynamic stability over two-dimensional planar allotropes of graphite and graphene. Of course, electron delocalization or circulation exists for graphene systems similar to that of benzene but immensely more extensive due to the massive fused ring chicken-wire structure, thus explaining their superior thermodynamic stability to that of diamond.

3. Electron Delocalization Through Free-to-Roam Electrons in Orthogonal p-Orbitals Electron delocalization or circuitry in graphene systems is further clarified by considering in greater detail its individual unit of existence, the benzene molecule. Resonance stabilization energy is most satisfactorily viewed as an electronically symmetrical or balanced molecule. Textbooks routinely describe benzene with donut-shaped clouds of pi-electrons on the flip sides of the two-dimensional planar benzene molecule. With each of the six carbons of benzene bearing a planar sp2 hybridization (see the original disclosure and below), a sigma-bond-unaccounted-for free-to-roam fourth valence shell electron occupies both lobes of its respective orthogonal dumbbell-shaped p-orbital. To achieve electron circulation symmetry, the six upper and six underside dumbbell lobes of the orthogonal p-orbitals must bear three electrons each.

The fourth valence shell electrons associated with p-orbitals serve in their leftover capacity as potentially loose or free-to-roam electrons that are fundamental to the concept of electron delocalization and the associated concept of enhanced thermodynamic stability associated with resonance stabilization energy. For benzene, the upper and underside lobes of the six orthogonal p-orbitals associated with each of the six carbon atoms of the planar benzene ring provide the highly energetically favorable highway for electron circulation or circuitry that is the basis of electron delocalization and accordingly the root of enhanced thermodynamic stability for closed cyclic unsaturated conjugated systems.

Such thermodynamic stability is additionally shown with commiserate enhancement through hydrogenation calorimetry for naphthalene where electron circuitry or delocalization is extended to fused ring systems like naphthalene bearing ten carbons and thus ten loose fourth valence shell electrons in the fused ring system that is duly balanced and symmetrical with five loose free-to-roam electrons delocalized in a closed cyclic unsaturated conjugated carbon pi-cloud system above and below the two-dimensional planar unsaturated fused ring system. The same applies to anthracene and phenanthrene bearing fourteen loose valence shell electrons in the fused ring systems with even higher calorimetrically determined levels of resonance stabilization energy and thus thermodynamic stability. Accordingly, uninterrupted closed cyclic unsaturated conjugated carbon-based graphene chicken-wire system would be expected to have an odd number of delocalized electrons in the respective pi clouds above and below the graphene plane and to exhibit exceptional thermodynamic stability.

The substantial resonance stabilization energy of benzene marks it as a special molecule characterized as possessing aromaticity. Indeed, all planar delocalized systems of conjugated unsaturated molecules fit the same characterization as being aromatic or possessing aromaticity as well. It should be noted that it is commonly accepted that the high electron delocalization of aromaticity is defined by Huckel Molecular Orbital Theory (HMO) according to The 4n+2 Rule of numbers of electrons proposed to be required to exhibit aromaticity and the corresponding properties. The 4n+2 Rule works for benzene, naphthalene, anthracene, phenanthrene and also undoubtedly graphene systems as well.

The 4n+2 Rule, however, may simply reflect geometric barriers for systems containing only 4n electrons associated with what is labeled anti-aromaticity as with cyclobutadiene striving to achieve planarity as is much the same with cyclooctatetraene. An additional troubling issue with the HMO theory is the requirement that electrons must be paired in a system of bonding and antibonding orbitals the illustration of which is routinely provided in textbooks as a means of proving aromaticity. In reality, however, odd numbers of electron in the pi-clouds above and below aromatic ring systems for highly electron delocalized systems stands in sharp contrast to the paired electron orbitals depicted according to the HMO theory.

In both the case of benzene and graphene systems, electron circuitry or electron delocalization is confined to a planar habitat bearing non-traversable edges for graphene systems. The removal of this limitation or barrier is achieved with three-dimensional fullerenes and crossenes where curvature of surface allows for limitless connectivity and thus a whole new order of magnitude in electron delocalization or circuitry capability unavailable for planar aromatic systems like graphene. Accordingly, unsaturated three-dimensional systems exhibit superior thermodynamic stability to the planar systems of graphene thereby explaining the superior fullerene and crossene thermodynamic stabilities to that of the planar systems of graphene and graphite.

Graphene systems with equivalent pi clouds above and below the plane providing electron delocalization associated with a certain level of thermodynamic stability might be more precisely deemed to be composed of aromatic bonding while fullerene systems would then be composed of fullerenic bonding and crossenes composed of crossenic bonding available only for three-dimensional systems of curvature each. The curved 3D structures of fullerenes and crossenes bearing fullerenic and crossenic bonding respectively exhibit superior thermodynamic stability over graphene with its discontinuity of planar systems due to planar systems having the limitation of edges for full electron delocalization capacity.

Crossenes and crossene bonding, however, bear an additional imprecision in description of bonding in that they exist only in multilayered systems bearing long planar or plateau stretches of a graphene nature as well as sections of fullerenic tight curvature. The curved sections serve as kinds of doorframes or window frames for fixing graphenic sections in place in a most favorable arrangement for allowing crossover of electron delocalization between layers. Thus, unlike the purity of fullerenic bonding for fullerenes, there is a mix of graphenic and fullerenic bonding for crossenes relegating the term crossenic bonding imprecise. Accordingly, the name crossene fits in that crossenes are a cross between multilayered graphene units and multilayered fullerene units. Originally, the name crossene was given due to the realization of a crossover mechanism of electron delocalization between layers of a multilayered system. Such stands in sharp contrast and with an exceptional energy of activation barrier for conversion to crossenes from fullerenes that are limited in electron circuitry to individual layers.

A stacking order or pattern of exact overlap of graphene six-membered ring benzene units is required to allow crossover between layers through a conductive bridge in the form of a kind of charge transfer complex. Thus, coupling between layers through a conductive connection can proceed only through AA, AAA, AAAA, AAAAA, . . . stacking alignment. Such alignment is impossible for concentric shelled fullerene systems. Only where almost pure hexagonal unsaturated rings can align with one another between layers can crossover of electron delocalization proceed.

Such exact alignment and overlap is impossible for fullerenes for two reasons:

1. Equivalently spaced carbons per concentric shells for spherical fullerene NCOs especially by way of the updated model for fullerenes of the instant disclosure that displaces the original geodesic dome model thereby disallowing alignment of would-be benzene ring units.
2. Match-up impossibility of carbon unit structures if the geodesic dome model were to apply where, for example, the alignment of the 60 carbon atoms of the core C60 fullerene would be impossible with the 240 carbons of the next layer C240 fullerene separated by 0.34 nm from one another.

Accordingly, a major rearrangement and reorganization of constituent carbon atoms is required for the conversion of fullerenes to crossenes where alignment can be achieved through multilayer stretches of graphenic layers held in place by multilayered fullerene corners with unprecedented electron delocalization proceeding between individual layers through a crossover charge-transfer mechanism as well as along individual layers of layered graphene and fullerene components.

4. Electron Delocalization Pathway Differences in p-Orbitals for Planar Vs 3D Systems Whereas symmetry and balance in free-to-roam electronic components in aromatic graphenic systems is now understood to require an odd number of electrons on the respective outside and underside surfaces, fullerenes bear an even number of electrons on their respective exterior and underside surfaces. Thus, C60 fullerene bearing sixty trigonally substituted unsaturated carbon atoms bearing one loose free-to-roam fourth valence shell electron each possesses sixty loose free-to-roam electrons for electron delocalization. Accordingly, instead of an odd number of electrons on the respective surfaces, an even number is required as with C60 fullerene with thirty electrons on the exterior side and thirty on the underside. Likewise for the next shell of the multi-shelled fullerene system bearing 240 carbons, 120 electrons would be delocalized on the interior side with the remaining 120 electrons delocalized on the exterior side. The same applies for each layer or shell of the multilayered concentric shelled fullerene system according to the respective electron populations for each shell according to the number of carbons per shell as determined by the $60 \times n^2$ where "n" is the shell number: thus 30, 120, 270 and 480 for the respective "n" shells of 1, 2, 3, and 4 with corresponding total carbon and available free-to-roam electron counts of 60, 240, 540 and 960 respectively.

Electron circuitry or delocalization differs for aromatic systems and also cylindrical fullerene systems from that of spherical fullerenes. Both suffer from an interrupted, broken or incomplete delocalized system corresponding to a reduced degree of thermodynamic stability. Interruption occurs at the edges of two-dimensional graphene systems and uncapped carbon nanotubes (CNTs) bearing open ends to the cylinders. There are, nevertheless, closed end cylinders or tubes that fit the geometric shape of an ellipsoid that has uninterrupted electron delocalization as in C70 fullerene that exhibit superior thermodynamic stability but less than that of spherical fullerenes and concentric multilayered fullerene systems. In other words, cylindrical fullerene electron delocalization and thus thermodynamic stability are limited for CNTs (SWNTs and MWNTs) where electron circulation ends at the open ends of the tube or cylinders. Such limitations are removed for fullerene spheroidal systems like simple C60 or C70 fullerenes or CNOs where the electron circuitry or electron delocalization continues three dimensionally layer by layer without interruption though ellipsoids being less symmetrical involving two different alignments, one portion a spherical nuclear core and the other portion a cylindrical axis.

Crossenes go a major step further in allowing for even greater electron circuitry/delocalization. Accordingly, extraordinary thermodynamic stability is observed particularly by TGA through the opening of additional pathways for electron circulation/delocalization beyond the restraints of the respective single shells or layers of the ensemble of concentric fullerene shells to the whole unsaturated multilayered system. This is achieved through a kind of charge transfer conductive connection between layers where stacking arrangement along long "graphitic" planar stretches can orient with one another layer through AA, AAA, AAAA graphene-line stacking patterns. Thus, electron delocalization extends not just along individual concentric shells or layers of fullerene systems but between them or across them as well to allow delocalization not just along individual shells or layers but throughout the whole material or molecular system. Such opens up opportunities for crossenes unattainable by fullerenes as in electrical conductivity and high thermal stability and strength as in composites as well as exceptional emf attenuation effects in shielding or curing of thermoset plastics.

With the instant disclosure additionally, the discovery of crossenes for spheroidal systems may extend to multilayered graphene systems where AA, AAA, AAAA . . . alignment is opportune to enhancing thermodynamic stability for the ensemble of such a grouping of carbon atoms due to a similar concomitant increase in electron delocalization or electron circuitry; it would be expected, however, to be of a somewhat lesser degree for graphite and layered graphenes and also perhaps to MWNTs and thus of a somewhat lesser degree of increasing thermodynamic stability, especially due to the open circuitry at the edges.

5. Three Dimensional Electron Delocalization/Circuitry Bonding Considerations

The world of chemistry went through a major paradigm shift when the unusual chemistry of benzene and aromatics was explained in terms of intermediate stabilizations due to electron delocalization capacity associated with carbon-carbon double bounds in conjugation in a cyclic arrangement. As opposed to isolated double bonds as in olefins that commonly exhibit addition reaction behavior, aromatic systems commonly exhibit electrophilic substitution reaction behavior in order to preserve the highly thermodynamically stabilizing electron delocalization of such systems.

Graphene systems cannot undergo electrophilic substitutions in that there are no hydrogens (or rather protons) to exchange with the electrophile attacking agent. Nevertheless, graphene systems possess an exceptional degree of electron delocalization and thus thermodynamic stability in the same theoretical bonding consideration as proposed for benzene. Based upon the sp hybridization system models presented in the original disclosure, p-orbitals perpendicular or orthogonal to the $sp^2$ hybridized carbons of planar graphene systems are foundational. These p-orbitals are invoked as providing a circulation or delocalization pathway for the leftover fourth valence electron leftover from the trigonal sigma bond system around each carbon atom in the $sp^2$ carbon atom chicken-wire planar system.

For two-dimensional graphene systems, the leftover p-orbital of the $sp^2$ hybridized system possesses two lobes for accommodating its one leftover valence electron, one lobe of the underside of the plane and one lobe on the exterior side of the plane. Being in a plane, the p-orbitals, except for occasional slight aberration effects, bear identical lobes to the p-orbital on the underside as the exterior side. In other words, the p-orbitals align themselves not head-on with one another as in strong sigma bond formation but rather tangentially to one another perfectly to produce a weaker but fluid bonding system for allowing the leftover fourth valence electrons of each carbon to migrate or delocalize over the whole system of $sp^2$ carbons.

Just as it was such a paradigm shift for chemists regarding the new understanding for two-dimensional planar benzene or aromatic or graphene planar systems, such a paradigm shift is only now underway inescapably with the instant disclosure. For over three decades now, since the discovery of the bucky ball chemists have been severely limited to a two-dimensional aromatic system pattern pasted onto a sphere. What else would one suggest upon discovering a glob of sixty carbons only in an identifiable molecule by way of mass spectrometric identification? Additionally, the impromptu assignment received instant acclaim by the regular world of politics and sports that customarily is bored and challenged by the esoteric world of chemistry. What a draw for research grants and funding it thereby became. Now, that the excitement has long passed with little to show for it, might it be considered high time that a new bonding model be pressed into action like a new center forward?

Indeed, this instant disclosure is like a very bad tasting pill. The world has feasted on the geodesic dome concept of Sir Richard Buckminster Fuller until it runs dry. Most chemists are fully aware that benzene rings with sp2 carbons must be planar and invoking it as pasted upon a sphere is foundationally unconscionable, especially for such a small glob of 60 carbon atoms where the degree of curvature from planarity is at its maximum. This makes no sense as the C60 fullerene exhibits extraordinary thermodynamic stability nearly two orders of magnitude greater than C70 fullerene based on propensity for formation even though C70 has a slightly less tight degree of a curvature being an ellipsoid as opposed to being spherical. Additionally, what would explain the geodesic dome model regarding its proclivity to existing with exceptional thermodynamic stability in multi-layered or multi-shelled structures as generally accepted regarding CNOs? In other words, what would be the driving force for one layer or shell plating over or enveloping an underlying layer or shell?

6. Electron Delocalization Pathway Differences in p-Orbitals for Planar Vs 3D Systems So, long overdue is a new look at curved unsaturated systems of fullerenes and now the newly discovered crossene allotropes. As noted above with benzene and graphene systems, the leftover p-orbital of the $sp^2$ carbons of said systems are aligned perfectly with one another apart from occasional defects and aberrations. With fullerene and crossene systems, the carbons involved are likewise trigonally substituted but obviously not planar in curved structures.

If a graphene sheet is rolled up into a CNT, the previously perfectly aligned to one another p-orbitals are now no longer aligned to one another but rather to an axis with each p-orbital pointing perfectly at the axis. For a spherical system like the bucky ball C60 fullerene, the p-orbitals wind up identical and not of a geodesic dome nature at all. Each p-orbital is perfectly pointing at the exact center or nucleus of the bucky ball innermost fullerene unit alone or in a multi-shelled or layered system of concentric shells with the number of carbons in each shell matching the formula Carbon Count per Shell $n=60\times n^2$.

For the simplest and most thermodynamically stable of the simple (non-layered) fullerenes, the bucky ball C60 fullerene, the trigonally substituted carbons are not planar at all as would have to be for the geodesic dome model but rather deformed into a kind of umbrella appearance with the central rod or pole to the umbrella being perfectly central to the flaring out units. The same can be observed regarding each carbon in fullerenes.

The central rod is the axis of each trigonally substituted carbon pointed perfectly to the nuclear core of the fullerene system that now is better represented as orthogonally proportioned to the flared out sigma bonds of the fullerene. So, as opposed to the graphene systems that also have a central orthogonal rod, the dumbbell-shaped orbital lobes on the underside are not identical to those on the exterior side. Instead, with an orthogonal angle for the central rod different from the 90 degrees of the graphene systems, the two dumbbell-shaped orbitals lobes are no longer identical.

In sp hybridization descriptive language, the graphene system possesses carbons of all perfectly planar sp2 carbons with the central rod at a 90 degree angle to the plane of the graphene system. For fullerenes, on the other hand, there are various gradations of s versus p content to the sp hybridization model between sp2 and sp3. With C60 fullerene, the sp hybridization approaches a tetrahedral sp3 configuration while the sp hybridization on the $20^{th}$ layer and beyond approaches an almost planar configuration. It's like an asteroid vs the earth; one can readily see the curvature up close for the asteroid but the earth has confused man for some time as being flat—not unlike the present confusion regarding the geodesic dome model regarding fullerene systems.

Now, with this sp hybridization gradation concept in mind, one can address electron delocalization/circuitry and thermodynamic stability issues along with the unique reactivity of fullerenes versus other electron delocalized systems like benzene and graphene. Sticking with the simplest C60 fullerene system with all the p-orbitals equivalent and equally pointing to the center of the spherical glob of carbons, there is a strong degree of tangential overlap on the underside where the lobes are squeezed together but a much weaker degree of tangential overlap on the exterior side where the lobes diverge outward from one another.

Common between graphene systems and fullerene systems then are their both being comprised of trigonally substituted carbon atoms with a leftover p-orbital. The difference then is the angularity or the orientation of the central axis of each trigonally substituted carbon. Both afford an avenue for electron delocalization or electron migration or circuitry but with graphene only along a plane with confining edges while fullerene along a three-dimensional unending loop, more so for spherical or spheroidal systems than for cylindrical systems. It is the unending loop capacity of the fullerenes that allows for the greater degree of electron delocalization over graphene systems.

Now, with the two lobes of the p-orbital no longer being equivalent for fullerenes as opposed to graphene systems, the outer layer of lobes overlap significantly less with one another as is usually key to strong bonding here in a tangentially pi bonding sense and thus the exterior surface exhibits an inclination to react with components of its environment. The key evidence of this reactivity is extensive regarding the surface chemistry studies of C60 fullerene and also CNOs. That is easily discernable as C60 clearly exhibits properties of an organic chemistry molecule with a certain degree of solubility in certain solvents required for purification by crystallization and chromatography plus a vapor pressure valuable in purification via sublimation. Indeed, it is this exceptional surface reactivity of C60 fullerene with the ultimate of curvature that makes it an exceptional antioxidant that sucks up by reaction with the surface reactive oxygen species like nothing else before its discovery.

The height of evidence for the highly reactive surface of fullerenes due to the outer p-orbital lobes projecting outward from the nuclear core of the fullerene is the fact that multilayered systems form during the formative synthesis process as with underwater arc discharge procedures leading to 20 to 30 layers. Rare is the speculation for such an observation because it cannot be explained by the geodesic model for which fullerenes were named by the 1996 Nobel Prize winners in Chemistry of Smalley, Curl and Kroto. Such a limiting concept for fullerenes is undoubtedly a major reason for its most unsettlingly slow progress to commercialization. Below, further development of the layering phenomenon is discussed in the next section.

The next allotrope to consider is the one presented in the instant disclosure. Crossenes also are composed of trigonally substituted carbons but rearranged through an annealing process requiring varying degrees of temperature depending on the onion size and degree of layering. The arrangement requires the destruction of the carbon atom order and p-orbital orientation of the concentric layers or shells of carbons in the fullerene ensemble of carbon atoms with a high degree of thermodynamic stability over planar graphene systems. In the fullerene concentric shell systems, a C60 fullerene is almost always the core fullerene (perhaps an occasional C70 core) around which the other layers grow according to the formula above with a spacing between shells of 0.34 nm just like that of the layers in graphene or graphite systems.

The concentric shell system has a high degree of thermodynamic stability not just because of the high degree of electron delocalization regarding each individual layer or shell. No, an additional thermodynamic stability accrues from the interaction of the layers most strongly with neighboring layers with the underside electron-rich lobes of the p-orbital of the outer shell being strongly attracted to the electron-deprived exterior lobes of the p-orbital of the underlying shell. It would be anticipated that there would be an field of attraction that develops along the whole set of layer thereby explaining the insatiable growth of the outer layers of the layered system to the point, for example, of bearing 24,000 carbon atoms in the 20th shell.

So, annealing temperature for conversion of a layered fullerene system will need to be increased for highly layered systems versus much lower layered fullerene systems. The reason for the need for increased annealing temperatures corresponds to the degree of thermodynamic stability attained for respective layered systems targeted for conversion to a crossene system. The more highly layered concentric shelled fullerene system bear higher energy of activation barriers associated with not only overcoming the electron delocalization and thermodynamic stability of each shell but also the thermodynamic stability associated with the attractive field effects between each layer. Confirmatory data is provided In the next section with exacting measurable evidence of the bonding structure model proposed in this section.

7. Open Literature Support with Respect Thermodynamic Stabilities-Electron Delocalization Plus Multilayer Van Der Waal Attraction Particularly through sufficient thermal treatment, an ensemble of component carbon atoms in a material or molecule especially of a nanocarbon nature of nonoptimized thermodynamic stability may transform through favorable kinetic pathways to systems of more extensive electron delocalization and consequently higher levels of thermodynamic stability. Such a case is recalled by one of the inventors during his earlier works in the observance of the formation of a bridged paracyclophane (Grassman P. G., Bailey T. F., Hoye R. C., J. Org, Chem., 1980, 45, 2923-2924. doi: 10.102/Jo0130a039).

The work of Palkar et. al. is exceptionally revealing in its comparison of CNO systems of dramatically different size with a layer count of less than 10 for the nanodiamond-based (nd) system and between 20 and 30 for the synthesis route involving underwater arc discharge (uwad) between graphite electrodes. Unknown to the authors was their encounter of an unrecognized existence of a crossene allotrope, though of a far inferior form to that of the far more illuminating example of the disclosure. Accordingly, the authors were unable to explain unexpected TGA results in connection to differing annealing temperatures of nd vs uwad-based precursors.

Palkar et. al. annealed both the nd and the uwad samples first at 1650° C. under an inert gas atmosphere. The respective TGA combustion temperatures came in unexpectedly at dramatically different temperatures: 500° C. vs 700° C. for the uwad vs nd precursor systems respectively. Subsequently, both the nd and uwad precursor systems were annealed at 2250° C. and both then exhibiting TGA combustion temperatures of roughly 700° C.

The Palkar et. al. publication was most supportive of the instant disclosure and instructive in gleaning other thermodynamic stability relevant issues regarding the precursor to the crossene. Bogdanov et. al. lend added support. Both Palkar et. al. and Bogdanov et. al. stumbled across without recognition the crossene allotrope of the disclosure noting particularly through Bogdanov et. al. an unexplained curiosity of a multifaceted spheroidal structure labeled polyhedral in their descriptive characterization.

The Palkar et. al. publication revealed different thermodynamic stabilities of the respective precursors to the as-yet-unrecognized respective crossene allotropes. The 700° C. TGA was unachievable at an annealing temperature of 1650° C. for the uwad precursor due to its layer count being two to three times that of the nd system. To transform the uwad precursor to a crossene allotrope required annealing temperatures of roughly 2250° C.

The increase in annealing temperature needed from 1650° C. for the nd precursor to 2250° C. for the uwad precursor reflects the exceptional fullerenic thermodynamic stability of the uwad precursor of between 20-30 layers vs the nd precursor of less than 10 layers. A higher annealing temperature of molecular excitation for rearrangement of crossenes is seen in the TGA data after different annealing temperature exposures of nd-based vs the uwad-based fullerene precursors.

8. Details for the Process of Transforming Fullerene CNOs to Crossene CNOs

As noted in the previous two sections of this Section II CIP component to this instant disclosure and in further clarification of the general annealing instructions of the original disclosure, it is clear that the choice of annealing temperature and residence time is most dependent on the precursor ensemble of carbon atoms. For the purposes of disclosing the instant novel allotrope in general, the originally given disclosure could be considered sufficient. But, for those with different precursor systems, a further work of instruction may be helpful.

Some level of simple experimentation will be necessary as with the development of any new chemical process. A mere simple adjustment of the temperature setting of the annealing oven under an inert gas environment is all that Is needed. Actually, with sufficient temperature most any multilayered fullerene system will rearrange and convert to the crossene allotrope of the instant disclosure.

Once the threshold for overcoming the energy of activation for conversion of a particular fullerene system to a crossene system is achieved, there is some value depending on application intended for higher temperature application and perhaps longer residence times for optimizing electron delocalization and thermodynamic stability through developing a greater degree of order and electron delocalization and thermodynamic stability.

9. Crossene Application Opportunities

The specific composition studied and reported upon of the instant disclosure is uniquely useful for the recognition of the existence of the previously unknown crossene allotrope for the following reasons:

1. Potentially unlimited quantities of the new crossene allotrope material of the instant disclosure are produced for study and evaluation with consistent and reproducible purity and carbon nano-onion characteristics generally unknown in the field of nanocarbon technology with an exceptionally low degree of polydispersity in regards to onion size and number of layers.
2. The crossene allotrope material of the instant disclosure is derived from a unique fullerene carbon nano-onion feedstock available commercially of exceptional consistency and reproducibility from one production run to the next unknown for the roughly fifty different synthesis routes known in the field of nanocarbon technology where additionally an exceptionally low degree of polydispersity is achieved in regards to onion size and number of layers.

3. The crossene material of the instant disclosure bears an onion size and layer count customarily double to triple that of the most studied carbon nano-onion materials of undesignated allotrope characterization derived from a nano-diamond based feedstock.
4. The crossene material of the instant disclosure exists in a cocoon or envelope of multiple onion units fused together that accentuates the nanocarbon properties tied to the exceptional degree of electron delocalization that marks the unique nature of the crossene allotrope coupled to potential composite crosslinking properties deriving from catenated chains of onions involving the reactive exterior surfaces.

Because of the specific composition of the instant disclosure being available in copious supply, a multitude of evaluations have been possible to perform with exceptional reproducibility and revealing exceptional properties significantly different from carbon nano-onion produced from the roughly fifty alternative routes for producing carbon nano-onion materials.

1. The crossene material of the instant disclosure and its fullerene feedstock exhibit a BET surface area approximately a tenth of the roughly fifty alternatively synthesized carbon nano-onion materials.
2. The crossene material of the instant disclosure exhibits a significantly superior thermal stability determined by TGA (thermal gravimetric analysis) over the roughly fifty alternatively synthesized carbon nano-onion materials.
3. The crossene material of the instant disclosure exhibits generally sharper Raman peaks and greater D/G ratios.

In the roughly fifty alternative processes for producing carbon nano-onions (CNOs), none of the criteria noted above is observed: abundant quantities, exceptional reproducibility, extremely tight polydispersity, layer count greater than ten, catenated or fused onion systems within an integrating cage cocoon.

E. Crossene Summary

1. The Fullerene Discovery and Eventual Universal Recognition and Acceptance

For millennia, diamonds and graphite have been known to mankind. Does that mean that fullerenes and crossenes did not exist until discovered? No, it just means that we could not perceive their existence. They were not generally something found in bulk in pure form like diamonds and graphite. Yet, char and soot have been known as long as if not longer than diamond and graphite, but they have been found only as mixtures of a manner of carbon materials that are mostly the result of incomplete combustion. Nevertheless, lurking therein from common bonfires or effluent of combustion engines to lightening or meteor strikes of carbonaceous materials, a broad and rich dictionary or encyclopedia of mixtures of fullerene and crossene materials and amorphous carbon like activated charcoal lurk therein.

Spectroscopists at Rice University in the first ten days of September 1985 were pursuing a totally unrelated cosmic research project completely apart from any interest or consideration of carbon allotropes whatsoever, much less new ones when they experienced a Twilight Zone moment in history by encountering by accident and utter surprise a mere whiff of a 99% pure vapor form of a never before observed new allotrope of carbon proven by mass spectrometric evaluation. They stood in total awe and wonder. They found themselves sailing in uncharted waters and whether they wanted to our not, they had to deal with it as the first chosen to witness a whole new world of nanometer dimensions.

It was not unlike encountering a new dimension of existence or a whole new universe. They could not walk away from it despite their initial exciting and pressing cosmic research interests. In that first ten days of discovery, they could not sleep or dismiss it from their minds. They wound up obsessed and were totally consumed with the encounter and realized their lives would never be the same after accepting the responsibility of reporting their unreal confrontation of a whole new world, much the way one can imagine one who insists of having seen an extra-terrestrial life form and/or unfathomable technologies therein associated.

With diamond and graphite existing both in bulk solid form, a molecular vapor form of pure carbon was a stunning shock! How could it be categorized as an equivalent form of matter to the millennially known unvaporizable bulk forms of the solid allotropes of diamond and graphite. The spectroscopists, however, could not dismiss it as some fluke as the observation of an amazingly stable glob of sixty carbon atoms in vapor form persistently revealed itself with each experimental trial along with much smaller amounts of other carbon vapors as with a seventy-carbon glob! So, in the moment of shock of encountering an indisputable new form of pure carbon, the spectroscopists put their heads together in an effort to explain in any way possible and out of their best abilities to imagine the nature of that sixty carbon glob that would generally be consistent with established science such that they could avoid breaking any of the rules of science and chemistry up that point in time.

What they came up with in that first ten days of discovery caught their imagination and that of the world of a most mesmerizing model of perfection hitherto known only in the abstract of mathematics and to an indefatigable iconic architect: a truncated icosahedron that colleagues from the math department declared a match for the three-dimensional geometry of a soccer ball of the most popular sport on earth. The unflagging architect and Mensa president had long been a unswerving proponent of such geodesic dome structures as being the structurally most stable possible; thus, the newly discovered member of eventually a vast world of the new allotrope members was named Buckminsterfullerene or simply the buckyball!

Surely thoughts must have crossed their mind that a wall of resistance would attempt to have them as the center focus of a witch burning at the stake. Such heresy of ever making public their ET witness surely would be their undoing with their being driven out of the hallowed halls of science with loss of position and livelihood under a cloud of shame and ridicule. Such happens to most who would not go along with the authorities as in the worlds of global warming or climate change and vaccines and alternative medicine adherents. Nevertheless, eleven years later, however, they were applauded for the courage and faith to take it on and see it through in Stockholm with the world rewarding them the 1996 Nobel Prize in Chemistry.

2. The Crossene Discovery and Eventual Universal Recognition and Acceptance

As the new allotrope of carbon, crossene, is now introduced in the instant disclosure, the fullerene story above can be viewed as a virtual cakewalk. The story of fullerene is essential in the instant disclosure on the discovery of crossenes if the power of the discovery is to be released in an expeditious fashion as unimaginable resistance is expected after over three decades of acceptance of a false ideation of the nature of fullerenes as being of a geodesic dome nature. The mesmerizing buckyball like the soccer ball is like an idol, vaunted written in all the textbooks and taught in all the lecture halls across the world with all researchers in the field necessarily having bend a knee to its lofty place it found in science with disobedience resulting in the ultimate of punishment in the hallowed halls of science with research grants and respect hitting rock bottom. Accordingly, it is clear how the obvious misconstrued and misleading nature of the fullerene discovery goes continues without a dare of resistance. So now for 35 years, progress has been stymied caught up in the misrepresentation of a geodesic dome model with much resulting consternation and confusion for lack of understanding the true nature of fullerene. Accordingly, much attention was given above regarding the history of the development of fullerenes in order to set the train back on the track especially in harnessing the wonders of crossenes. Accordingly, a dark age in science might be avoided to set free an amazing renaissance in science from the two gifts of fullerenes and crossenes. The three inventors of the instant disclosure had placed on their plate a wondrous gift easily missed just as was the case for the spectroscopists at Rice University 35 years ago.

As taught in Luke 12:48, the adage "To whom much has been entrusted, much is required" applies to both divinely appointed groups of three wise men. This summary section is so very important because of the huge age difference of the two different sets of inventors where the first set at the time of their discovery were of the age of the present inventors' youngest children. The spectroscopists spent the rest of their lives in defense and in nurturing of their world-changing discovery and the same is to be expected for the inventors of the instant disclosure though the years left for the present inventors may be cut short unless the longevity wonders observed for these new allotropes work sufficiently well on those in advanced age. The time required for universal acceptance and resultant innovation by the world may be cut short and therefore must proceed with the utmost of diligence and energy.

Now, the fullerene story might be considered a cakewalk in comparison to the newly introduced crossene story for the following reasons:

1. Crossenes are all multilayered without volatile/soluble purification benefits of C60 fullerene,
2. Crossene molecules are each unique, all different like snowflakes of irregular morphology,
3. Crossene and fullerene CNOs come in stand-alone and catenated forms w/o consistent form,
4. Crossenes appear simply black visually, little different from coal, coke, charcoal or soot dust,
5. Crossenes in nature come in highly impure form as with shungite,
6. Crossenes appear under electron microscope as a mix of fullerene and graphite,
7. Monotropic allotropes were confused lumping crossene w fullerene w graphitic language,
8. Raman spectroscopy differences were interpreted as varying degrees of fullerene orderedness,
9. Production was multimodal producing crossenes of a wide array of natures and properties,
10. Production of fullerene & crossene CNOs was unreproducible with no consistency in batches,
11. Existing structure/bonding theory and proposed production mechanisms were faulty and unuseful.

Crossene as a new allotrope faced discovery and recognition based upon the following factors:

1. Development of a consistent production process to uncontaminated CNOs of unlimited volume,
2. Developed simple exacting process for consistent conversion of fullerene CNO to crossenes,
3. Observation of almost tripling in density of the powder form of fullerene CNO to crossenes,
4. Observation of an almost extinction of ESR/EPR signal upon conversion of fullerene to crossene,
5. Observation of extraordinarily sharp Raman and XRD signals for crossene over fullerene CNOs,
6. Observation of a dramatic increase in TGA measurement and thus thermodynamic stability,
7. Observation of exceptional increase in electrical conductivity,
8. Observation of dramatically different thermal and radiation behavior in a microwave oven,
9 Antioxidant enhancement of crossene vs fullerene CNO of at least an order of magnitude.

Upon applying the newly developed bonding/structure model of the instant disclosure, a connection became clear between increased degrees of new kinds of electron delocalization capability for the respective monotrope carbon allotropes and observations of increased thermodynamic stability thereof. The dramatic increases in electron delocalization with increased thermodynamic stability for crossenes demanded an explanation in bonding and structure that wound up assigned as a crossover bond of a nontraditional or rarely invoked bonding concept beyond established covalent bonding theory and more along the lines of a kind of specific van der Waal attraction bonding. The crossover of electron delocalization between layers of the CNO led to the crossene name.

The dramatic reduction in ESR/EPR signal fit the highly electron delocalization model incorporating the whole molecule where any unpaired electrons could pair up with others as a result of the transformation from the fullerene CNO with unpaired electrons trapped in the multitude of independent layers to their release into the full crossene CNO structure that allows pairing up of previous unpaired electrons trapped in the fullerene CNO layers.

The microwave phenomenon of crossene CNOs behaving so drastically different from fullerene CNOs is seen as an almost infinite number of harmonic resonance possibilities for the crossene CNOs over the fullerene CNOs with their independently set apart layers. Accordingly, radiation is absorbed of any specific and all frequency possibilities that is then reorganized and modulated into a full spectrum of electromagnetic radiation thus accounting for the brilliant blinding light emitted from the microwave like a metal for the crossene.

[There does appear to be a reorganization of the crossene over time with repeated microwave oven exposure where the spectrum of light emitted has the visible component lost but not the exceptional thermal stimulation factor.]

Of course, exceptional conductivity and possibly eventually proven superconductivity with little or no resistance fits the new bonding/structure understanding as well accruing from unrestrained electron delocalization circulation and circuitry. The same electron delocalization capability model explains the amazing antioxidant capability where any unpaired electron generated in the crossene is dispersed over the whole molecules of millions of carbon atoms as opposed to seven atoms with phenolic antioxidant molecules.

3. Crossene Age Renaissance

A discovery or invention has value only if it can be used to solve a problem or advance technology in service to a society. Crossene CNOs and their precursor fullerene CNOs with their newly understood natures in bonding and structures open up a new world of innovations regarding health, electrical conductivity, coatings, emf interaction applications and lubricants among countless other opportunities.

1. Crossene Health

Antioxidant behavior has been reported in C60 fullerene as being 172 times that of vitamin C or ascorbic acid. This antioxidant attribute of fullerenes and especially crossene CNOs of a catenated form of the instant disclosure coupled most probably with electromagnetic frequency (emf) field effects may play a major role in the observation of a nearly doubling of life expectancy in the 2012 Baati C60 fullerene rat toxicity study. Longevity has been observed to have been at least doubled that of C60 fullerene for the crossene CNOs of the catenated fused onion form of the instant disclosure.

From the new understanding of bonding and structure of the instant disclosure, antioxidant behavior of fullerene and crossene CNOs can now be understood in regards to the key newly proposed electron delocalization concepts for fullerene CNOs and crossene CNOs. With the previous bonding and structure concept developed during the first ten days of discovery of C60 fullerene and extended over the next 35 years until the instant disclosure, no mention was made within the geodesic dome bonding model regarding any electron delocalization within fullerenes. The observation of accentuated antioxidant effects provides a more detailed understanding of the nature of the respective new concepts of electron delocalization for fullerenes and crossenes.

For the purposes of instruction, one can evaluate the 20th layer of the respective catenated fullerene and crossene CNOs of the instant disclosure. According to the formula for calculating the number of available loose electrons for electron delocalization in a particular concentric layer or shell of a fullerene CNO systems [number of electrons per shell=n2×60 where n is the shell number], the $20^{th}$ shell bears 24,000 carbon atoms. Accordingly, through the leftover dumbbell-shaped p-orbitals each donating one electron for electron delocalization for each of the trigonally substituted carbon of the 24,000 carbons, 12,000 electrons participate in a spherical delocalized cloud of electrons on each side of the $20^{th}$ layer of the fullerene system with the interior side having a greater electron density than the exterior side. The exterior side is thus set up to engage any and all reactive entities it encounters to mitigate its electron deficiency.

With respect to the fullerene antioxidant behavior, reactive oxygen species (ROS) form a covalent bond to the exterior surface thereby capturing one of the 12,000 electrons participating in electron delocalization on the exterior surface. So, where there were initially 24,000 electrons involved in the electron delocalization on the 20th layer, now after the quenching of an ROS free radical and thus performing an antioxidant function, the $20^{th}$ layer has one less electron available in its spherical electron delocalization network. So, where an even number of electrons were available on both sides of the $20^{th}$ layer, now an odd number of electrons are involved in the delocalized electron system. Accordingly, one of the 23,999 leftover delocalized electrons is unpaired and thus would be highly reactive but for being highly delocalized with the other 23,998 electrons. It is this kind of electron delocalization that stabilizes an unpaired electron arising from quenching an ROS in the case of vitamin C and also sterically hindered phenolics but the degree of stabilization of the unpaired electron on the $20^{th}$ layer of the fullerene CNO is roughly 4000 times that of the phenolic example.

For crossene CNOs, any unpaired electron formed during the quenching of an ROS is stabilized not with the electron delocalization of an individual shell but over the whole crossene molecule. That is the nature of the new crossene allotrope that makes available the whole molecule of millions of carbon atoms for stabilizing an unpaired electron generated during an antioxidant process. It is the defining crossover between shells for electron delocalization in the crossene CNOs that is set up during the annealing process during the conversion of the fullerene CNO precursor to the crossene CNO. Due to the limitation of instantaneous kinetics at the time of conversion likened to a long chain dominos concertedly falling, no two highly irregularly shaped holes or voids, or alternatively viewed, ribbon-like structures are the same as electron delocalization seeks an optimal degree of electron delocalization during the conversion without regard to producing any one particular product structure or network of electron delocalization.

With new 3D concepts for electron delocalization first described in the instant disclosure, one can understand how C60 fullerene reportedly exhibits increased antioxidant behavior over vitamin C. The reported factor of 172 times greater than vitamin C can be partially explained by C60 fullerene having 60 carbons over which electron delocalization can proceed versus only six atoms of a mixture of half and half carbon and oxygen for vitamin C. If it were just numbers of atoms over which electron delocalization proceeds in its effectiveness in stabilizing unpaired electrons arising from ROS, one would expect that the potency of C60 fullerene would be only ten times that of vitamin C. Phenolics involve only seven atoms for stabilizing unpaired electrons of six carbons from the benzene ring plus the phenolic oxygen atom and thus C60 fullerene would then be expected to be a bit less than ten times that of phenolic antioxidants. The reported factor of 172 times greater potency for fullerene C60 is then, in fact, accounted for by only roughly about 5% based upon the number of atoms involved in the electron delocalization, sixty for C60 fullerene versus six for vitamin C and seven for phenolics.

The reported 172 factor superiority of C60 fullerene in antioxidant behavior over vitamin C or ascorbic acid cannot be accounted for on the basis of individual atoms involved in the delocalization network alone. In fact, when taking into account the number of atoms involved in the electron delocalization network of the respective C60 fullerene and ascorbic systems, the C60 fullerene system remains superior in antioxidant behavior by a factor of 17.2 or roughly 20. So, there must be something exceptional about the electron delocalization involving 3D fullerene concentric shells over 2D ascorbic acid or phenolics. There are several explanations for the superiority of 3D fullerene systems especially of the fullerene CNO systems:

a. Fullerenes and crossene being of nanometer size being able to reach every cell and cell organelle in the body.

b. Fullerene's and crossene's multi-dimensional endlessly or infinitely connected spherical electron delocalization network per individual layer for fullerenes as CNOs and otherwise and the whole molecule for crossene CNOs unavailable to the 2D ascorbic acid or phenolic systems.

c. Fullerene's and crossene's ROS addition mechanism versus the 2D hydrogen atom abstraction mechanism.

d. Fullerene's and crossene's independence from the requirement of partnering molecules of a cascading chain for antioxidant regeneration.

e. Fullerene's and crossene's carbon atoms involved in the antioxidant process undergoing continued antioxidant activity without the requirement of an outside regeneration partner molecule but, in fact, by the very ROS it is quenching to the point that the fullerene or crossene system quenches a total of four ROS per carbon atom with its eventual generation of carbonic acid that undergoes eventually carbon dioxide expulsion from the biological system through the lungs whereas the 2D systems require the interplay with other molecules for regeneration of their antioxidant capability in a cascade of additional antioxidant components in the biological system.

f. C60 fullerene exhibiting the greatest degree of external surface reactivity that arises from its smallest size of fullerenes with its corresponding greatest degree of curvature having accordingly the greatest difference in surface electron density between its interior and exterior surfaces due to its greatest degree of curvature required accommodating its sixty carbon atoms, thirty electrons delocalized on each side, in its fullerene system that initiates the layering process during synthesis of fullerene CNOs due to this dramatic differential of the electron density on the interior versus the exterior side.

g. Fullerene and crossene CNOs particularly of catenated fused onion systems of the instant disclosure bearing millions of carbon atoms and thus delocalized electrons having many orders of magnitude greater antioxidant capacity to that of simple C60 fullerenes.

The considerations above can be readily understood examining one particular ROS involved in the fullerene quenching process of the hydroxide radical that is understood as the highly reactive species resulting from the homolytic cleavage of hydrogen peroxide or other peroxides, similar to other peroxides like benzoyl peroxide that catalyzes olefin polymerization explosively even in small quantities, much more in tank car quantities. So, the hydroxide radical forms a covalent bond to the fullerene system to produce something like a phenolic 0-H from a 2D perspective with the once very reactive unpaired electron on the hydroxide radical now highly stabilized as a smear across the vast network of 3D delocalized electrons. In this example for instructive purposes only, the hydrogen atom of the fullerenic 0-H is then plucked off by a second hydroxide radical thereby quenching the 0-H radical by generating an electronically balanced and neutral water molecule with the formation of a carbonyl of a ketone functional group on the surface of the fullerene following the scission of the first of that carbon's previous trigonal substitution. With the quenching of the second hydroxide radical, the fullerene molecules starts to undergo its unraveling decomposition process with the eventual breakup of the fullerene electron delocalization system. The third hydroxide radical then gets quenched upon attacking the carbonyl carbon thereby breaking an additional adjacent fullerene carbon-carbon bond with the fullerene electron delocalization network stabilizing the resulting unpaired electron introduced into the fullerene system in thereby producing a carboxylate group tethered by a lone carbon-carbon covalent bond remaining to the slowly falling apart fullerene system. Finally, the fourth hydroxide radical attacks the carboxylate carbonyl carbon to break the last carbon-carbon bond to the fullerene system with the release of carbonic acid that eventually is removed from the body through the lungs as carbon dioxide.

Crossene antioxidant activity proceeds in similar fashion except that the unpaired electron induced upon the crossene CNO system is stabilized far more robustly over the whole crossene molecule than just over the individual layer of electronic delocalization of a fullerene system. As with a fullerenic system, however, the same step-by-step oxidation of each carbon atom by four separate hydroxide radicals to the eventual release of carbonic acid from the crossene CNO system and subsequently carbon dioxide from the lungs. Upon the evaluation of the antioxidant behavior of crossenes by a specialist, Dr. Gabriel Gojon, Co-Founder and CTO of SulfaGenix, Inc., the antioxidant activity of the catenated crossene CNOs of the instant disclosure was reported to be at least an order of magnitude greater than that for the corresponding catenated fullerene CNO precursor to the crossene CNO.

The differential in electron density between the exterior and interior in fullerenes also appears to provide another healthful function in detoxing. Activated charcoal detoxes by capturing toxins in the gut in pores associated with the exceptional surface area of activated carbon systems. Activated charcoal, however, is not a nanocarbon material like fullerene and crossene CNOs. Fullerene and crossene CNOs are viewed to serve in detoxification processes through its reactive exterior surface in capturing and denaturing or otherwise passivating certain toxins. Again, due to the fullerene and crossene CNOs can act through the gut not just in the gut but also after passing through the gut lining into the blood supply not only for reducing oxidative stress in the mitochondria through its antioxidant behavior where the CNOs are eventually delivered into potentially every cell of the body after entering the blood supply but in detoxication activities. A particularly exciting health value of fullerene and crossene CNOs is not only its detoxification behavior but also their apparent anti-inflammatory behavior.

Such anti-inflammatory behavior seems to manifest itself in fast and almost pain-free rapid healing of burns and abrasions plus insect bites or stings. Such anti-inflammatory capacity is appears to be proceeding most intriguingly regarding multiple testimonies of kidney stone treatment. In one anecdotal report by a self-testing individual after the passage of the inflaming kidney stones was that the stones were visibly coated in black that would be indicative of the color of the fullerene or crossene CNOs. The kidney stone scenario imagined is that as the urinary tubing is serrated by the by the kidney stone with a multitude of sharp chards that collect inflamed tissue on its surface. As the blood supply with fullerene or crossene CNOs distributed in it passes by the injuries of the urinary tract, the CNOs are viewed as being drawn to the free-radical-laden inflamed torn tissue and start collecting on the tissue coated kidney stone until it is completely encapsulated by the CNOs. Accordingly, the sharp chards would become no longer an issue and also the growth of the kidney stone would be halted. Finally, the CNO-coated kidney stone is then seen to take on the properties of a lubricating coating due to the known tribological properties of the CNOs. What a breakthrough in overcoming the lifetime misery endured by many suffering from kidney stone inflammation often requiring for many three and four surgeries per year!

These and other health considerations are just now being published through anecdotal testimonies at the website www.GrafexSuperC60.com. Also, in the information only website are given the details of the longevity studies regarding crossene CNOs including two different basic means of CNO introduction: orally and subcutaneously. Incidentally, the exceptional life extension of some three to five times the normal life expectancy proceeded with immune-deficient mice in a CNO microwave-directed ablation study involving a solitary subcutaneous injection. Additionally, local and systemic health improvement effects have been observed transdermally in a poultice or cream application. Undoubtedly, direct blood infusion should also produce health benefits.

2. Crossene Electrical Conductivity

Crossenes have already demonstrated a certain degree of exceptional electrical conductivity in the instant disclosure. Application of that attribute would be of great interest particularly in regard to electrical transmission in that the possibility of superconductivity at room temperature might be expected. Accordingly, if transmission of electricity from power generation facilities to the site of utilization could proceed with greatly reduced resistance through the transmission lines, the routinely experienced roughly 30% loss in the energy of production in the power plants could be reduced dramatically without loss through heat generation in the transmission wires.

Already, the effect of pressure for increasing electrical conductivity is demonstrated in the instant disclosure. The development of transmission lines involving crossenes held under extreme pressure accordingly would be expected to exhibit transmission with greatly reduced resistance. Known in the literature and reported in a 2015 review article by Georgakilas, Perman, Tucek and Zboril is the dimerization of fullerenes. Such may explain the increased electrical conductivity of crossene under pressure.

Another avenue for taking advantage of crossene's exceptionally free flowing electrons through electron delocalization throughout the molecule is to provide a conductive bridge between crossene molecules. A conductive bridge would allow extension of the exceptionally free flowing electrons in crossenes to pass to other such crossene molecules to the point of yielding a transmission line of exceptionally low resistance and thus exceptionally low losses in heat generation and thus energy for transmission.

Already known in the literature discussed in the 2014 review by Bartelmess and Giordani are effective functionalization or decoration reactions for the surfaces of fullerene CNOs that has been also demonstrated for crossene CNOs under confidentiality agreement. If the reactant utilized in the functionalization reaction on the surface of the crossene involves in a multifunctional molecule, there is the possibility of conductively engaging a whole series of crossene molecule into an electrical transmission line of little or no resistance.

One particularly intriguing candidate for connection to the surface of the crossenes is a benzene ring bearing two or more amino groups using a diazonium salt intermediate as noted in the 2014 review article citing Flavin, Chaur, Echegoyen and Giordani: Functionalization of Multilayer Fullerenes (Carbon Nano-Onions) using Diazonium Compounds and "Click" Chemistry; Kevin Flavin[r], Manuel N. Chau[‡], Luis Echegoyen[‡], Silvia Giordani*[r] Org. Lett., 2010, 12, 4, 840-843, Publication Date: Jan. 21, 2010 https://doi.org/10.1021/ol902939f.

The connection between the crossenes involved would be conductive as the connection would be directly through a benzene ring without any intervening obstacles to uninterrupted conductivity. Another possible candidate would be a benzene ring with an amino group and a carboxylic group, especially p-aminocarboxylic acid, wherein connection between the benzene ring and crossene molecules would proceed first again through a diazonium salt intermediate followed by a thermally induced decarboxylation of a salt formed from the benzoic acid substituent on the crossene surface therein connecting the decarboxylated carbon atom of the benzene ring to another crossene system. The latter procedure could be useful additionally in connecting a crossene unit to a metallic surface.

3. Crossene Coatings

Coatings suffer from degradation and thus require regular maintenance of stripping and reapplication. Any reduction in need of maintenance would be a major savings in time and materials of substantial economic value. The inclusion of crossenes of the catenated nature of the instant disclosure significantly extends the life of coating under even the harshest environments for the primary reasons:

a. Interaction of the coating matrix with the reactive surface of the crossene chains in crosslinking,
b. Interaction of the coating surface with the reactive surface of the crossene chains,
c. Preservation of the coating matrix through crossene's antioxidant and uv-absorption properties, Beach concrete benches and tables had required repainting every six months but, after crossene inclusion in the paint matrix, years passed without a need for maintenance. The hulls of a ship that had suffered from barnacles and coating degradation requiring regular maintenance lasts many more years upon the inclusion of crossene without the need of maintenance. High heat-enduring surfaces requiring repainting between every use persist without need for maintenance for years.

4. Crossene EMF Applications

Crossenes being molecules of unlimited electron delocalization provides opportunities of emf absorption through unlimited electron harmonic modes. Once absorbed, the matrix of electrons could modulate an absorbed emf radiation of a narrow range of frequencies into the full spectrum of emf radiation. Evidence of this phenomenon is observed by the production of a blinding white light when crossene material is irradiated in a microwave oven. The release of such full spectrum emf radiation can interact with nearby surrounding materials with an exceptional thermal elevation. Accordingly, crossenes in minute amounts could serve as an effective susceptor strip for microwave cooking as for popcorn. Additionally, crossenes mixed with certain thermoset coating could dramatically shorten cure times through exposure to directed microwave radiation for instance. In paints and coatings, sensitive electronics could be protected from adverse effects of solar flares or any potential emp event.

5. Crossene Lubricants

Lubricating oils are essential for low cost efficiency and long service of mechanical devices as in motors but need frequent replacement due to degradation during service. Much loss in such lubricating maintenance could be reduced through increase in period of service before replacement is needed. Crossenes of the catenated nature of the instant disclosure are highly hydrophobic and, though with such immense molecular weight are insoluble in any medium, are exceptionally miscible in oils, particularly hot churning oils. With crossene possessing innate tribological properties, it is expected to have a positive effect on the oil in the smooth operation of the engine. Crossene, having a reactive exterior surface may interact with the metal parts in laying out a thin lubricating film especially as engine use extends to long periods of hot churning use. Of possible greatest value as an oil additive, however, the inclusion of crossenes in lubricating oils may serve as an antioxidant to minimize degradation of the oil and extend its lifetime thereby allowing for less maintenance and loss due to the customary need for frequent oil change.

III. Potential Crossene Surface Modifications

Known and presented in a recent review article.sup.8 is that C60 fullerene and fullerene onions have a reactive outer surface amenable to all manner of modification or, in nano-carbon-specific verbiage, of decoration that translates into all manner of means of functionalizing the surface for particular purposes and applications. Incidentally, as with the foregoing footnote, in the 2014 year of this review publication, what is now known as the crossene allotrope was identified as a fullerene "polyhedron onion.".sup.8Bartelmess J, Giordani S. Carbon nano-onions (multi-layer fullerenes): Chemistry and applications. Beilstein J. Nanotechnol. 2014; 5:1980-8; doi: 10.3762/bjnano.5.207.

Functionalization may proceed on the outer surface for example through potassium hydroxide or oxidation treatments as in treatment involving nitric acid, through addition or cycloaddition reactions, through simple fluoride or halogen addition reactions, through free radical addition reactions for preparing the nanoparticles for further functionalization as in sulfonation, and other means . . . sup. 11.sup. 11 Bhinge S D. Carbon nano-onions—An overview. J Pharm Chem Chem Sci. 2017; 1 (1): 1-2. J Pharm Chem Chem Sci 2017 Volume 1 Issue 1 [Editorial], Accepted on Oct. 13, 2017 http://www.alliedacademies.org/journal-pharmaceutical-chemistry-chemical—science/.

IV. Potential Crossene Applications

As can be readily seen from the Characterization and Modification sections, crossenes offer a wide range of applications regarding, but not limited to material science, metallurgical modifications as with alloy improvements with replacement of traditional carbon components and also covetics, aerospace, solar energy, 3D printing, polymers and plastics, polymer or plastic or inorganic composites or matrices, emf thermoset plastic curing, paints and coatings, oxidation/combustion resistance application, glass treatments, thermal insulation, electronics, electrical transmission, batteries or capacitors, emf attenuation/reception, catalysis, tribology, optical limiting, water resistance, cancer and dermatological treatments, preventive medicine, biological ablation therapy, emf-therapy, radiation protection, radiological contrasting agents including other bioimaging technologies, drug or gene agent delivery, toxin and heavy metal removal, and other biotechnology innovations.

What is claimed is:

1. An anti-inflammatory agent comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

2. The anti-inflammatory agent of claim 1, wherein the carbon material is functionalized.

3. The anti-inflammatory agent of claim 1, wherein the carbon material is doped with one or more heteroatoms.

4. An antioxidant comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

5. The antioxidant of claim 4, wherein the carbon material is functionalized.

6. The antioxidant of claim 4, wherein the carbon material is doped with one or more heteroatoms.

7. An electronic device sheath comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

8. The electronic device sheath of claim 7, wherein the carbon material is functionalized.

9. The electronic device sheath of claim 7, wherein the carbon material is doped with one or more heteroatoms.

10. A Wi-Fi system comprising the electronic device sheath of claim 7.

11. A battery comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

12. The battery of claim 11, wherein the carbon material is functionalized.

13. The battery of claim 11, wherein the carbon material is doped with one or more heteroatoms.

14. A capacitor comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

15. The capacitor of claim 14, wherein the carbon material is functionalized.

16. The capacitor of claim 14, wherein the carbon material is doped with one or more heteroatoms.

17. A computer comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

18. The computer of claim 17, wherein the carbon material is functionalized.

19. The computer of claim 17, wherein the carbon material is doped with one or more heteroatoms.

20. A cell phone comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

21. The cell phone of claim 20, wherein the carbon material is functionalized.

22. The cell phone of claim 20, wherein the carbon material is doped with one or more heteroatoms.

23. A lubricant comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

24. The lubricant of claim 23, wherein the carbon material is functionalized.

25. The lubricant of claim 23, wherein the carbon material is doped with one or more heteroatoms.

26. A coating or a paint, each comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

27. The coating or the paint of claim 26, wherein the carbon material is functionalized.

28. The coating or the paint of claim 26, wherein the carbon material is doped with one or more heteroatoms.

29. A 3D printer or a 2D printer, each comprising a carbon material that comprises a multilayered three dimensional nanocarbon array present in catenated states, wherein stabilizing electron delocalization crosses between layers in an interlayer connectivity bonding system involving the whole carbon array; and wherein the carbon material is derived from a catenated fullerene carbon nano-onion (CNO) precursor.

30. The 3D printer or the 2D printer of claim 29, wherein the carbon material is functionalized.

31. The 3D printer or the 2D printer of claim 29, wherein the carbon material is doped with one or more heteroatoms.

* * * * *